US012569557B2

(12) United States Patent
Jin et al.

(10) Patent No.: US 12,569,557 B2
(45) Date of Patent: Mar. 10, 2026

(54) TARGETING MODC TO ENHANCE VACCINE EFFICACY ON MUCOSAL SURFACE

(71) Applicant: UNIVERSITY OF FLORIDA RESEARCH FOUNDATION, INCORPORATED, Gainesville, FL (US)

(72) Inventors: Lei Jin, Gainesville, FL (US); Samira Mansouri, Saratoga Springs, NY (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 1352 days.

(21) Appl. No.: 17/280,986

(22) PCT Filed: Sep. 27, 2019

(86) PCT No.: PCT/US2019/053548
§ 371 (c)(1),
(2) Date: Mar. 29, 2021

(87) PCT Pub. No.: WO2020/069375
PCT Pub. Date: Apr. 2, 2020

(65) Prior Publication Data
US 2021/0353748 A1 Nov. 18, 2021

Related U.S. Application Data

(60) Provisional application No. 62/737,154, filed on Sep. 27, 2018.

(51) Int. Cl.
| | |
|---|---|
| *A61K 39/395* | (2006.01) |
| *A61K 31/708* | (2006.01) |
| *A61K 31/7084* | (2006.01) |
| *A61K 38/19* | (2006.01) |
| *A61K 39/09* | (2006.01) |
| *A61K 39/39* | (2006.01) |
| *A61P 31/04* | (2006.01) |
| *A61K 39/00* | (2006.01) |

(52) U.S. Cl.
CPC ............ *A61K 39/39* (2013.01); *A61K 31/708* (2013.01); *A61K 31/7084* (2013.01); *A61K 38/191* (2013.01); *A61K 39/092* (2013.01); *A61K 39/3955* (2013.01); *A61P 31/04* (2018.01); *A61K 2039/543* (2013.01); *A61K 2039/55522* (2013.01); *A61K 2039/55561* (2013.01); *A61K 2039/575* (2013.01)

(58) Field of Classification Search
CPC ................ A61K 47/68; A61K 47/6801; A61K 47/6803; A61K 47/6809
See application file for complete search history.

(56) References Cited

U.S. PATENT DOCUMENTS

| | | | |
|---|---|---|---|
| 2014/0057319 | A1 | 2/2014 | Naso et al. |
| 2016/0175427 | A1 | 6/2016 | Weiner et al. |
| 2017/0095548 | A1 | 4/2017 | Malouin et al. |

FOREIGN PATENT DOCUMENTS

| | | | | | |
|---|---|---|---|---|---|
| WO | 2016203025 | A1 | 12/2016 | | |
| WO | 2017100305 | A2 | 6/2017 | | |
| WO | WO-2018053508 | A1 * | 3/2018 | .......... | A61K 31/4745 |
| WO | WO-2018140831 | A2 * | 8/2018 | ......... | A61K 47/6803 |
| WO | WO-2019084060 | A1 * | 5/2019 | ......... | A61K 47/6803 |
| WO | 2020069375 | A1 | 4/2020 | | |

OTHER PUBLICATIONS

PCT/US2019/053548, Search report and written opinion, mailed Feb. 19, 2020, 14 pages.
Baratin, Myriam et al., "Homeostatic NF-kB Signaling in Steady-State Migratory Dendritic Cells Regulates Immune Homeostasis and Tolerance", Immunity, Apr. 21, 2015, vol. 42, pp. 627-639.
Blaauboer, Steven M. et al., "MPYS/STING-Mediated TNF-, Not Type I IFN, Is Essential for the Mucosal Adjuvant Activity of (3'-5')-)-Cyclic-Di-Guanosine-Monophosphate In Vivo", J Immunol, 2014, vol. 192, pp. 492-502.
Blaauboer, Steven et al., "The mucosal adjuvant cyclic di-GMP enhances antigen uptake and selectively activates binocytosis-efficient cells in vivo", eLife, 2015, vol. 4, e06670, 25 pages.
Burdette, Dara L. et al., "STING is a direct innate immune sensor of cyclic di-GMP", Nature, Oct. 27, 2011, vol. 478, pp. 515-519.
Caton, Michele L. et al., "Notch—RBP-J signaling controls the homeostasis of CD8—dendritic cells in the spleen", Jem, Jul. 9, 2007, vol. 204, No. 7, pp. 1653-1664.
Crowley, M. et al., "The Cell Surface of Mouse Dendritic Cells: FACS Analyses of Dendritic Cells from Different Tissues Including Thymus", Cellular Immunology, 1989, vol. 118, pp. 108-125.
Dempsey, Alan et al., "Innate immune recognition of DNA: A recent history", Virology, 2015, vol. 479, No. 480, pp. 146-152.
De Silva, Nilushi S. et al., "Impairment of Mature B Cell Maintenance upon Combined Deletion of the Alternative NF-kB Transcription Factors RELB and NF-kB2 in B Cells", J Immunol, 2016, vol. 196, pp. 2591-2601.
Ebensen, Thomas et al., "The Bacterial Second Messenger cdiGMP Exhibits Promising Activity as a Mucosal Adjuvant", Clinical and Vaccine Immunology, Aug. 2007, vol. 14, No. 8, pp. 952-958.

(Continued)

*Primary Examiner* — Micah Paul Young
(74) *Attorney, Agent, or Firm* — Timothy H. Van Dyke; Wolter Van Dyke Davis, PLLC

(57) ABSTRACT

Described herein are novel vaccine compositions and methods for use thereof in inducing an immune response in a subject especially aged subjects. Specifically exemplified are vaccine compositions that include an antigen; a cyclic dinucleotide; soluble tumor necrosis factor (TNF); or a CD64 antibody or antibody fragment. Optionally, the vaccine composition comprises a TNF conjugated with a moDC targeting moiety in addition to or in place of TNF or CD64 antibody or antibody fragment, or both TNF and CD64 antibody or antibody fragment.

18 Claims, 62 Drawing Sheets

(56)          References Cited

OTHER PUBLICATIONS

Erickson, Sharon L. et al., "Decreased sensitivity to tumour-necrosis factor but normal T-cell development in TNF receptor-2-deficient mice", Nature, Dec. 8, 1994, vol. 372, pp. 560-563.

Gogoi, Himanshu et al., "New MoDC-Targeting TNF Fusion Proteins Enhance Cyclic Di-GMP Vaccine Adjuvanticity in Middle-Aged and Aged Mice", Frontiers in Immunology, Aug. 2020, vol. 11, article 1674, 13 pages.

Gray, Peter M. et al., "Evidence for cyclic diguanylate as a vaccine adjuvant with novel immunostimulatory activities", Cellular Immunology, 2012, vol. 278, pp. 113-119.

Grell, Matthias et al., "The Transmembrane Form of Tumor Necrosis Factor Is The Prime Activating Ligand of the 80 kDa Tumor Necrosis Factor Receptor", Cell, Dec. 1, 1995, vol. 83, pp. 793-802.

Grell, Matthias et al., "The type 1 receptor (CD120a) is the high-affinity receptor for soluble tumor necrosis factor", Proc. Natl. Acad. Sci., Jan. 1998, vol. 95, pp. 570-575.

Guilliams, Martin et al., "Unsupervised High-Dimensional Analysis Aligns Dendritic Cells across Tissues and Species", Immunity, 2016, vol. 45, pp. 669-684.

Hanson, Melissa C. et al., " Nanoparticulate STING agonists are potent lymph node-targeted vaccine adjuvants", J Clin Invest., 2015, vol. 125, No. 6, pp. 2532-2546.

Hildner, Kai et al., "Batf3 Deficiency Reveals a Critical Role for CD8a + Dendritic Cells in Cytotoxic T Cell Immunity", Science, Nov. 14, 2008, vol. 322, pp. 1097-1100.

Holt, P.G. et al., "Dendritic Cells in the Respiratory Tract", International Reviews of Immunology, 1990, vol. 6, No. 2, article 3, pp. 139-149.

Hu, Dong-Liang et al., "cdiGMP as a vaccine adjuvant enhances protection against systemic methicillinresistant *Staphylococcus aureus* (MRSA) infection", Vaccine, 2009, vol. 27, pp. 4867-4873.

Jin, Lei et al., "STING/MPYS Mediates Host Defense against Listeria monocytogenes Infection by Regulating Ly6C hi Monocyte Migration", J Immunol, 2013, vol. 190, pp. 2835-2843.

Jin, Lei et al., "MPYS Is Required for IFN Response Factor 3 Activation and Type I IFN Production in the Response of Cultured Phagocytes to Bacterial Second Messengers Cyclic-di-AMP and Cyclic-di-GMP", J Immunol, 2011, vol. 187, pp. 2595-2601.

Karaolis, David K.R. et al., "Cyclic Di-GMP Stimulates Protective Innate Immunity in Bacterial Pneumonia", Infection and Immunity, Oct. 2007, vol. 75, No. 10, pp. 4942-4950.

Klein, Ulf et al., "Transcription factor IRF4 controls plasma cell differentiation and class-switch recombination", Nature Immunology, Jul. 7, 2006, vol. 7, pp. 773-782.

Langlet, Christelle et al., "CD64 Expression Distinguishes Monocyte-Derived and Conventional Dendritic Cells and Reveals Their Distinct Role during Intramuscular Immunization", J Immunol, 2012, vol. 188, pp. 1751-1760.

Libanova, Rimma et al., "Cyclic di-nucleotides: new era for small molecules as adjuvants", Microbial Biotechnology, 2012, vol. 5, No. 2, pp. 168-176.

Lugt, Bryan Vander et al., "Transcriptional programming of dendritic cells for enhanced MHC class II antigen presentation", Nature Immunology, Feb. 2014, vol. 15, No. 2, 10 pages.

Madhun, Abdullah S. et al., "Intranasal cdiGMPadjuvanted plantderived H5 influenza vaccine induces multifunctional Th1 CD4+ cells and strong mucosal and systemic antibody responses in mice", Vaccine, 2011, vol. 29, pp. 4973-4982.

Mansouri, Samira et al., "Lung TNFR2-CD11b+CD24+CD64-DC direct moDCs to generate cyclic di-GMP adjuvant responses in vivo", Apr. 22, 2018, 56 pages.

Metzger, Dennis W. et al., "Limited Efficacy of Antibacterial Vaccination Against Secondary Serotype 3 Pneumococcal Pneumonia Following Influenza Infection", JID, Aug. 1, 2015, vol. 212, pp. 445-452.

Mildner, Alexander et al., "Development and Function of Dendritic Cell Subsets", Immunity, May 15, 2014, vol. 40, pp. 642-656.

Murphy, Kenneth M. "Transcriptional Control of Dendritic Cell Development", Advances in Immunology, 2013, vol. 120, pp. 239-267.

Ogunniyi, Abiodun D. et al., "cdiGMP is an effective immunomodulator and vaccine adjuvant against pneumococcal infection", Vaccine, 2008, vol. 26, pp. 4676-4685.

Pfeffer, Klaus et al., "Mice Deficient fot the 55 kd Tumor Necrosis Factor Receptor Are Resistant to Endotoxic Shock, yet Succumb to L. monocytogenes Infection", Cell, May 7, 1993, vol. 73, pp. 457-467.

Plantinga, Maud et al., "Conventional andMonocyte-DerivedCD11b+ Dendritic Cells Initiate and Maintain T Helper 2 Cell-Mediated Immunity to House Dust Mite Allergen", Immunity, Feb. 21, 2013, vol. 38, pp. 322-335.

Schlitzer, Andreas et al., "IRF4 Transcription Factor-Dependent CD11b+ Dendritic Cells in Human and Mouse Control Mucosal IL-17 Cytokine Responses", Immunity, May 23, 2013, vol. 38, pp. 970-983.

Sichien, Dorine et al., "IRF8 Transcription Factor Controls Survival and Function of Terminally Differentiated Conventional and Plasmacytoid Dendritic Cells, Respectively", Immunity, Sep. 20, 2016, vol. 45, pp. 626-640.

Smith, Tyrel T. et al., "Biopolymers codelivering engineered T cells and STING agonists can eliminate heterogeneous tumors", J Clin Invest., 2017, vol. 127, No. 6, pp. 2176-2191.

Steinman, Ralph M., "Decisions About Dendritic Cells: Past, Present, and Future", Annu. Rev. Immunol., 2012, vol. 30, pp. 1-22.

Suzuki, Shoichi et al., "Critical roles of interferon regulatory factor 4 in CD11bhighCD8a2 dendritic cell development", PNAS, Jun. 15, 2004, vol. 101, No. 24, pp. 8981-8986.

Tamoutounour, Samira et al., "CD64 distinguishes macrophages from dendritic cells in the gut and reveals the Th1-inducing role of mesenteric lymph node macrophages during colitis", Eur. J. Immunol., 2012, vol. 42, pp. 3150-3166.

Vremec, David et al., "The Surface Phenotype of Dendritic Cells Purified from Mouse Thymus and Spleen: Investigation of the CD8 Expression by a Subpopulation of Dendritic Cells", J. Exp. Med. Jul. 1992, vol. 176, pp. 47-58.

Wajant, H. et al., "Tumor necrosis factor signaling", Cell Death and Differentiation, 2003, vol. 10, pp. 45-65.

Wallach, D. et al., "Tumor Necrosis Factor Receptor and Fas Signaling Mechanisms", Annu. Rev. Immunol., 1999, vol. 17, pp. 331-367.

Wang, Zili et al., "STING activator c-di-GMP enhances the anti-tumor effects of peptide vaccines in melanoma-bearing mice", Cancer Immunol Immunother, 2015, vol. 64, pp. 1057-1066.

Wu, Jiaxi et al., "Innate Immune Sensing and Signaling of Cytosolic Nucleic Acids", Annu. Rev. Immunol., 2014, vol. 32, pp. 461-488.

Yan, Hongbin et al., "30,50-Cyclic diguanylic acid elicits mucosal immunity against bacterial infection", Biochemical and Biophysical Research Communications, 2009, vol. 387, pp. 581-584.

Zhao, Lisa et al., "c-di-GMP protects against intranasal Acinetobacter baumannii infection in mice by chemokine induction and enhanced neutrophil recruitment", International Immunopharmacology, 2011, vol. 11, pp. 1378-1383.

* cited by examiner cDC2 play a central role in mediating the adjuvant activity of CDG cDC2 expression of TNFR2 is required for CDG-induced lung cDC2 maturation *in vivo* by activating RelB

A

Serum Anti-PspA IgG

BALF Anti-PspA IgA

Antibody Dilutions

---- WT PspA/CDG

——— TNFR1-/- PspA/CDG

······ TNFR2-/- PspA/CDG

--·-- WT PspA

C

D

E

A cDC2 expression of TNFR2 and RelB is required for Th1 and
Th17 responses, but dispensable for CDG-induced antibody response —— WT CDG/PspA ······ IRF4$^{fl/fl}$CD11c$^{cre}$ CDG/PspA —·—· IRF4$^{fl/fl}$CD11c$^{cre}$+WT cDC2 CDG/PspA ———— IRF4$^{fl/fl}$CD11c$^{cre}$+WT cDC2 PspA —·—· IRF4$^{fl/fl}$CD11c$^{cre}$+TNFR2$^{-/-}$ cDC2 CDG/PspA ······ IRF4$^{fl/fl}$CD11c$^{cre}$+TNFR2$^{-/-}$ cDC2 PspA G
TNFR2$^+$ cDC2
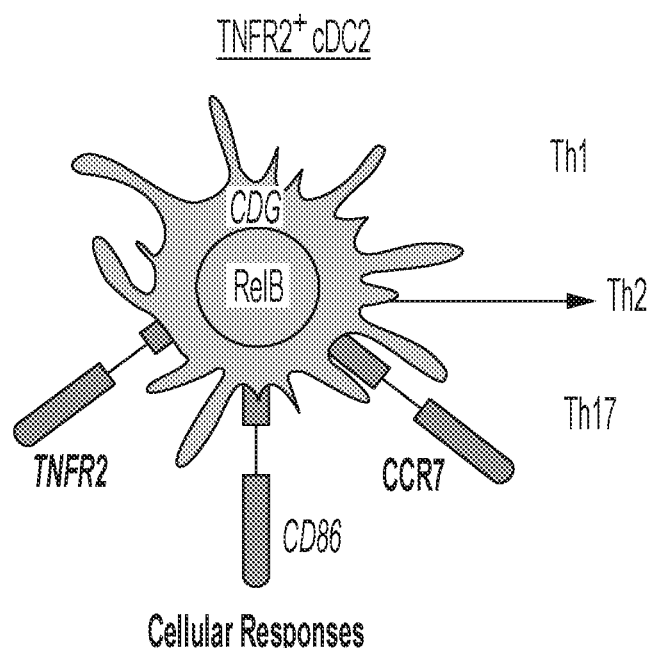
Cellular Responses
TNFR2$^-$ cDC2
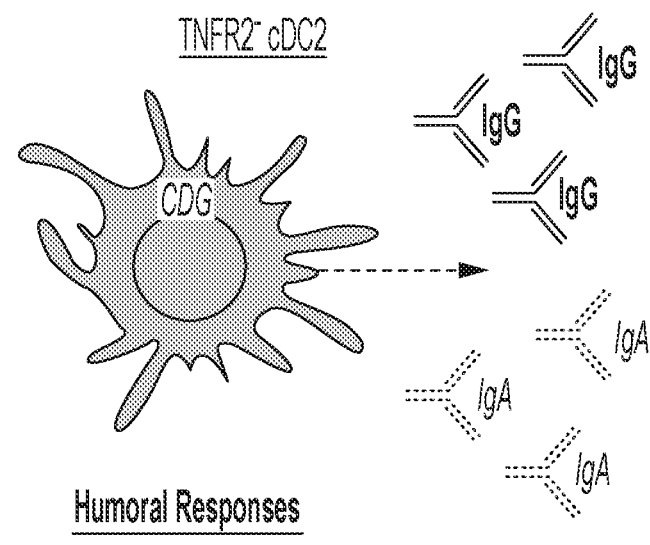
Humoral Responses
FIG. 4G

D

E

TNFR2⁻ cDC2 express mTNF but have few processed antigen

A

B

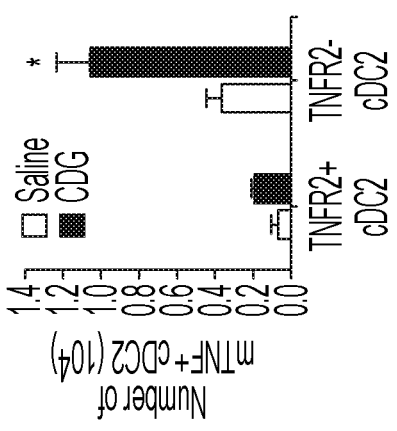
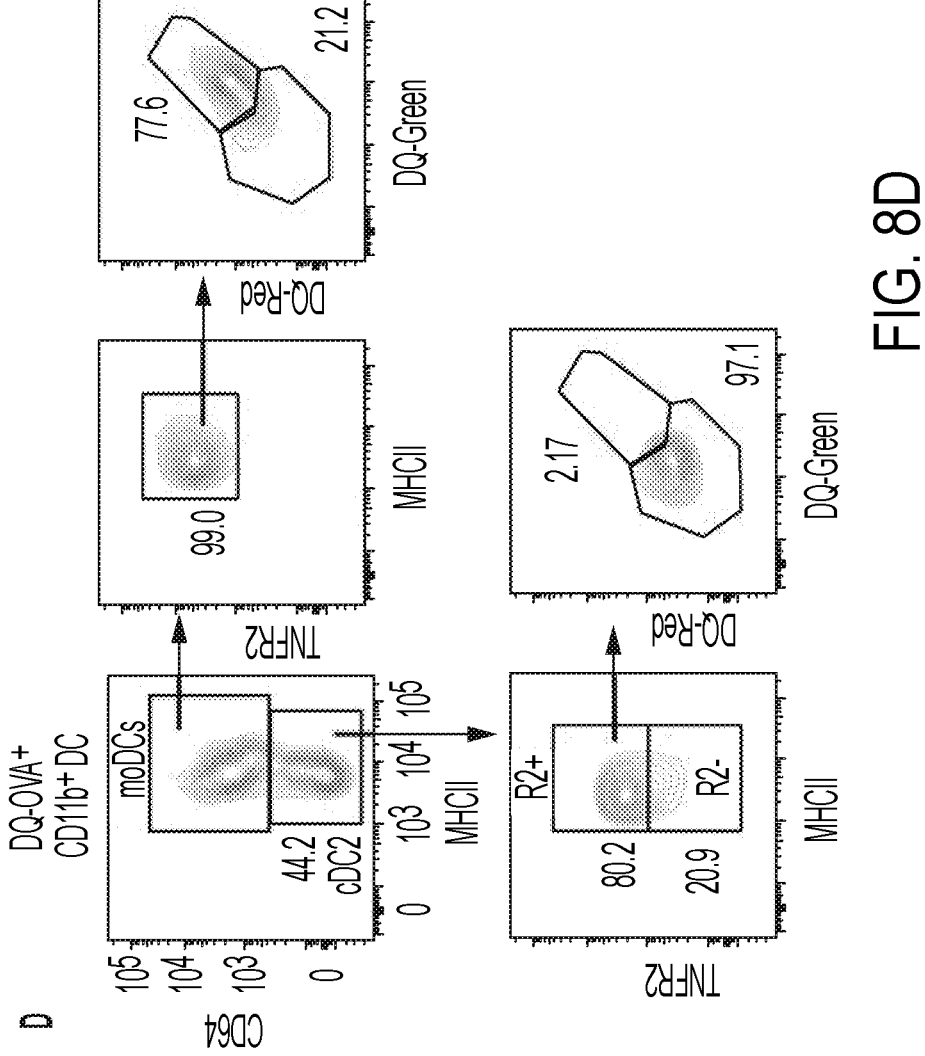
FIG. 8D

CDG differentially activates lung dendritic cells *in vivo*

FIG. 13B

Aged lung DCs fail to make TNF in response to cyclic di-GMP in vivo

FIG. 20

Aged lung moDCs are defective in response to CDG in vivo.

(IgG2A)Fc-TNF RESTORED MUCOSAL ANTIBODY RESPONSES IN THE AGED MICE
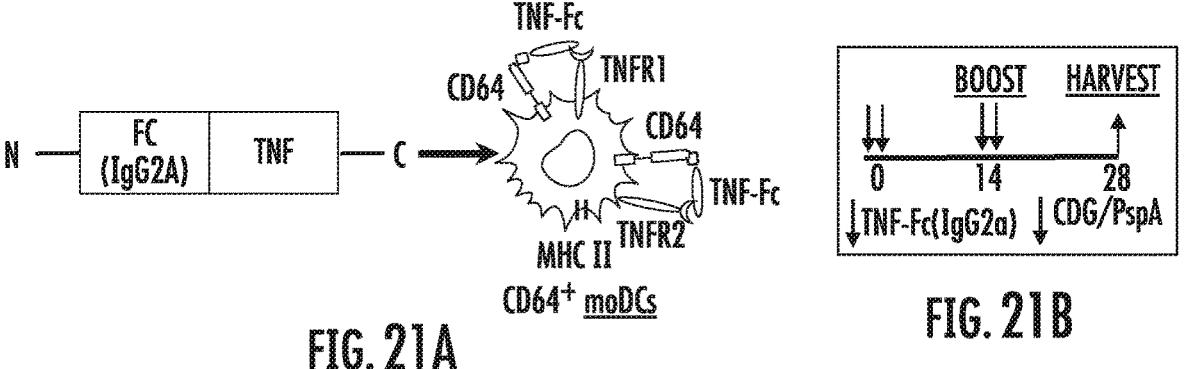
FIG. 21A
FIG. 21B
LUNG CD4+ T CELLS (14 DAYS POST IMMUNIZATION)
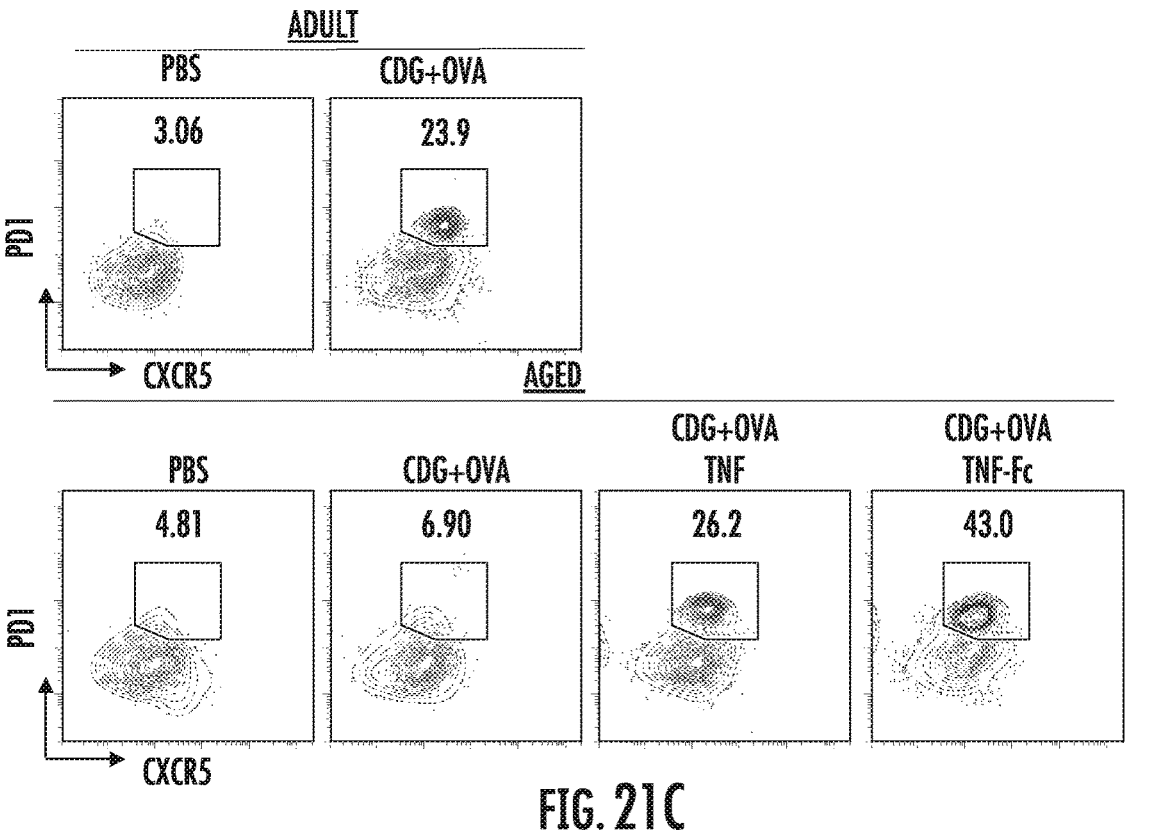
FIG. 21C

TARGETING TRANSMEMBRANE TNF OR SOLUBLE TNF TO CD64+ MODCS

MOUSE TNF SEQUENCE

|  10 | 20 | 30 | 40 | 50 |
|---|---|---|---|---|
| MSTESMIRDV | ELAEEALPQK | MGGFQNSRRC | LCLSLFSFLL | VAGATTLFCL |
| 60 | 70 | 80 | 90 | 100 |
| LNFGVIGPQR | DEKFPNGLPL | ISSMAQTLTL | RSSSQNSSDK | PVAHVVANHQ |
| 110 | 120 | 130 | 140 | 150 |
| VEEQLEWLSQ | RANALLANGM | DLKDNQLVVP | ADGLYLVYSQ | VLFKGQGCPD |
| 160 | 170 | 180 | 190 | 200 |
| YVLLTHTVSR | FAISYQEKVN | LLSAVKSPCP | KDTPEGAELK | PWYEPIYLGG |
| 210 | 220 | 230 | | |
| VFQLEKGDQL | SAEVNLPKYL | DFAESGQ VYF | GVIAL | |
| | | NFR | | |

1) TRANSMEMBRANE TNF-Fc

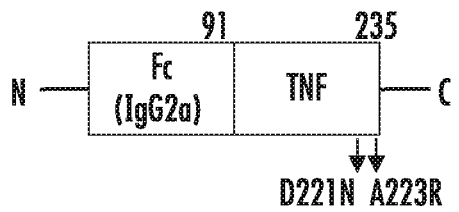

2) SOLUBLE TNF-Fc

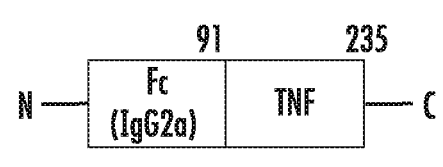

FIG. 23

Fig 7. A-B. C57BL/6J mice were immunized with Influenza nucleoprotein (NP)/TNF-Fc(IgG2A) or NP/TNF-Fc(IgG2A). Lung were analyzed on day 14 by Flow cytometry. n=3. CCL20 is a T cells recruiting chemokine and Bcl6 is a transcriptional factor important for memory cells development.

TARGETING MODC TO ENHANCE VACCINE EFFICACY ON MUCOSAL SURFACE

GOVERNMENT SUPPORT

This invention was made with government support under Grant Nos. AI110606, AI125999, AI132865 awarded by the National Institutes of Health. The government has certain rights in the invention.

BACKGROUND

Typically, pathogens enter the body via mucosal surfaces. Vaccination by mucosal routes is viewed to be more effective at inducing protective immunity against mucosal pathogens, and mucosal vaccines have the benefits of low cost and ease of administration. However, there are very few mucosal vaccines approved for use, which is largely due to problems with developing safe and effective mucosal adjuvants.

BRIEF DESCRIPTION OF THE DRAWINGS

The present invention is illustrated by way of example, and not by way of limitation, in the figures of the accompanying drawings.

FIG. 19.

Figure 20:
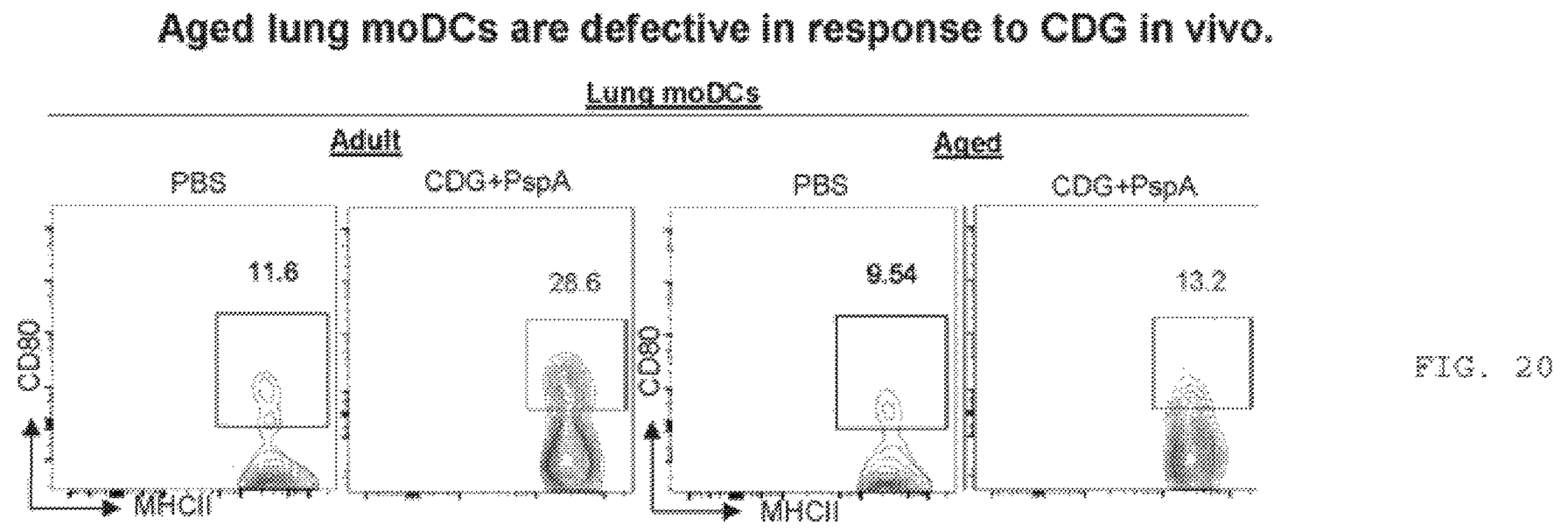

FIG. 20. 3-month old C57BL/6 (Adult),18-month old C57BL/6 (Aged) mice were immunized (i.n.) with CDG (5 µg)/PspA(2 µg) or PBS for 16 hrs. Lung moDCs (CD64+ CD11B+MHCIIhiCD11C+CD24−) activation were examined by Flow cytometry. n=3.

FIG. 21. FIG. 21A. A cartoon of TNF-Fc fusion protein and its proposed mode of action on moDCs. FIG. 21B. A cartoon of the CDG/PspA/TNF-Fc vaccine strategy. FIG. 21C. Lung Tfh cells(PD1+CXCR5+) cells were examined in adult and aged mice 14 days after immunization by Flow cytometry. n=3.

or anti-NP23 (low-affinity) IgG was examined in mice 1 month post immunization. n=3. Graphs represent means±standard error from three independent experiments.

FIG. 23 shows sequence information on Mouse TNF. There is a two amino acid modification (D221N, A223R) that causes TNF sequence to bind only to TNFR2. One skilled in the art would appreciate that similar strategies could be applied to human TNF sequence.

Figures 24A, 24B:
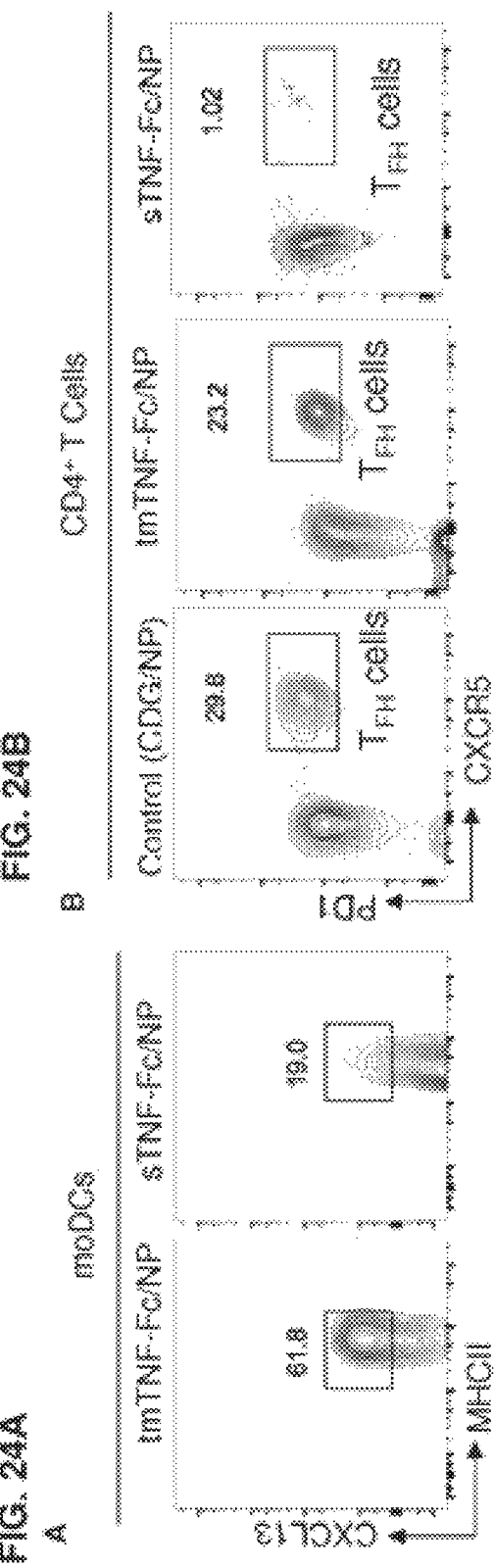

FIG. 24. C57BL/6J mice were immunized with Influenza nucleoprotein (NP)TNF-Fc(IgG2A) [sTNF-Fc] or NP/TNF$_{D221N/A223R}$-Fc(IgG2A) [tmTNF-Fc]. Lung moDCs (FIG. 24A) and T$_{FH}$ cells (FIG. 24B) were analyzed on day 14 by Flow cytometry. n=3. CXCL13 is a chemokine essential for the formation of germinal center.

Figures 25A, 25B:
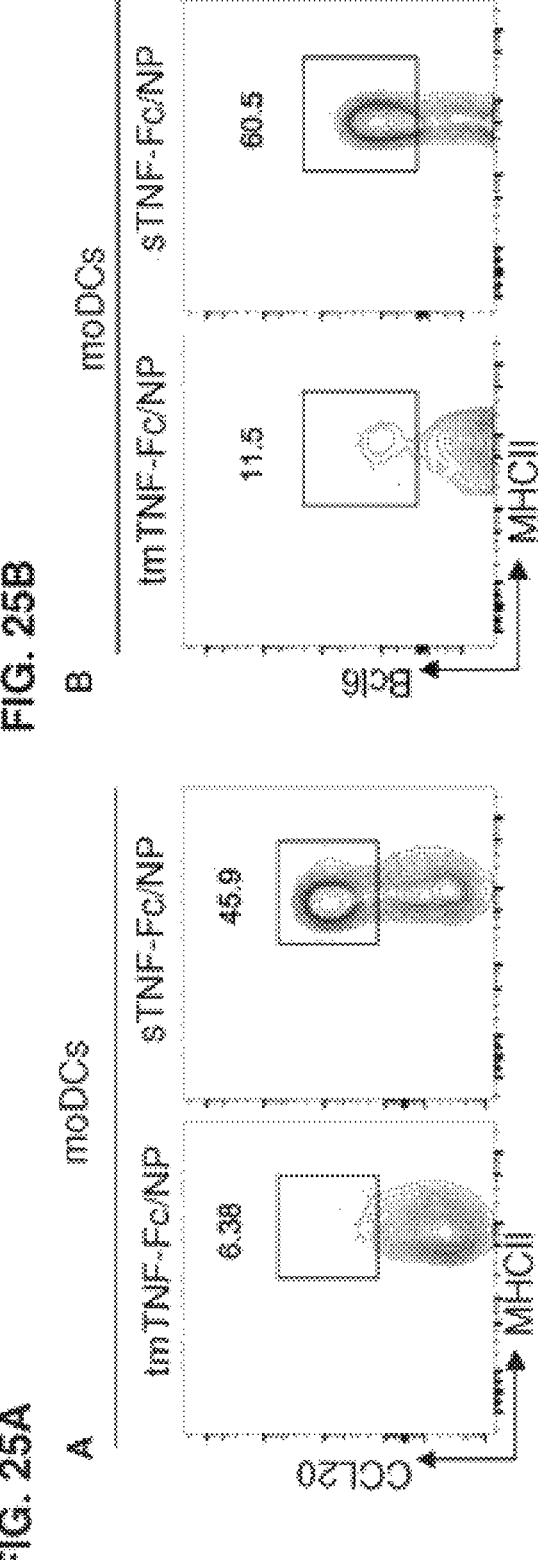

FIG. 25. A-B. C57BL/6J mice were immunized with Influenza nucleoprotein (NP)/TNF-Fc(IgG2A) [sTNF-Fc] or NP/TNF$_{D221N/A223R}$-Fc(IgG2A) [tmTNF-Fc]. Lung were analyzed on day 14 by Flow cytometry. n=3. CCL20 is a T cells recruiting chemokine (FIG. 25A) and Bcl6 (FIG. 25B) is a transcriptional factor important for memory cells development.

DETAILED DESCRIPTION

The present disclosure is based on the discovery of a new lung dendritic cell subset and its novel in vivo model of action that generates efficacious mucosal vaccine responses. The characterization of this new subset of dendritic cells along with its mode of action have allowed the design of vaccine compositions that are tailored to generate efficacious vaccine responses in lung mucosa. The new lung dendritic cells possess a unique marker profile, TNFR2$^-$ pRelB$^-$PD-L1$^-$ C$\underline{X}$3CR1$^+$ c$\underline{DC2}$ (C3D2).

According to one embodiment, provided is a vaccine composition that includes a therapeutically effective amount of an antigen; a CDN; soluble tumor necrosis factor (TNF); and a CD64 antibody or antibody fragment. In another embodiment, a TNF conjugated with an moDC targeting moiety is implemented in addition to or in place of TNF and/or the CD64 antibody or antibody fragment. The TNF conjugated with an moDC targeting moiety may include a TNF-Fc (IgG2A) or an anti-CD64 antibody conjugate (antibody-cytokine fusion protein such as anti-CD64-TNF). The CDN may include, but is not limited to, cyclic-di-GMP (CDG), cyclic-di-AMP (CDA), cyclic-di-IMP (CDI), cyclic-AMP-GMP (CDA/G), cyclic-AMP-IMP (CDA/I, and cyclic-GMP-IMP (CDG/I). In a specific embodiment, the CDN is CDG. In a specific embodiment, the CD64 antibody is monoclonal antibody.

According to another embodiment, provided is a method of eliciting an immune response in a subject that involves administering to the subject a vaccine composition as described herein. The vaccine composition is one that activates monocyte derived dendritic cells (moDCs), to induce lung mucosal antibody responses.

One unique advantage of the compositions described herein is that allow for the generation of effective vaccine responses on mucosal surface. They also allow for the generation of long-termed memory responses that is critical for vaccine-induced protection.

According to another embodiment, provided is a method of eliciting an immune response that involves administering an antigen; and co-administering a cyclic dinucleotide, soluble tumor necrosis factor (TNF); and a CD64 antibody or antibody fragment or, optionally, a TNF conjugated with an moDC targeting moiety (e.g. a TNF-Fc(IgG2A) or an anti-CD64 antibody conjugated-TNF) in addition to or in place of TNF or CD64 antibody or fragment, or both TNF and CD64 antibody or fragment. In this embodiment, the compositions are not necessarily administered in the same composition but may be administered separately, either by the same or different mode of administration.

Another embodiment pertains to a kit that includes an inhalative administration device and a therapeutically effective amount of a composition described herein. The kit may include a vaccine composition or a separate antigen composition and adjuvant composition. The one or more compositions may be loaded into the device or provided in a separate container for use in the device.

Another embodiment pertains to a method for treating, or preventing, a disease or condition in a subject. The method involves administering an antigen associated with the disease or condition; and co-administering a cyclic dinucleotide, soluble tumor necrosis factor (TNF); and a CD64 antibody or antibody fragment or, optionally, a TNF conjugated with an moDC targeting moiety (e.g. a TNF-Fc (IgG2A) or an anti-CD64 antibody conjugated-TNF) in addition to or in place of TNF or CD64 antibody or fragment, or both TNF and CD64 antibody or fragment. Examples of the disease or condition include cancer or an infection.

A further embodiment pertains to an adjuvant composition that includes a cyclic dinucleotide, soluble tumor necrosis factor (TNF); and a CD64 antibody or antibody fragment or, optionally, a TNF conjugated with an moDC targeting moiety (e.g. a TNF-Fc(IgG2A) or an anti-CD64 antibody conjugated-TNF) in addition to or in place of TNF or CD64 antibody or fragment, or both TNF and CD64 antibody or fragment. The adjuvant composition may optionally include a pharmaceutically acceptable carrier.

DEFINITIONS

Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described below. However, the skilled should understand that the methods and materials used and described are examples and may not be the only ones suitable for use in the invention. Moreover, it should also be understood that as measurements are subject to inherent variability, any temperature, weight, volume, time interval, pH, salinity, molarity or molality, range, concentration and any other measurements, quantities or numerical expressions given herein are intended to be approximate and not exact or critical figures unless expressly stated to the contrary. Hence, where appropriate to the invention and as understood by those of skill in the art, it is proper to describe the various aspects of the invention using approximate or relative terms and terms of degree commonly employed in patent applications, such as: so dimensioned, about, approximately, substantially, essentially, consisting essentially of, comprising, and effective amount.

Generally, nomenclature used in connection with, and techniques of, cell and tissue culture, molecular biology, immunology, microbiology, genetics, protein, and nucleic acid chemistry and hybridization described herein are those well-known and commonly used in the art. The methods and techniques of the present invention generally are performed according to conventional methods well known in the art and as described in various general and more specific references, unless otherwise indicated. See, e.g., Sambrook et al., Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lan, Antibodies: A Laboratory Manual, Cold Spring Harbor Laboratory Press, Cold Spring Harbor, N.Y. (1990); Kandel, Schwartz, and Jessell, eds., Principles of Neural Science, 4th ed., McGraw-Hill/Appleton & Lange: New York, N.Y. (2000). Unless defined otherwise, all technical and scientific terms used herein have the same meaning as commonly understood by one of ordinary skill in the art.

As used herein and in the appended claims, the singular forms "a," "an," and "the" include plural references unless the content clearly dictates otherwise.

The term "about" as used herein means approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20% up or down (higher or lower).

The term "TNF" as used herein refers to tumor necrosis factor. The TNF sequence used is typically that of the species being treated, that is, human TNF when used in inducing an immune response in humans. The term TNF, unless otherwise indicated, includes both soluble TNF and transmembrane TNF.

The terms "soluble TNF" or "sTNF" are used interchangeably herein to refer to the 17 KDa trimeric soluble cytokine form of tumor necrosis factor that is found in blood plasma, i.e., the form that circulates throughout the body and confers TNF with its potent endocrine function.

The terms "transmembrane TNF" or "tmTNF" or "mTNF" are used interchangeably herein to refer to transmembrane TNF. tmTNF binds to only TNFR2.

The term "antibody(ies)" or antibody refers to an immunoglobulin molecule which specifically binds with an antigen. Antibodies can be intact immunoglobulins derived from natural sources or from recombinant sources and can be immunoreactive portions of intact immunoglobulins. The term "antibody(ies)" includes whole antibodies of any isotype (e.g., IgG, IgA, IgM, IgE, etc.) or antibody fragments. Antibodies or antibody fragments include Fab fragments, a Fab' fragments, a heavy chain antibodies, single-domain antibodies (sdAb), variable domain of a heavy chain antibodies, VHH, Nanobodies, single-chain variable fragments (scFv), a tandem scFvs, a bispecific T-cell engagers (BITEs), a diabodies, single-chain diabodies, DARTs, triple bodies, or a nanoantibodies.

The term "moDC" targeting moiety, as used herein refers to a component associated with TNF that targets the TNF to moDC cells. In one example, the moDC targeting moiety is an anti-CD64 antibody or antibody fragment. In another example, the moDC targeting moiety is a fragment crystallizable region (Fc region) of an antibody. In a specific example, the Fc is an Fc of a mouse IgG2a isotype or a human IgG1, IgG3 isotype.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "cancer" or "tumor" as used herein means is intended to include any neoplastic growth in a patient, including an initial tumor and any metastases. The cancer can be of the liquid or solid tumor type. Liquid tumors include tumors of hematological origin (hematological cancer), including, e.g., myelomas (e.g., multiple myeloma), leukemias (e.g., Waldenstrom's syndrome, chronic lymphocytic leukemia, other leukemias), and lymphomas (e g, B-cell lymphomas, non-Hodgkins lymphoma). Solid tumors can originate in organs, and include cancers such as lung, breast, prostate, ovary, colon, kidney, and liver.

The term "cyclic dinucleotide" or "CDN" refer to secondary signaling molecules including cyclic-di-GMP (CDG), cyclic-di-AMP (CDA), cyclic-di-IMP (CDI), cyclic-AMP-GMP (CDA/G), cyclic-AMP-IMP (CDA/I, and cyclic-GMP-IMP (CDG/I). Typically, CDNs trigger interferon in a STING-dependent manner.

The term "specifically binds," is used herein in reference to the interaction of an antibody, a polypeptide, or a peptide with a second chemical species, to mean that the interaction is dependent upon the presence of a particular structure (e.g., an antigenic determinant, binding domain, or epitope) on the chemical species. For example, a ligand recognizes and binds to a specific receptor structure rather than to proteins generally. For example, an antibody recognizes and binds to a specific protein structure rather than to proteins generally.

The term "therapeutic" as used herein means a treatment and/or prophylaxis. A therapeutic effect is obtained by a diminution, suppression, remission, or eradication of a disease state.

The term "therapeutically effective amount" refers to the amount of the subject compound that will elicit the biological or clinical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

In the context of the present invention, the term "vaccine" refers to a substance that induces anti-cancer or anti-pathogen immunity or suppresses the cancer or the pathogen upon later introduction of the cancer or pathogen into the subject.

The term "antigen associated with a disease or condition" refers to an antigen that induces an immune response against abnormal cells (e.g. cancer cells or infected cells) or pathogen cells (e.g. microbes) in a subject.

The term "vaccine composition" refers to a composition that includes an antigen and one or more adjuvant component(s).

As used herein, the term "immune response" includes T cell mediated and/or B-cell mediated immune responses. Exemplary immune responses include T cell responses, e.g., cytokine production and cellular cytotoxicity, and B cell responses, e.g., antibody production. In addition, the term immune response includes immune responses that are indirectly affected by T cell activation, e.g., antibody production (humoral responses) and activation of cytokine responsive cells, e.g., macrophages Immune cells involved in the immune response include lymphocytes, such as B cells and T cells (CD4+, CD8+, Th1 and Th2 cells); antigen presenting cells (e.g., professional antigen presenting cells such as dendritic cells, macrophages, B lymphocytes, Langerhans cells, and non-professional antigen presenting cells such as keratinocytes, endothelial cells, astrocytes, fibroblasts, oligodendrocytes); natural killer cells; myeloid cells, such as macrophages, eosinophils, mast cells, basophils, and granulocytes. In a specific embodiment, an immune response involves activation of moDCs by a newly identified (TNFR2$^-$ pRelB$^-$PD-L1$^-$ CX3CR1$^+$ cDC2) described herein.

The terms "immunogen," "antigen" or "Ag," as used herein, is defined as a molecule that induces an immune response. This immune response may involve either antibody production, or the activation of specific immunologically-competent cells, or both. The skilled artisan will understand that any macromolecule, including virtually all proteins or peptides, can serve as an immunogen. Furthermore, immunogens can be derived from recombinant or genomic DNA. A skilled artisan will understand that any DNA, which comprises a nucleotide sequences or a partial nucleotide sequence encoding a protein that elicits an immune response therefore encodes an "immunogen" as that term is used herein. Furthermore, one skilled in the art will understand that an immunogen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an immunogen need not be encoded by a "gene" at all. It is readily apparent that an immunogen can be generated, synthesized or can be derived from a biological sample.

"Parenteral" administering or administration of a composition includes, e.g., subcutaneous (s.c.), intravenous (i.v.), intramuscular (i.m.), or intradermal (i.d.) injection or infusion techniques.

"Topical" administering or administration of a composition includes contacting a body surface of the subject, including the skin, the eye, or the mucosa, with the composition.

"Inhalative" administering or administration refers to delivery to the upper respiratory tract or lungs. In one example inhalative administration includes delivery via inhaling of a composition through the mouth and/or nose. Intranasal administration includes inhalative administration through the nose.

The term "co-administration" or "co-administering" as used herein refers to the administration of an active agent before, concurrently, or after the administration of another active agent such that the biological effects of either agents overlap. The combination of agents as taught herein can act synergistically to treat or prevent the various diseases, disorders or conditions described herein. Using this approach, one may be able to achieve therapeutic efficacy with lower dosages of each agent, thus reducing the potential for adverse side effects.

Overview

Adjuvants improve vaccine safety profiles and enhance, and shape, antigen-specific immune responses. Understanding the mode of action of adjuvants is key for the development of rationally designed modern vaccines. Recently, the small molecule cyclic dinucleotides (CDNs) have emerged as a group of promising vaccine adjuvants in preclinical and clinical trials[1]. CDNs include the bacterial second messengers cyclic di-GMP (CDG), cyclic di-AMP, 3'3'-cyclic GMP-AMP and the mammalian second messenger 2'3'-cyclic GMP-AMP[1]. CDG is the founding member and the most studied CDNs[2]. As a mucosal adjuvant, CDG does not cause acute toxicity in mice[1]. Furthermore CDG is a more potent activator of Th1 and Th2 immune response than LPS, CpG oligonucleotides (ODN) or aluminum salt based adjuvant in mice[3]. Last, CDG adjuvanted vaccines protect mice from H5N1 influenza[4], *Acinetobacter baumannii*[5], *Staphylococcus aureus*[6], *Klebsiella pneumoniae*[7] and *Streptococcus pneumoniae*[8, 9]. CDG also showed cancer vaccine adjuvant activity in animal models[10,11].

MPYS, also known as STING and MITA, is a receptor for CDNs[12] and a critical player in sensing cytosolic DNA[13,14]. MPYS[−/−] mice lose CDNs adjuvant activity[15]. Additionally, TNF signaling, not type I IFN signaling, is essential for the adjuvant activity of CDG in vivo[15,16] Notably, when administered intranasally, CDG not only induced lung production of TNF, IL-1β but also the anti-inflammatory cytokine IL-10[17]. Consequently, CDG adjuvant does not induce over-inflammatory responses in the lung[17]. The precise in vivo mechanism by which TNF mediates CDG adjuvant activity in vivo is unknown.

DCs orchestrate vaccine adjuvant responses[18]. They consist of developmentally and functionally distinct subsets that promote either immunogenic or tolerogenic immune responses[19-22]. Lungs have three DC subsets: the CD103+ conventional DC (cCD1), the CD11b+CD24+CD64− conventional DC (cDC2) and monocyte-derived CD11b+CD24−CD64+ DC (moDC)[21]. Using MPYS[fl/fl]CD11C[Cre] mice, we previously showed that CDG adjuvant activity depends on MPYS expression in DCs[17]. The lung DC subset mediating CDG adjuvant activity is unknown.

As disclosed herein, identified is a new subset of lung DC (TNFR2−pRelB−PD-L1−CX3CR1+ cDC2) mediating CDG adjuvant activity in vivo. Surprisingly, intranasally administered CDG induces the activation, not maturation, of this new TNFR2− cDC2 subset. Activated TNFR2− cDC2 expresses mTNF, which interacts with TNFR2 on moDC to drive moDC maturation promoting CDG adjuvant responses.

Compositions and Modes of Administration

In various embodiments, the methods of the present invention comprise administering an antigen, or a polynucleotide encoding an immunogen, and co-administering one or more adjuvant components, directly to a subject. In a specific embodiment, the one or more adjuvant components include a CDN, sTNF and/or CD64 antibody or antibody fragment. In another embodiment, adjuvant components include a CDN and a TNF conjugated with an moDC targeting moiety (e.g. a TNF-Fc(IgG2A) or an anti-CD64 antibody conjugated-TNF). Administration of the antigen and one or more adjuvant components can comprise, for example, inhalative, intramuscular, intravenous, peritoneal, subcutaneous, and intradermal administration. In a specific example, the antigen and adjuvant component(s) are administered concurrently. In an even more specific example, the antigen and adjuvant component(s) are administered in the same composition.

Furthermore, the actual dose and schedule can vary depending on whether the antigen and adjuvant component(s) are administered in combination with other pharmaceutical compositions, or depending on inter-individual differences in pharmacokinetics, drug disposition, and metabolism. One skilled in the art can easily make any necessary adjustments in accordance with the exigencies of the particular situation.

These methods described herein are by no means all-inclusive, and further methods to suit the specific application will be apparent to the ordinary skilled artisan. Moreover, the effective amount of the antigen and adjuvant component(s) can be further approximated through analogy to compounds known to exert the desired effect.

Administration of the antigen and adjuvant component(s) may be continuous or intermittent, depending, for example, upon the recipient's physiological condition, whether the purpose of the administration is therapeutic or prophylactic, and other factors known to skilled practitioners. The administration of the antigen and adjuvant component(s) may be essentially continuous over a preselected period of time or may be in a series of spaced doses. Both local and systemic administration is contemplated. The amount administered will vary depending on various factors including, but not limited to, the composition chosen, the particular disease, the weight, the physical condition, and the age of the subject, and whether prevention or treatment is to be achieved. Such factors can be readily determined by the clinician employing animal models or other test systems which are well known to the art.

When the antigen and adjuvant component(s) are prepared for administration, they may be combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" carrier, diluent, excipient, and/or salt is one that is compatible with the other ingredients of the formulation, and not deleterious to the recipient thereof. The active ingredient for administration may be present as a powder, as granules, as a solution, as a suspension or as an emulsion.

Pharmaceutical formulations containing the antigen and/or adjuvant component(s) can be prepared by procedures known in the art using well known and readily available ingredients. The antigen and adjuvant component(s) can also be formulated as solutions appropriate for inhalative administration or parenteral administration, for instance by intramuscular, subcutaneous, intradermal or intravenous routes.

The pharmaceutical formulations of antigen and adjuvant component(s) can also take the form of an aqueous or anhydrous solution or dispersion, or alternatively the form of an emulsion or suspension.

Thus, for parenteral administration (e.g., by injection, for example, bolus injection or continuous infusion) the formulations may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

Devices for intranasal administration include spray devices. Suitable nasal spray devices are commercially available from Becton Dickinson, Pfeiffer GMBH and Valois. Spray devices for intranasal use do not depend for their performance on the pressure applied by the user. Pressure threshold devices are particularly useful since liquid is released from the nozzle only when a threshold pressure is attained. These devices make it easier to achieve a spray with a regular droplet size. Pressure threshold devices suitable for use with the present invention are known in the art and are described for example in WO 91/13281 and EP 311 863 B. Such devices are currently available from Pfeiffer GmbH and are also described in Bommer, R. Advances in Nasal drug delivery Technology, Pharmaceutical Technology Europe, September 1999, p 26-33.

In one specific example, intranasal devices produce droplets (measured using water as the liquid) in the range 1 to 500 μm. Below 10 μm there is a risk of inhalation, therefore it is desirable to have no more than about 5% of droplets below 10 μm.

Bi-dose delivery may also be implemented for intranasal delivery. Bi-dose devices contain two subdoses of a single vaccine dose, one sub-dose for administration to each nostril.

The invention provides in a further aspect a pharmaceutical kit comprising an intranasal administration device containing a vaccine formulation or comprising an intranasal administration device and a separate vaccine formulation(s) for use with that device.

It will be appreciated that the unit content of active ingredient or ingredients contained in an individual dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions, such as phosphate buffered saline solutions pH 7.0-8.0.

Therapeutic Uses

Certain embodiment pertain to methods of preventing, inhibiting, and treating cancer or infection. In one embodiment, the vaccination methods of the invention induce protective immunity against cancer or a pathogen, by generating an immune response directed against the cancer or the pathogen. In one embodiment, the methods of the invention induce production of pathogen-specific antibodies. In another embodiment, the methods of the invention induce a pathogen-specific cell-mediated immune response. In another embodiment, the methods of the invention induce production of pathogen-specific antibodies and a pathogen-specific cell-mediated immune response. In one embodiment, the methods of the invention induce production of tumor-specific antibodies. In another embodiment, the methods of the invention induce a tumor-specific cell-mediated immune response. In another embodiment, the methods of the invention induce production of tumor-specific antibodies and a tumor-specific cell-mediated immune response.

Anti-cancer and anti-pathogen immunity can be induced by administering an antigen and adjuvant component(s) described herein, and the induction of anti-cancer or anti-pathogen immunity enables treatment and prevention of a disease associated with cancer or the presence of the pathogen. A decrease in mortality of individuals having a disease, a decrease of the disease markers in the blood, alleviation of detectable symptoms accompanying the disease and such are also included in the therapy or prevention of the disease associated with cancer or infection by the pathogen. Such therapeutic and preventive effects are preferably statistically significant, for example, observed at a significance level of 5% or less, wherein the therapeutic or preventive effect of a vaccine against a disease, is compared to a control without vaccine administration. For example, Student's t-test, the Mann-Whitney U-test or ANOVA may be used for determining statistical significance.

Certain embodiments provide a method for treating, or preventing, a disease or condition associated cancer or infection by a pathogen. The antigen and adjuvant(s) and methods of administering same may be administered prophylactically or therapeutically to subjects suffering from, or at risk of, or susceptible to, developing the disease or condition, including cancer or infection by a pathogen. Such subjects may be identified using standard clinical methods. In the context of the present invention, prophylactic administration occurs prior to the manifestation of overt clinical symptoms of disease, such that a disease or disorder is prevented or alternatively delayed in its progression. In the context of the field of medicine, the term "prevent" encompasses any activity which reduces the burden of mortality or morbidity from disease. Prevention can occur at primary, secondary and tertiary prevention levels. While primary prevention avoids the development of a disease, secondary and tertiary levels of prevention encompass activities aimed at preventing the progression of a disease and the emergence of symptoms as well as reducing the negative impact of an already established disease by restoring function and reducing disease-related complications.

The induction of anti-cancer or anti-pathogen immunity by composition embodiments described herein, can be further confirmed by observing the induction of antibody production against specific immunogens. For example, when antibodies against one or more antigens, are induced in a subject immunized with the antigen containing composition, and when pathology is suppressed by those antibodies, the one or more antigens, are determined to induce anti-cancer or anti-pathogen immunity.

Antigens

Those skilled in the art will appreciate that known antigens or developed antigens may be co-administered with adjuvant component(s) described herein. Examples of antigens include but are not limited to the following:

| Source | Antigens |
| --- | --- |
| BeiResource | H7 Hemagglutinin (HA) Protein from Influenza Virus, A/Netherlands/219/2003 (H7N7), Recombinant from Baculovirus |
| BeiResource | *Streptococcus pneumoniae* Family 1, Clade 2 Pneumococcal Surface Protein A (PspA UAB055) with C-Terminal Histidine Tag, Recombinant from *Escherichia coli* |

-continued

| Source | Antigens |
|---|---|
| BeiResource | Anthrax Protective Antigen (PA), Recombinant from *Escherichia coli* |
| NIH AIDS Reagent Program | HIV-1 Env V1 V2 Recombinant Protein |
| NIH AIDS Reagent Program | HIV-1$_{IIIB}$ pr55 Gag |

It is noted that the vaccine formulation can include multiple antigens. For example, one formulation can include CDG+ PspA+H7/HA to protect infection from both Influenza and pneumococcal infection in one immunization.

EXAMPLES

CDG Directly Targets Lung cDC1 and cDC2, not moDCs.

Figures 1A, 1B, 1C, 1D:
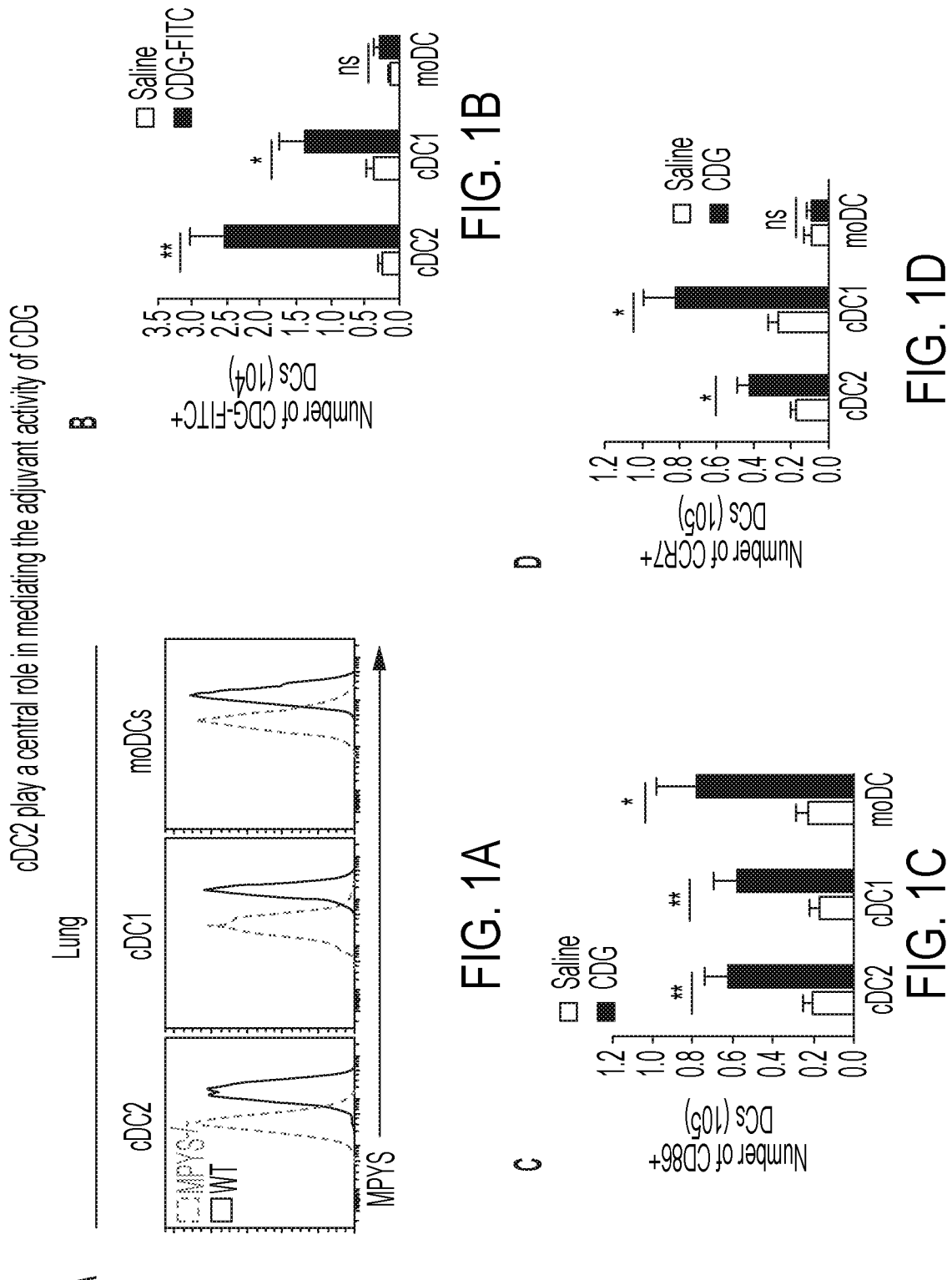
FIG. 1. cDC2 play a central role in mediating the adjuvant activity of CDG. A. Flow cytometry analysis of MPYS expression in lung DC subsets. n>3. B. Absolute number of lung DC subsets in C57BL/6 mice administered (i.n.) with saline or 5 µg FITC-CDG for 5 hours. n=3. C. Absolute number of CD86$^+$ lung DC subsets in mice administered (i.n.) with saline or 5 µg CDG for 16 hours. n>3. D. Absolute number of CCR7$^+$ lung DC subsets in mice administered (i.n.) with saline or 5 µg CDG for 16 hours. n>3. E-G. Flow cytometry analysis of pRelA and pRelB in cDC1 (E), cDC2 (F), and moDCs (G) from mice treated with saline or CDG for 16 hrs. n>3. H. C57BL/6, Batf3$^{-/-}$, and IRF4$^{fl/fl}$CD11c$^{cre}$ mice were immunized (i.n.) with two doses (14 days apart) of PspA or PspA plus CDG (5 ug). Anti-PspA IgG in serum and IgA in BALF were determined by ELISA. n>3. I. IRF4$^{fl/fl}$CD11c$^{cre}$ mice were adoptively transferred (i.n.) with lung cDC2 sorted from WT mice lung and immunized (i.n.) with PspA or CDG/PspA. Serum anti-PspA IgG and BALF IgA were determined by ELISA. n=3. Graphs represent means±standard error from three independent experiments. The significance is represented by and asterisk (*) where p<0.05 (unpaired Student's t test).
Figures 10A, 10B:
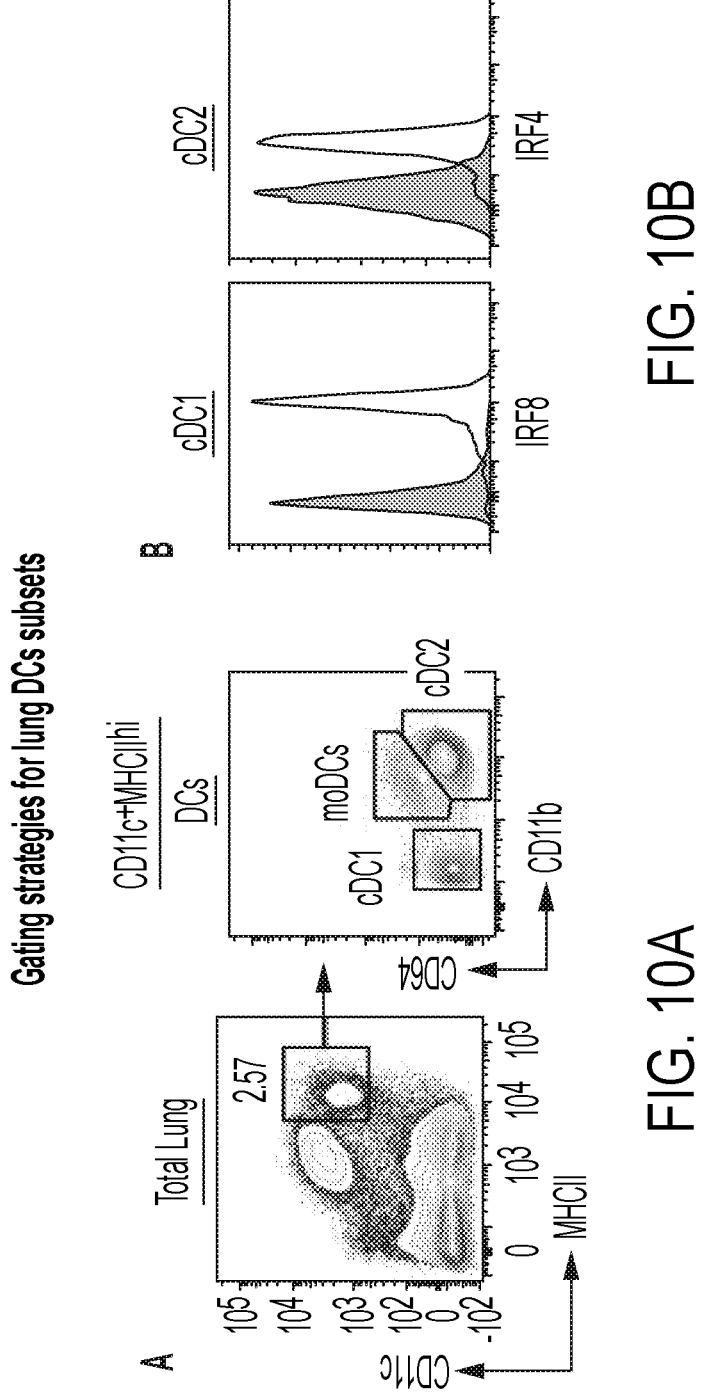
FIG. 10 A-B. Gating strategy for lung DCs. cDC1 are CD11c+MHCII$_{hi}$CD103$_+$CD11b$_-$ CD64_IRF8$_+$, cDC2 are CD11c$_+$MHCII$_{hi}$CD11b$_+$CD64_IRF4$_+$, moDCs are CD11c$_+$ MHCII$_{hi}$CD11b$_+$CD64$_+$. n>3. C. Flow cytometry analysis of lung DCs subsets in IRF4$_{fl/fl}$ and IRF4m$_{fl/fl}$CD11c$_{cre}$ mice including the total number of DCs. n=3. D. Flow cytometry analysis of lung DCs subsets in C57BL/6 (WT) and Batf3$_{-/-}$ mice including the total number of DCs. n=3. Graphs represent means±standard error from three independent experiments. The significance is represented by and asterisk (*) where p<0.05 (unpaired Student's t test).

DCs mediate CDG adjuvant activity in vivo 17. There are three lung DC subsets: cDC1 (CD103+CD24+ CD64− CD11b−), cDC2 (CD103−CD24+CD64−CD11b+) and moDC (CD103−CD24−CD64+CD11b+) 21, 23-27 (FIG. 10). All DC subsets express the CDG receptor MPYS, which is an ER-resident protein (FIG. 1A). CDG has two phosphate groups preventing it from directly passing through the cell membrane. To determine which lung DC subset took up CDG, mice were intranasally administered with FITC-conjugated CDG and FITC+ lung cells were examined after 5 hrs. Among lung DCs, cDC1 and cDC2 had the highest percentage of CDG-FITC whereas moDCs had no CDG-FITC (FIG. 1B). We concluded that intranasal administration of CDG directly targets lung cDC1 and cDC2, not moDCs.

Alveolar Macrophages (AM) Take Up CDG but are Dispensable for CDG Adjuvant Activity.

Figures 11A, 11B:
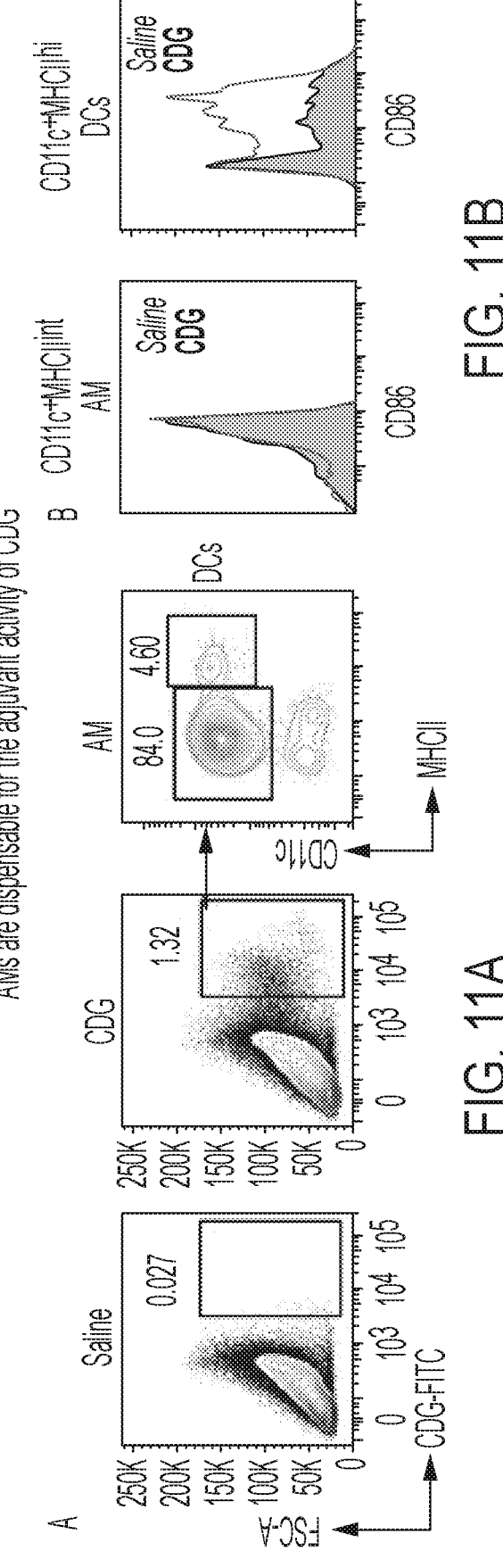
FIG. 11 A WT mice were intranasally administered with saline or 5 μg FITC-CDG for 5 hours. Lung FITC positive cells were analyzed by Flow cytometry. n>3. B. CD86 expression on CD11c+MHCIIint Alveolar macrophages (AMs) and lung DCs (CD11c+MHCIIhi) in WT mice treated (i.n.) with saline or 5 μg CDG for 16 hours. n=3. C. Flow cytometry analysis of MPYS expression in AMs (SiglecF+ CD11c+) from MPYSfl/flLysMcre mice. n=3. D. Absolute number of CD86$^+$ lung DC subsets in WT and MPYSfl/ flLysMcre mice administered (i.n.) with saline or 5 μg CDG for 16 hours. n=3. E. MPYS-/-, MPYSfl/fl, MPYSfl/flLy-sMcre, and MPYSfl/flCD11ccre mice were immunized (i.n.) with two doses (14 days apart) of PspA or PspA plus CDG (5 ug). Anti-PspA Abs in serum were determined by ELISA. n=3. Graphs represent means±standard error from three independent experiments. The significance is represented by and asterisk (*) where p<0.05 (unpaired Student's t test).
Figures 11C, 11D, 11E:
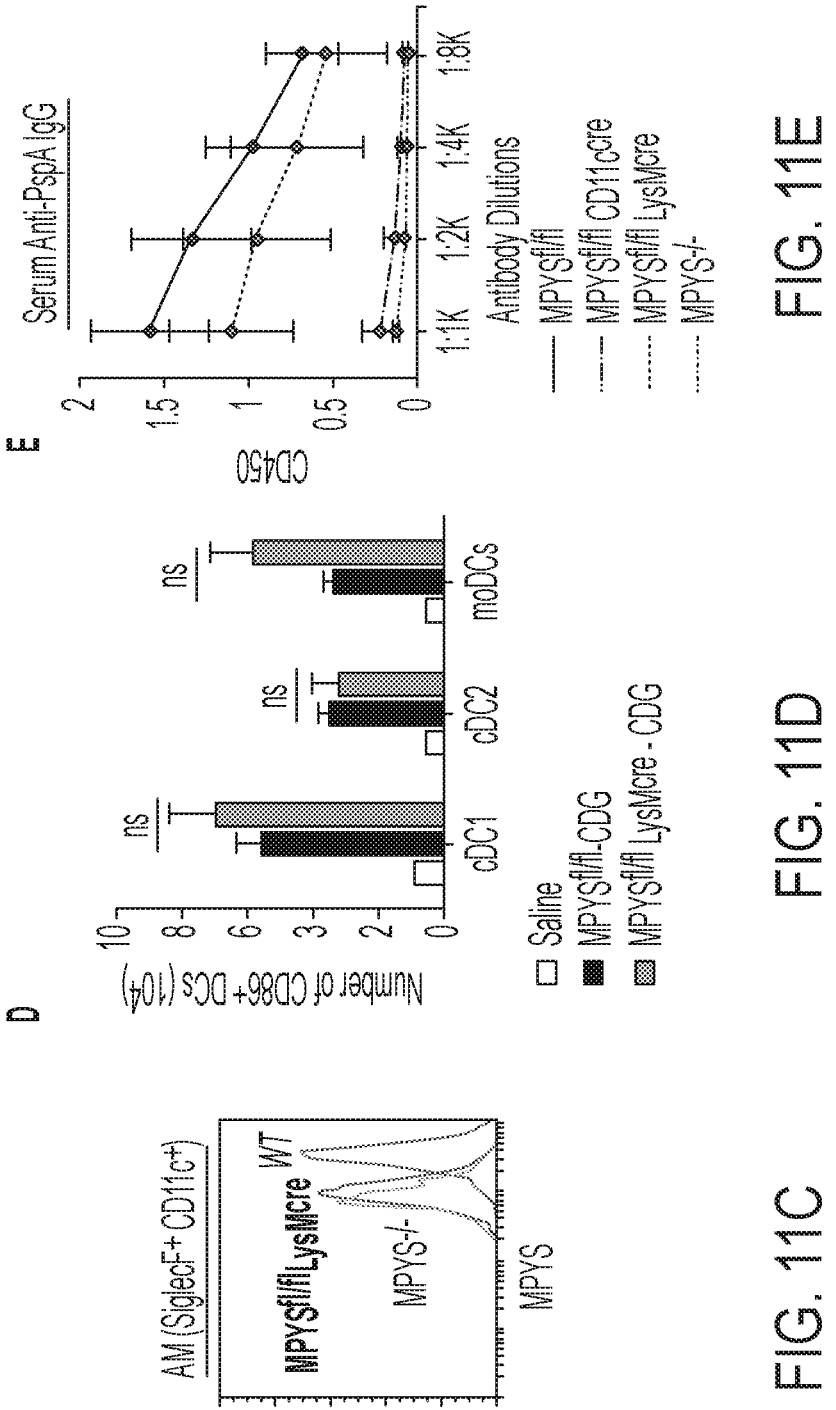

AM (CD11c$^+$MHC II$^{int}$) took up most of the fluorescent CDG in vivo (FIG. 11A). Unlike DCs, AM did not increase expression of CD86 following CDG treatment (FIG. 11B). To determine whether AM are required for CDG responses in vivo, we used the MPYS$^{fl/fl}$LysM$^{cre}$ mice[17], which deleted MPYS expression in AM (FIG. 11C). The activation of lung DCs by CDG was unaltered in the MPYS$^{fl/fl}$LysM$^{cre}$ mice (FIG. 11D). Importantly, MPYS$^{fl/fl}$LysM$^{cre}$ mice produced similar anti-pneumococcal surface protein A (PspA) antibody as the WT upon CDG/PspA immunization (FIG. 11E). We concluded that CDG targets AM but AM are dispensable for CDG adjuvant activity.

CDG Differentially Activates Lung DC Subsets In Vivo.

Figures 1E, 1F, 1G:
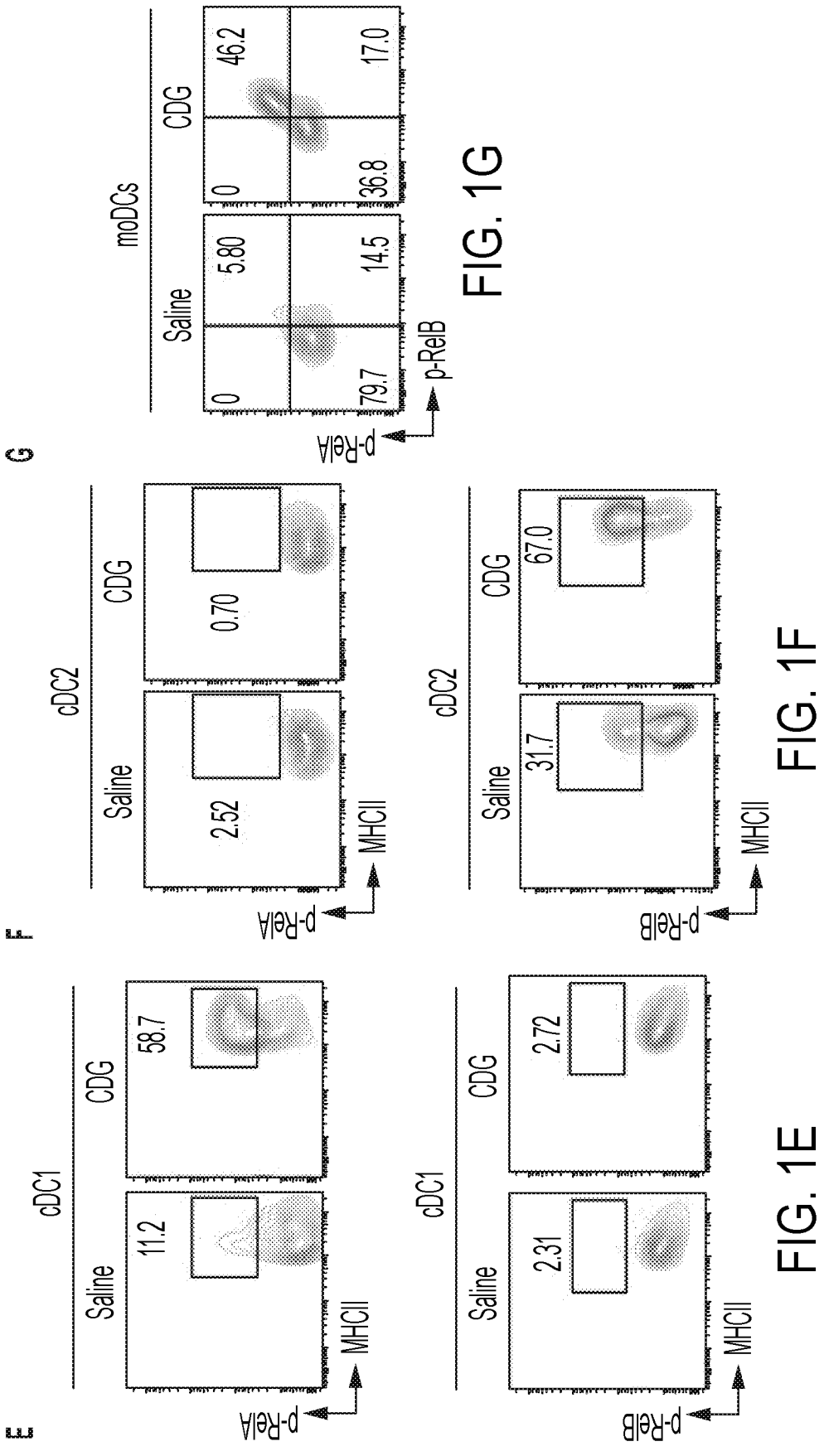
Figures 12A, 12B:
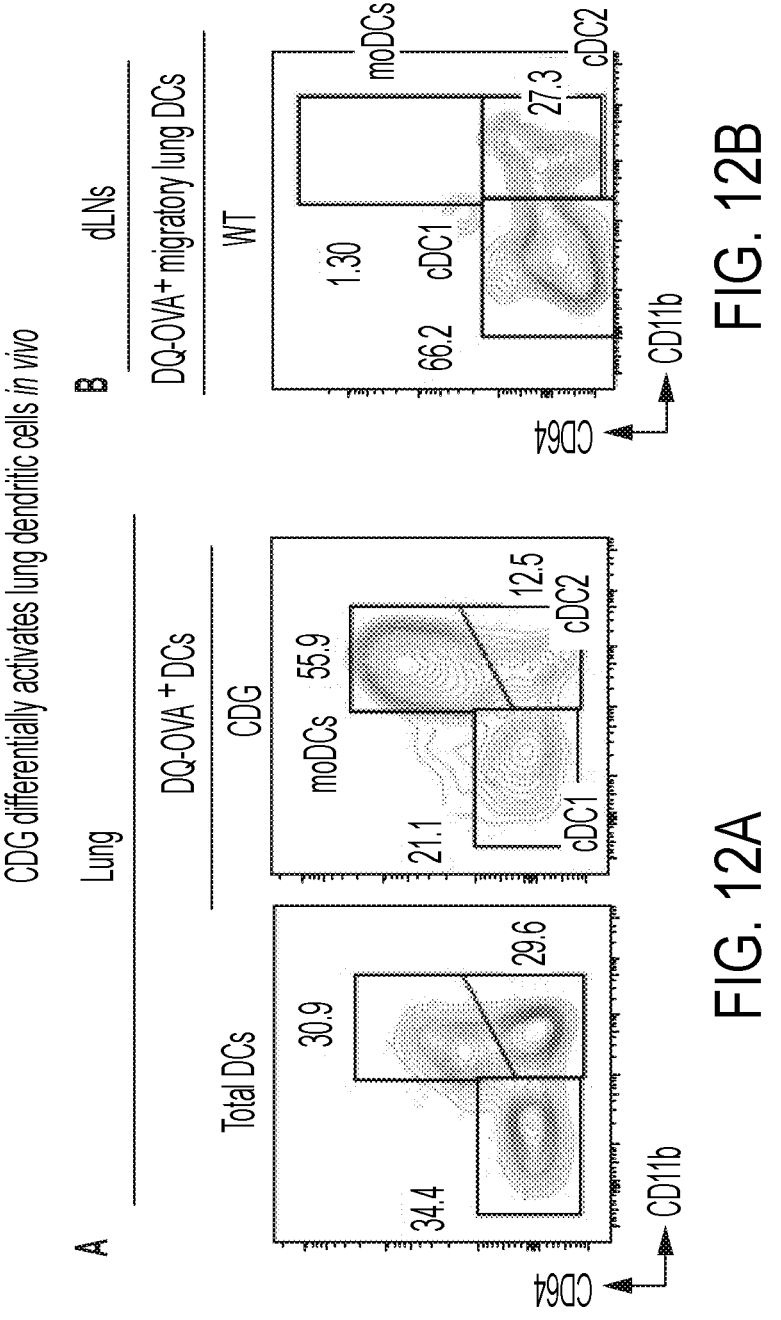
FIG. 12. A-B. Flow cytometry analysis of antigen uptake and processing in DCs from the lungs (A) and dLNs (B) of WT mice treated (i.n.) with DQ-OVA (20 ug) and CDG (5 ug) for 16 hours. n=3. C. Indicated mice were treated (i.n.) with saline or CDG for 5 hrs. Lung MCP-1, TNF, IL-1β and IL12p70 production were measured by ELISA in lung homogenates. n>3. DE.WT, Batf3-/-, and IRF4fl/ flCD11ccre mice were immunized (i.n.) with two doses (14 days apart) of PspA or PspA plus CDG (5 ug). Anti-PspA IgG1 (D)and IgG2c (E)in serum and BALF were determined by ELISA. n>3. EF. Splenocytes (F) or lung cells (G) from immunized WT, Batf3-/-, and IRF4fl/flCD11ccre mice were stimulated with 5 μg/ml PspA for 4 days in culture. Cytokines were measured in the supernatant by ELISA. n>3. Graphs represent means±standard error from three independent experiments. The significance is represented by and asterisk (*) where p<0.05 (unpaired Student's t test).

DCs subsets are functionally distinct. CDG increased CD86 and CCR7 expression in lung cDC1 and cDC2 (FIGS. 1C & 1D)[17]. In addition, both cDCs migrate, bearing processed antigen, to the lung draining lymph nodes (dLNs) (FIG. 12A-B). However, we found that following intranasal CDG administration, cDC1 activated RelA (FIG. 1E) while cDC2 activated RelB (FIG. 1F). Notably, some cDC2 have constitutively activated RelB (FIG. 1F). To further demonstrate that CDG differentially activates lung DC subsets, we used the IRF4$^{fl/fl}$CD11c$^{cre}$ and Batf3$^{−/−}$ mice.

Figure 12C:
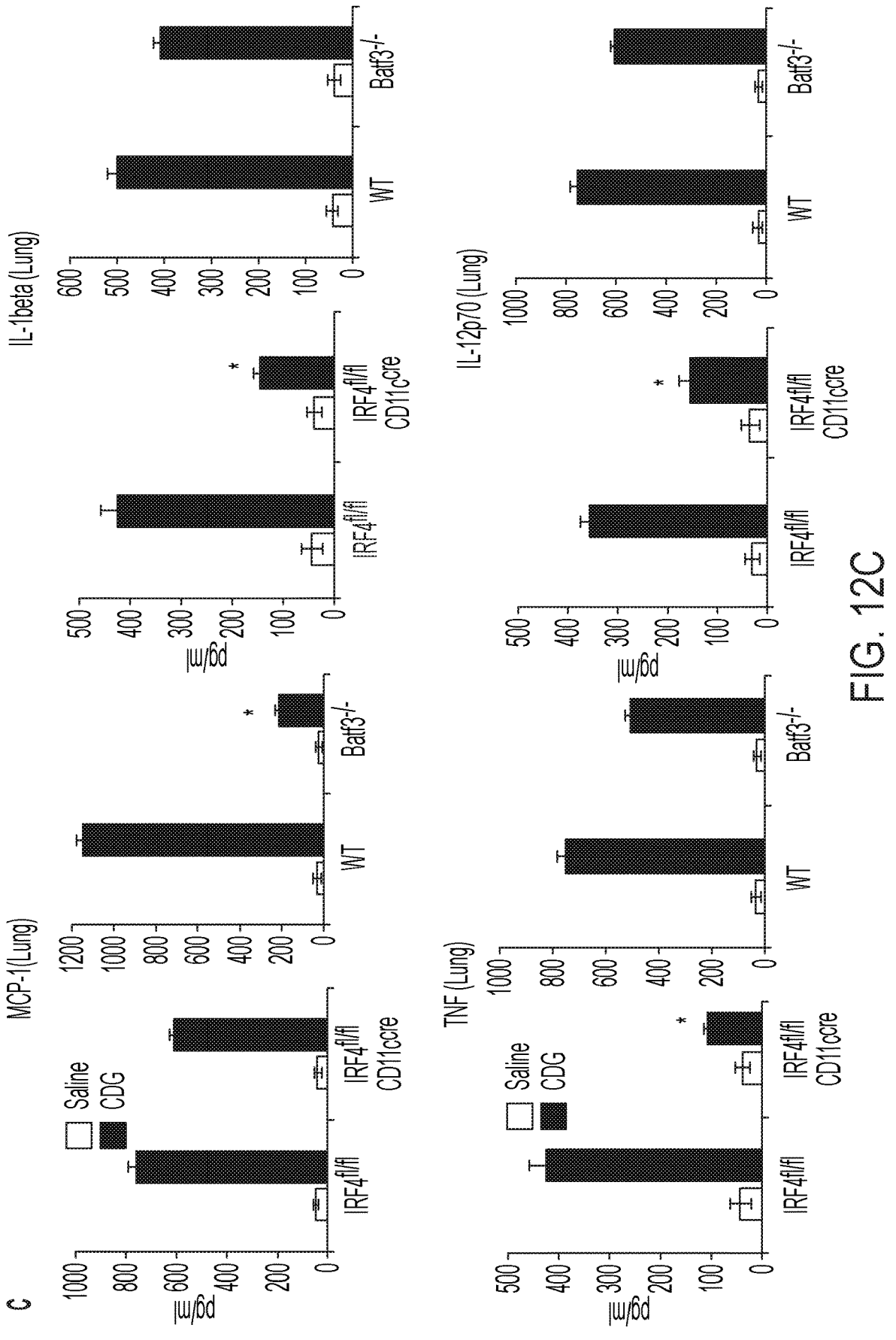

The development of cDC1 and cDC2 are controlled by transcriptional factors Batf3 and IRF4 respectively. IRF4$^{fl/fl}$CD11c$^{cre}$ mice lack cDC2 in the lung (FIG. 10C)[28-30] while Batf3$^{−/−}$ mice lack cDC1 (FIG. 10D)[31, 32]. We found that CDG-induced lung production of TNF, IL-1β and IL-12p70 were dramatically reduced in IRF4$^{fl/fl}$CD11c$^{cre}$ mice but not in the Batf3$^{−/−}$ mice (FIG. 12C). Conversely, CDG-induced MCP-1 production was largely absent in the Batf3$^{−/−}$ mice but not in the IRF4$^{fl/fl}$CD11c$^{cre}$ mice (FIG. 12C). We concluded that intranasally administered CDG differentially activates lung cDC1 and cDC2 in vivo.

CDG Indirectly Activates moDCs

Although moDCs did not take up CDG, they increased expression of CD86 in response to intranasal administration of CDG (FIG. 1C). This was independent of MPYS expression in moDCs as moDCs in MPYS$^{fl/fl}$LysM$^{cre}$ mice had normal levels of CD86 expression (FIG. 11D). Notably, activated moDCs did not increase CCR7 (FIG. 1D) and did not migrate to dLNs (FIG. 12B). Last, moDCs activated both RelA and RelB in response to CDG (FIG. 1G). We concluded that CDG indirectly activate moDCs and activated lung moDCs were not migratory[25, 33].

cDC2 Play a Central Role in Mediating CDG Adjuvant Activity

Figures 10C, 10D:
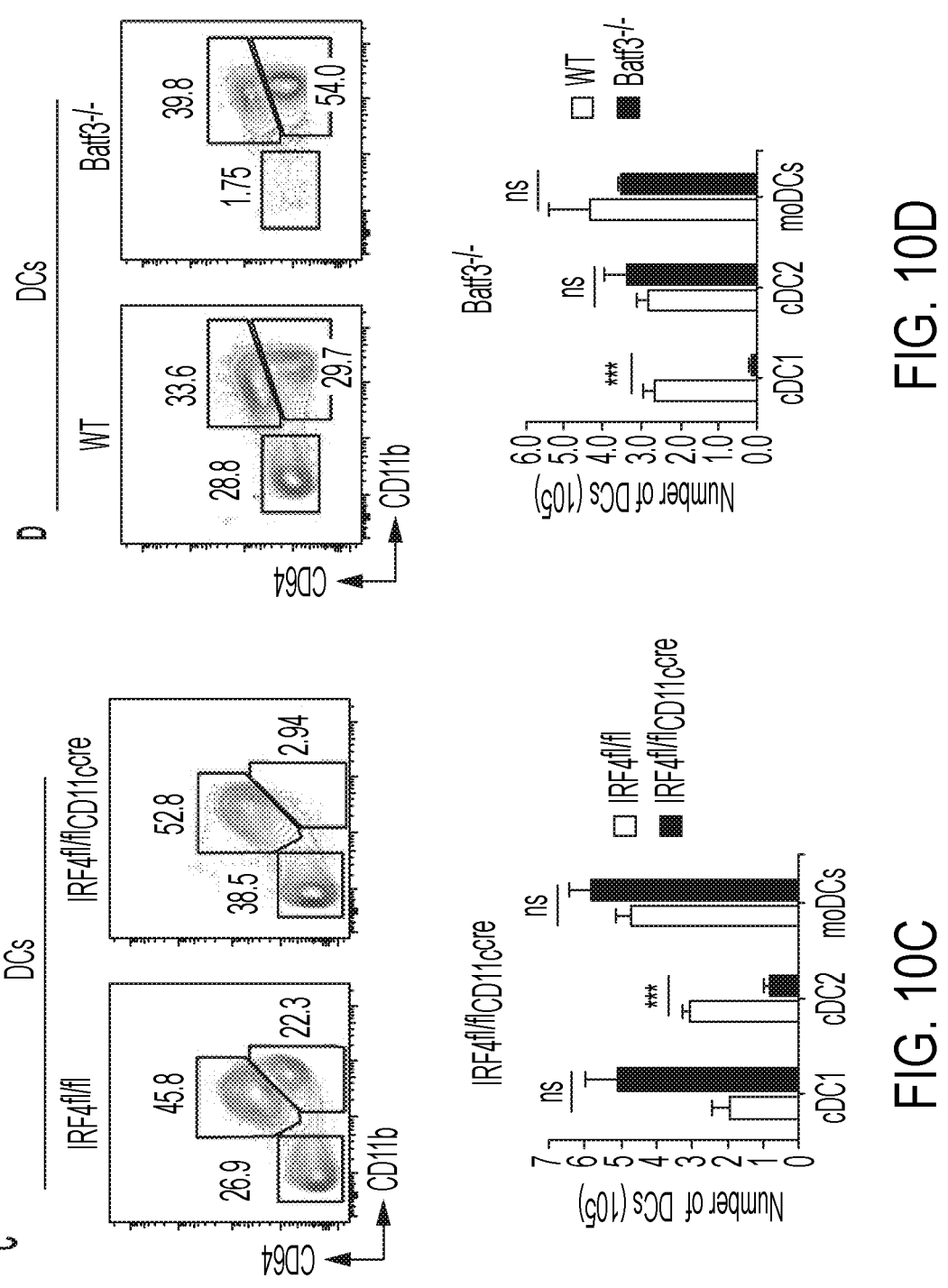

We next asked which cDC subset mediates CDG adjuvant activity. IRF4$^{fl/fl}$CD11c$^{cre}$ mice lack cDC2 in the lung[28,29] (FIG. 10C). The cDC1 and moDCs were retained in the IRF4$^{fl/fl}$CD11c$^{cre}$ mice (FIG. 10C). We examined CDG adjuvant activity in the IRF4$^{fl/fl}$CD11c$^{cre}$ mice. Mice were intranasally administered with PspA alone or with CDG. PspA-specific Ab responses were examined in the blood and bronchoalveolar lavage fluid (BALF). Unlike the WT mice, CDG did not induce anti-PspA Abs in BALF and serum (FIGS. 1H, 12D-E) from immunized IRF4$^{fl/fl}$CD11c$^{cre}$ mice. Ex vivo recall assay in lung cells and splenocytes from immunized IRF4$^{fl/fl}$CD11c$^{cre}$ mice also did not show PspA-specific Th1, Th2 or Th17 responses (FIG. 12F-G).

Figures 1H, 1I:
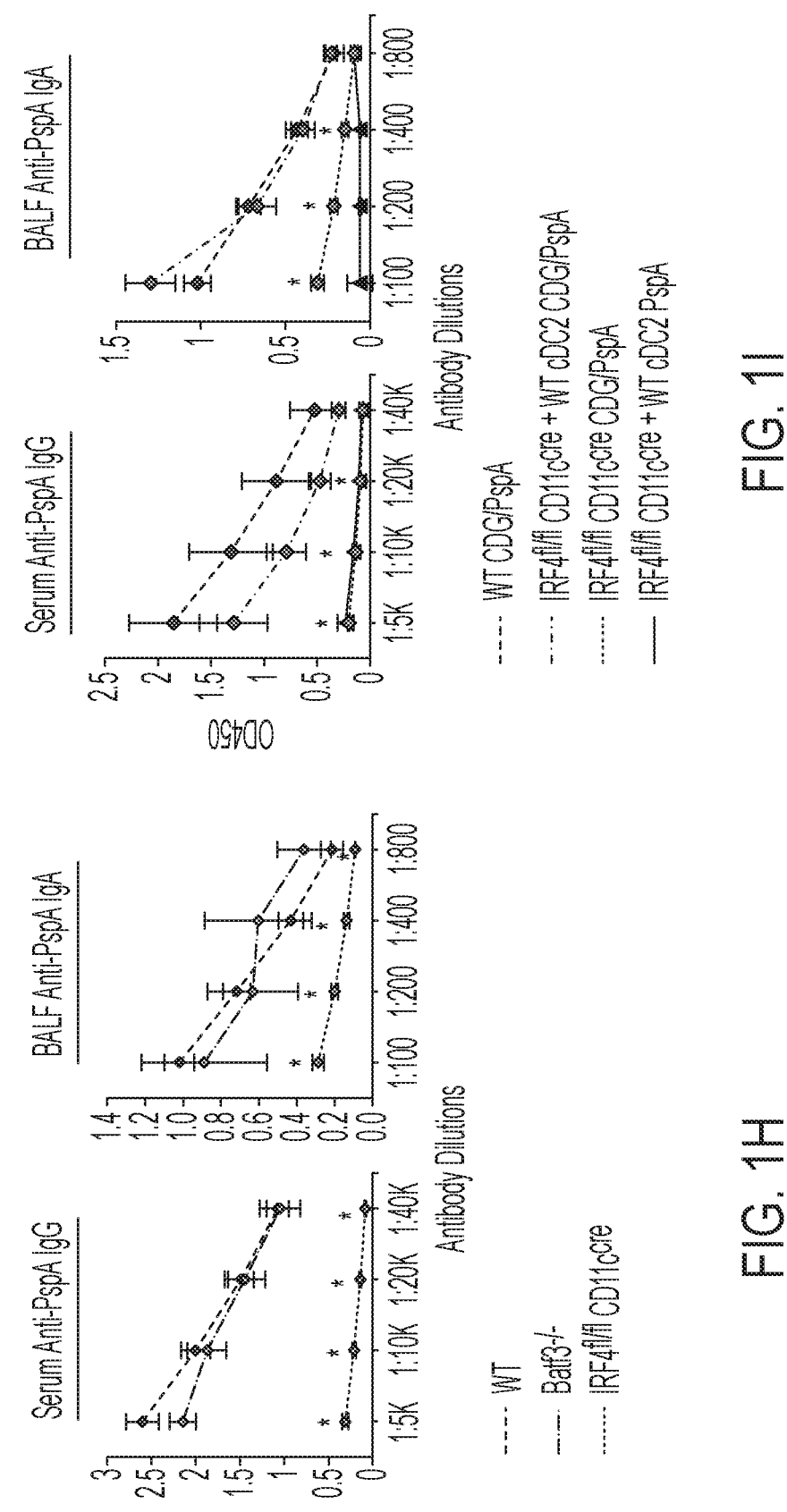

To further demonstrate that lung cDC2 mediate the adjuvant activity of CDG, we adoptively transfer (i.n.) WT lung cDC2 into IRF4$^{fl/fl}$CD11c$^{cre}$ mice. The recipient IRF4$^{fl/fl}$CD11c$^{cre}$ mice were then immunized with CDG/ PspA. We found that adoptive transfer of WT cDC2 generated PspA-specific serum IgG and IgA in the IRF4$^{fl/fl}$CD11c$^{cre}$ mice similar to the WT mice (FIG. 1I). We concluded that lung cDC2 are critical for CDG adjuvant activity.

Figures 12D, 12E:
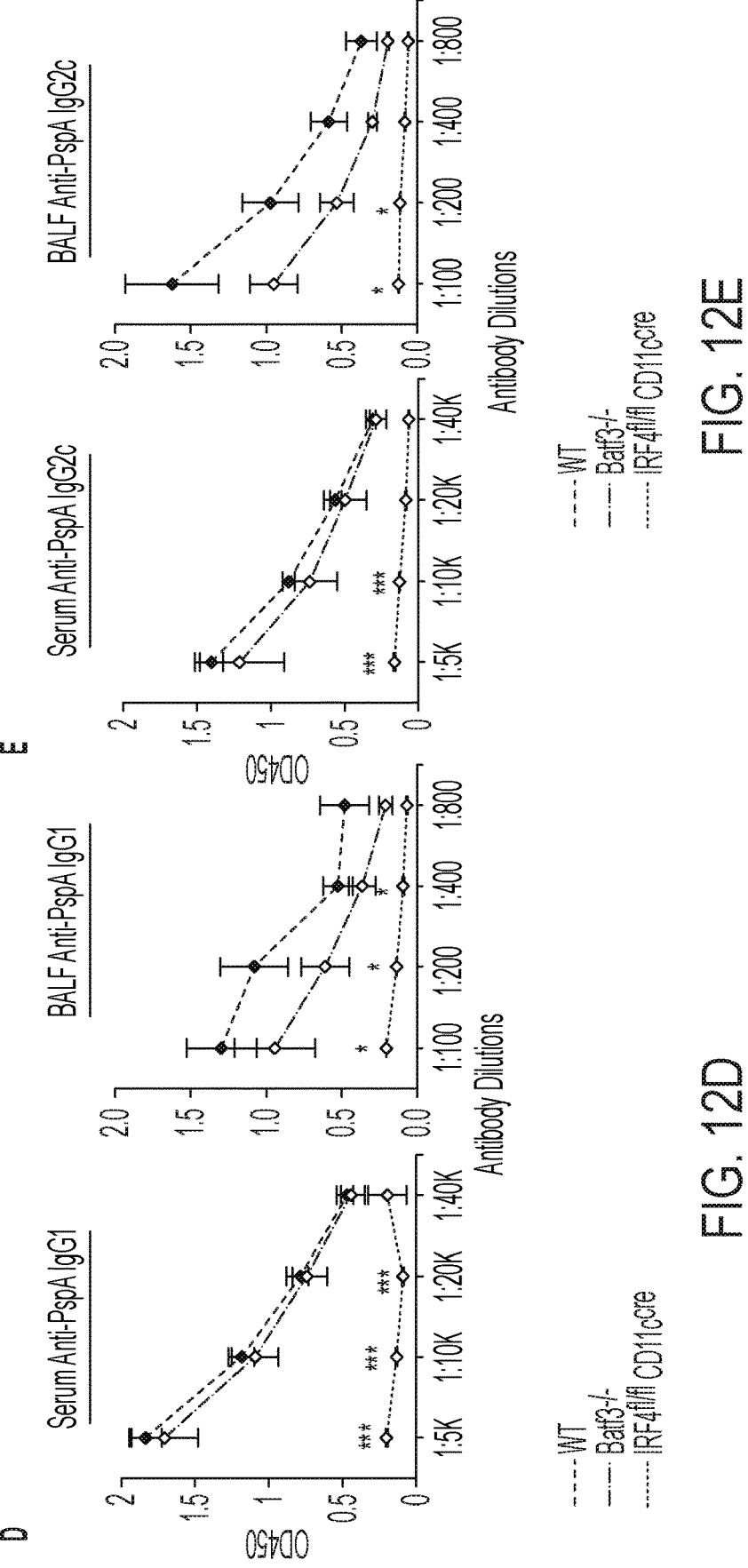
Figures 12F, 12G:
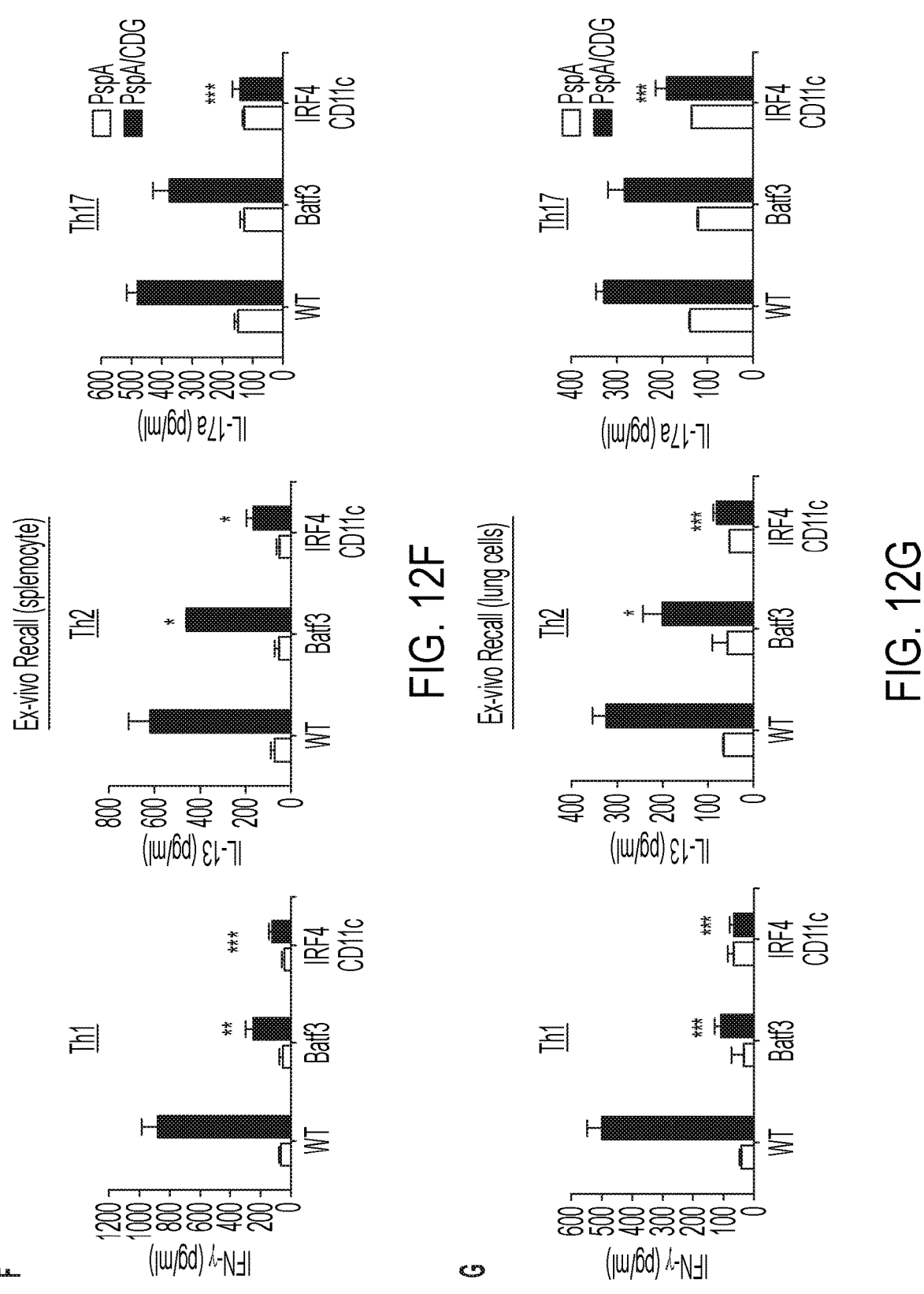

In contrast to the IRF4$^{fl/fl}$CD11c$^{cre}$ mice, Batf3$^{−/−}$ mice mounted antigen-specific IgG and IgA responses in a manner comparable to the WT following CDG/PspA immunization (FIGS. 1H, 12D-E). We concluded that cDC2 play a central role in mediating CDG adjuvant activity. Batf3$^{−/−}$ mice had impaired Th1 responses following immunization (FIG. 12F-G). Whether the defect is due to the lack of cDC1 remains to be determined since T cells also express Batf3.

TNFR2 is Essential for CDG Adjuvant Activity

Figure 13A:
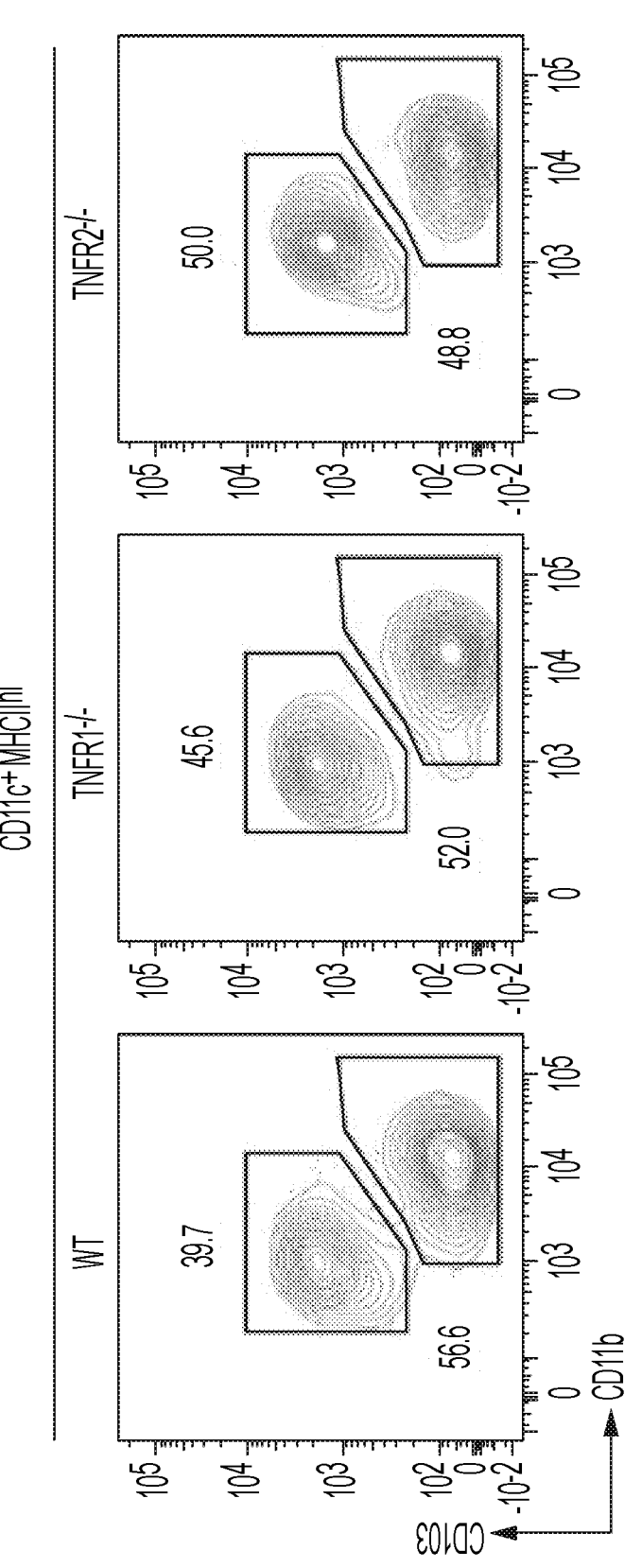
FIG. 13. A-B. Flow cytometry analysis of lung DCs subsets from WT, TNFR1-/-, and TNFR2-/- mice. n=3 C-D. WT, TNFR1-/- and TNFR2-/- mice were immunized (i.n.) with two doses (14 days apart) of PspA or PspA plus CDG (5 ug). Anti-PspA IgG1 (C) and IgG2c (D) in serum and BALF were determined by ELISA. n>3. E-F. Splenocytes (E) or lung cells (F) from immunized WT, TNFR1-/-, and TNFR2-/- mice were stimulated with 5 μg/ml PspA for 4 days in culture. Cytokines were measured in the supernatant by ELISA. n>3. Graphs represent means±standard error from three independent experiments. The significance is represented by and asterisk (*) where p<0.05 (unpaired Student's t test).
Figure 13B:
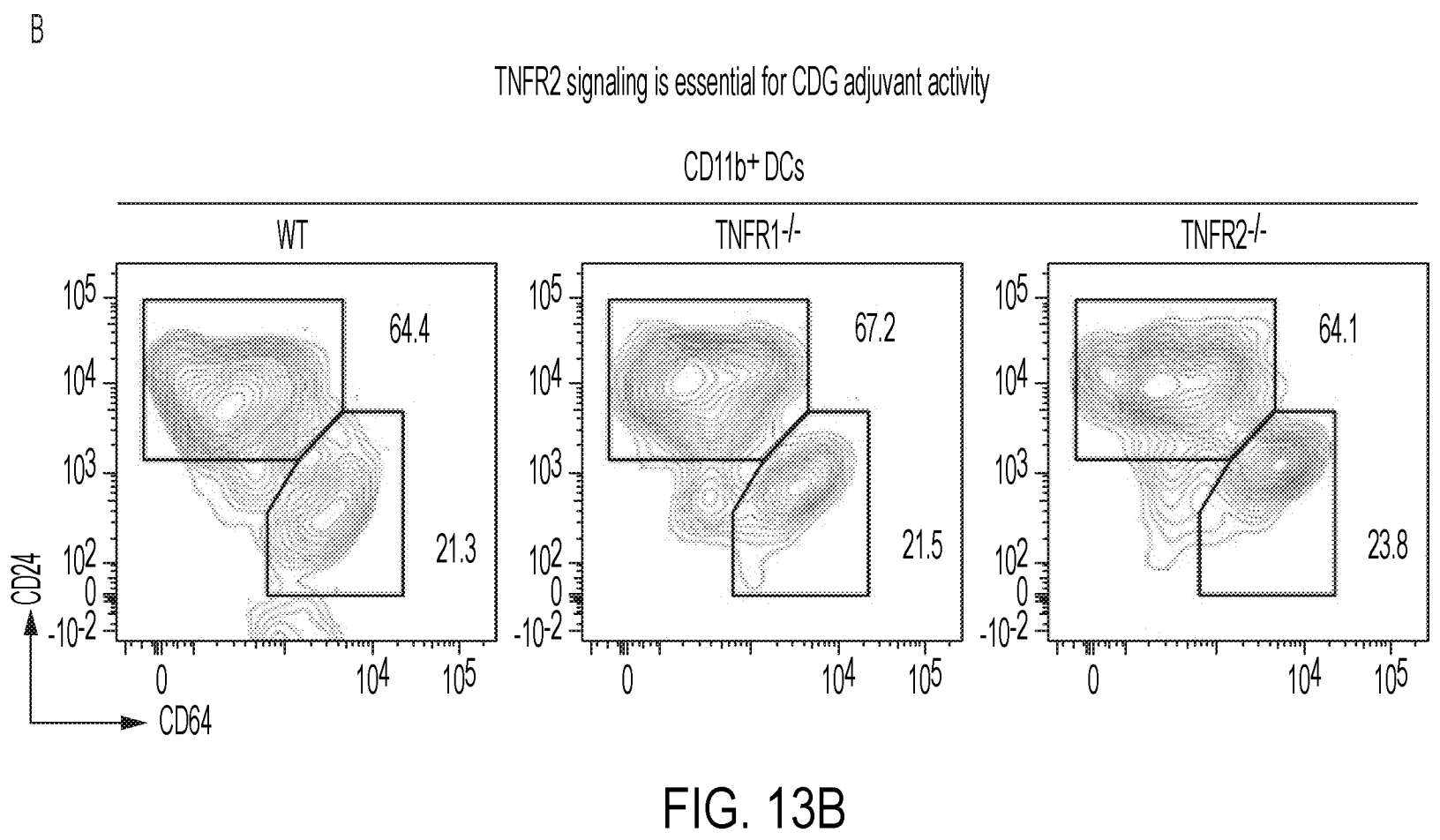
Figures 13C, 13D:
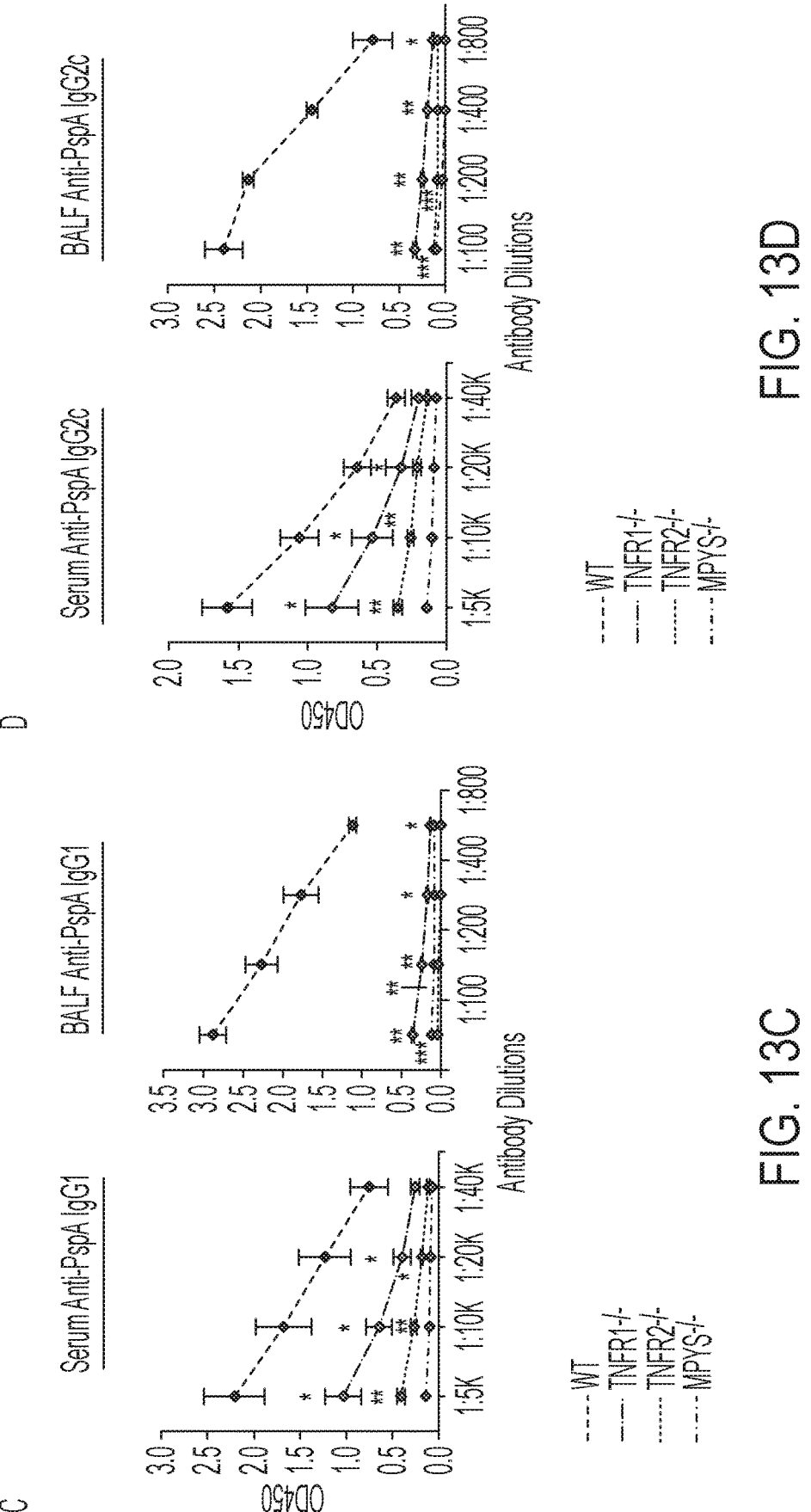
Figures 13E, 13F:
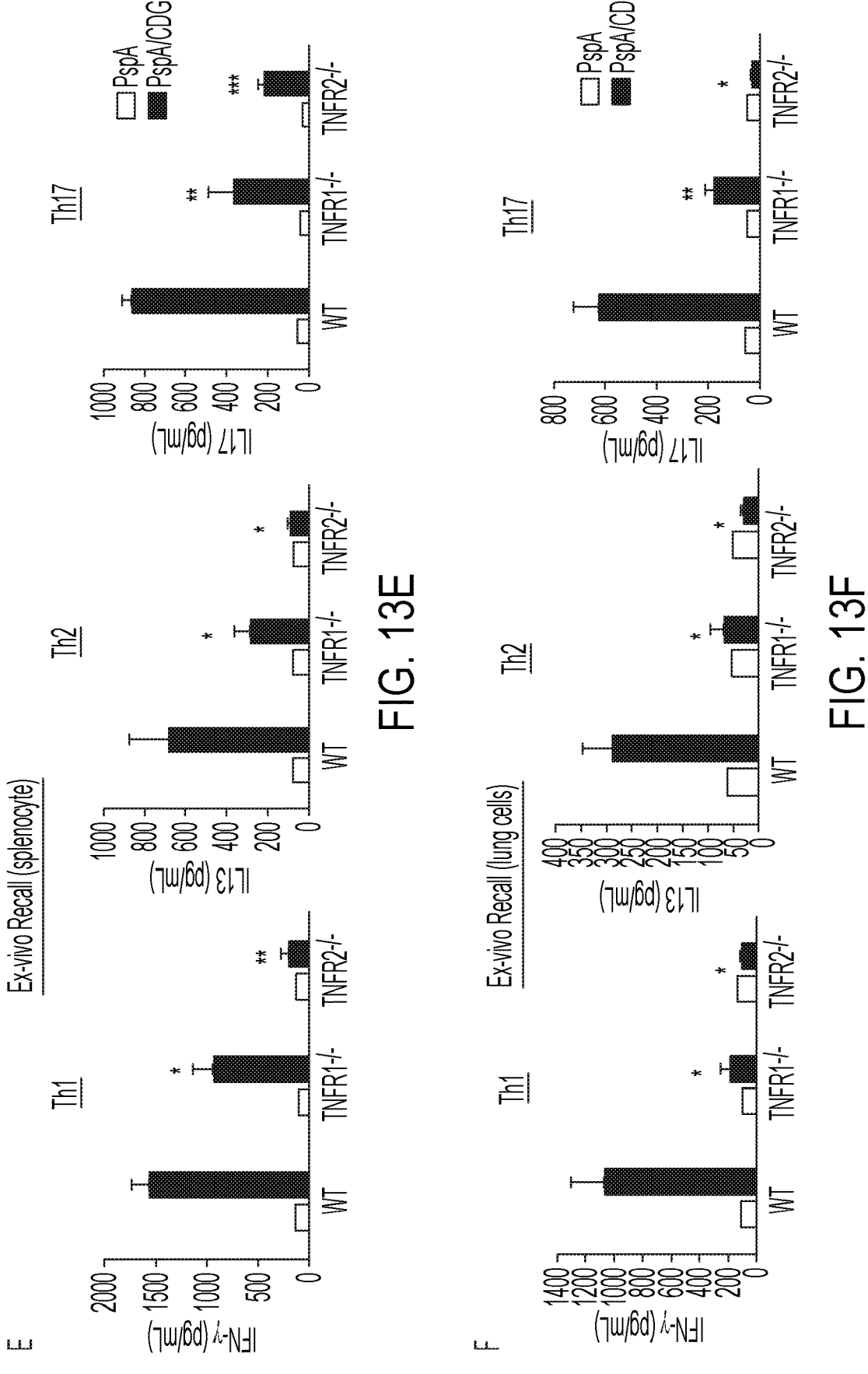

TNF signaling is critical for CDG adjuvant activity in vivo[15,16]. TNF signals through two TNFR1 and TNFR2. TNFR1 binds transmembrane TNF (tmTNF) and soluble TNF (sTNF) while TNFR2 only binds to tmTNF[34-37] The lung DC compartment is not altered by the lack of either TNFR1 or TNFR2 (FIG. 13A-B). Consistent with the previous report, we found that CDG induced reduced humoral and cellular immune responses in TNFR1$^{−/−}$ mice (FIG. 2A, 13C-F). Surprisingly, CDG completely lost its adjuvant activity in TNFR2$^{−/−}$ mice (FIG. 2A, 13C-F). We concluded that TNFR2 expression is essential for CDG adjuvant activity.

Figure 2A:
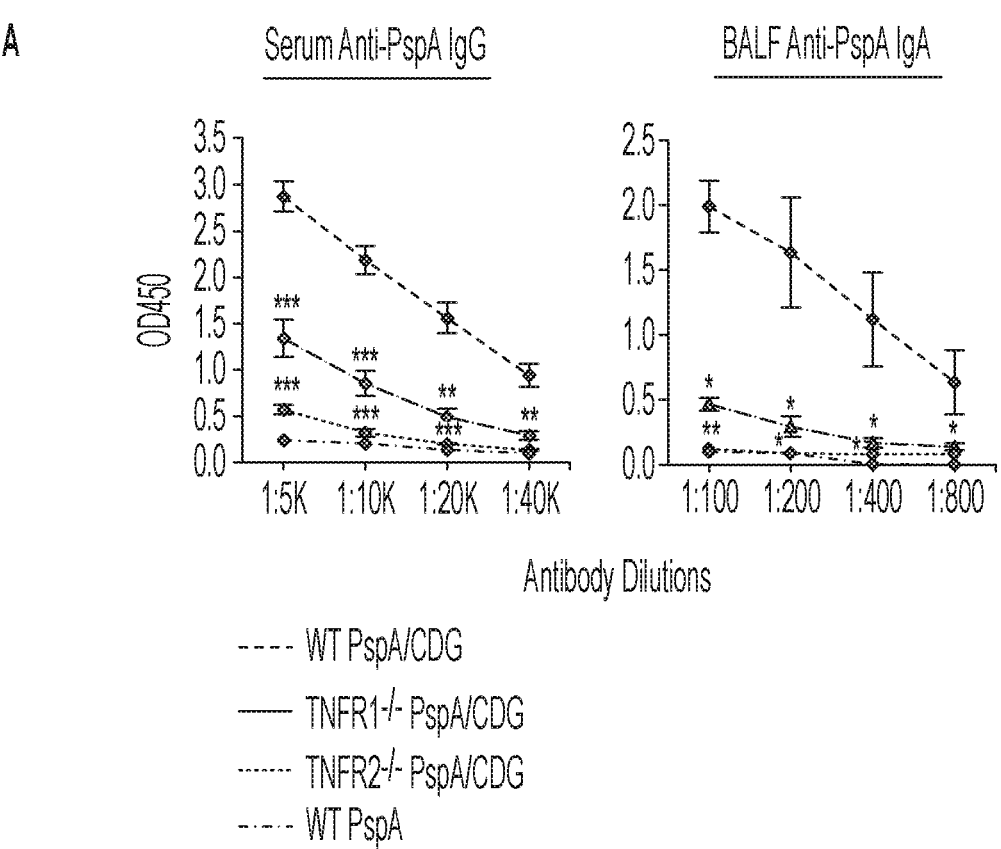
FIG. 2. cDC2 expression of TNFR2 is required for CDG-induced lung cDC2 maturation in vivo by activating RelB. A. C57BL/6 (WT), TNFR1$^{-/-}$ and TNFR2$^{-/-}$ mice were immunized (i.n.) with two doses of PspA or PspA plus CDG (5 ug). Serum anti-PspA IgG and BALF IgA were determined by ELISA. n=3. B. WT and TNFR2$^{-/-}$ mice were treated (i.n.) with saline or CDG (5 µg) for 16 hours. CD86 expression in lung cDC2 were determined by Flow cytometry. n=3. C. IRF4$^{fl/fl}$CD11c$^{cre}$ mice were adoptively transferred (i.n.) with lung cDC2 sorted from WT or TNFR2$^{-/-}$ mice lung. The recipient mice were administered (i.n.) with saline or CDG (5 µg) for 16 hrs. CD86 expression in lung cDC2 were determined by Flow cytometry. n=3. D. Flow cytometry analysis of TNFR2 expression on lung cDC2 in WT mice administered (i.n) with saline or CDG for 16 hrs. n>3. E. Flow cytometry analysis of TNFR2 expression on pRelB$^+$ cDC2 from mice treated with saline or CDG. n=3. F. Flow cytometry analysis of pRelB expression on TNFR2+ cDC2 from mice treated with CDG. n=3. G. Flow cytometry analysis of pRelB expression on cDC2 from WT and TNFR2$^{-/-}$ mice. n=3. H. Flow cytometry analysis of CD86 expression on lung cDC2 in RelB$^{fl/fl}$ and RelB$^{fl/fl}$CD11C$^{Cre}$ mice treated with CDG. n=3. Graphs represent means±standard error from three independent experiments. The significance is represented by and asterisk (*) where p<0.05 (unpaired Student's t test).
Figure 2B:
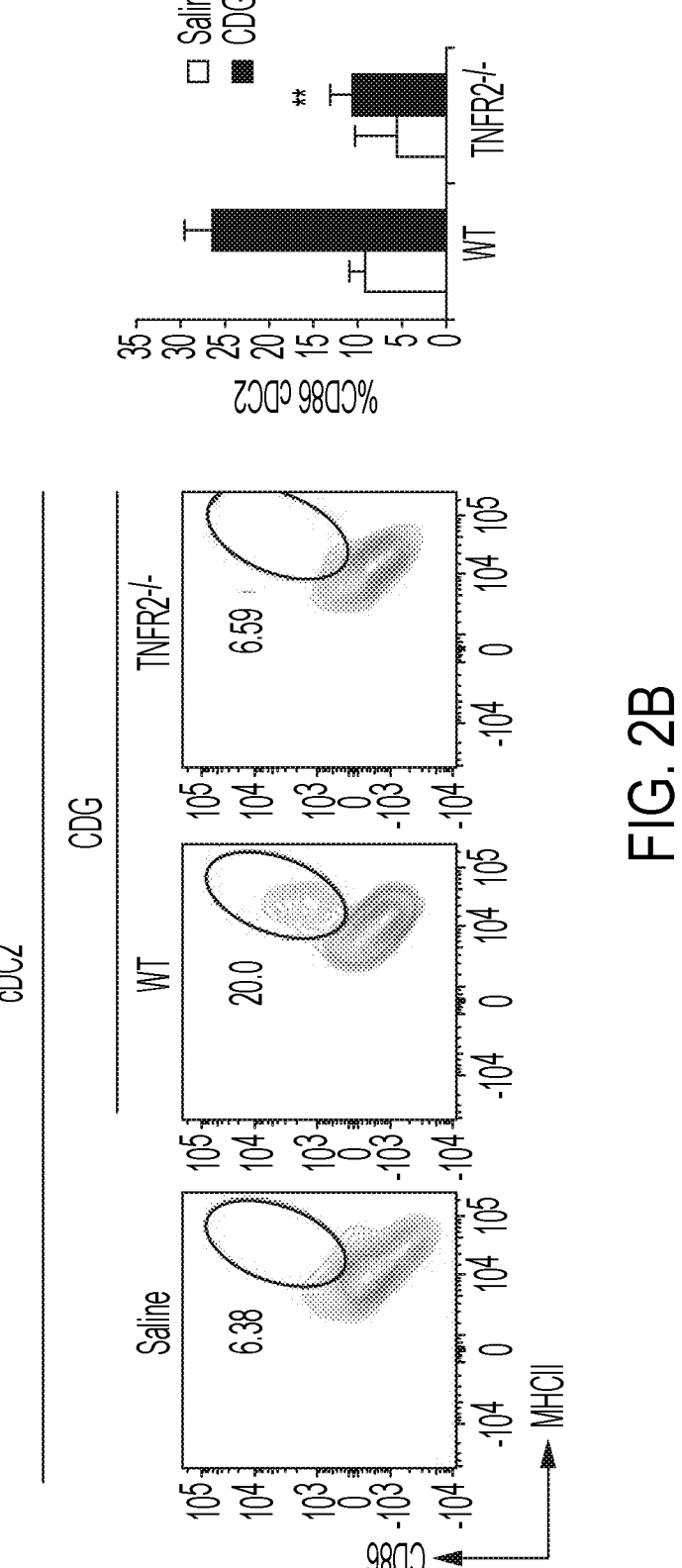
Figures 14A, 14B:
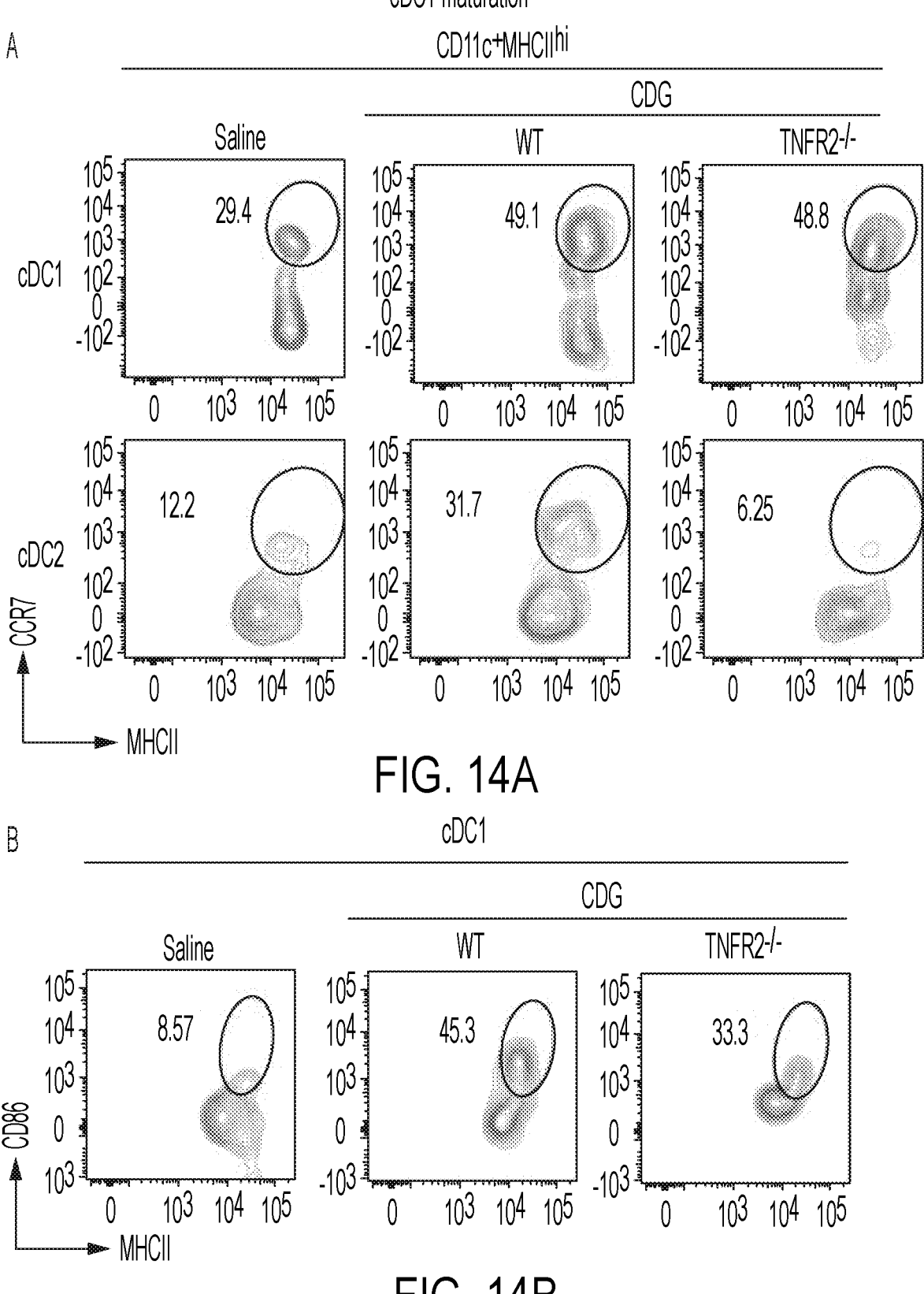
FIG. 14. A. WT, TNFR2-/- mice were treated (i.n.) with saline or CDG (5 μg) for 16 hours. CCR7 expression in lung cDC1 and cDC2 were determined by Flow cytometry. n=3. B. WT, TNFR2-/- mice were treated (i.n.) with saline or CDG (5 μg) for 16 hours. CD86 expression in lung cDC1 were determined by Flow cytometry. n=3. C. C57B6/J mice were administered (i.n.) with saline or CDG (5 μg). Isotype control Ab (50 μg) or anti-TNFR2 Ab (50 μg) was administered (i.n.) 30 min later. The lungs were harvested 16 hours later. CD86 expression in lung cDC2 was determined by Flow cytometry. n=3. D. Flow cytometry analysis of TNFR2 expression on lung cDC1 in WT mice administered (i.n) with saline or CDG for 16 hrs. n>3. E. Flow cytometry analysis of lung DCs populations in RelBfl/fl and RelBfl/flCD11CCre mice. n=3. F. Flow cytometry analysis of CD86 expression on lung cDC1 in RelBfl/fl and RelBfl/flCD11CCre mice treated with CDG. n=3.
Figure 14C:
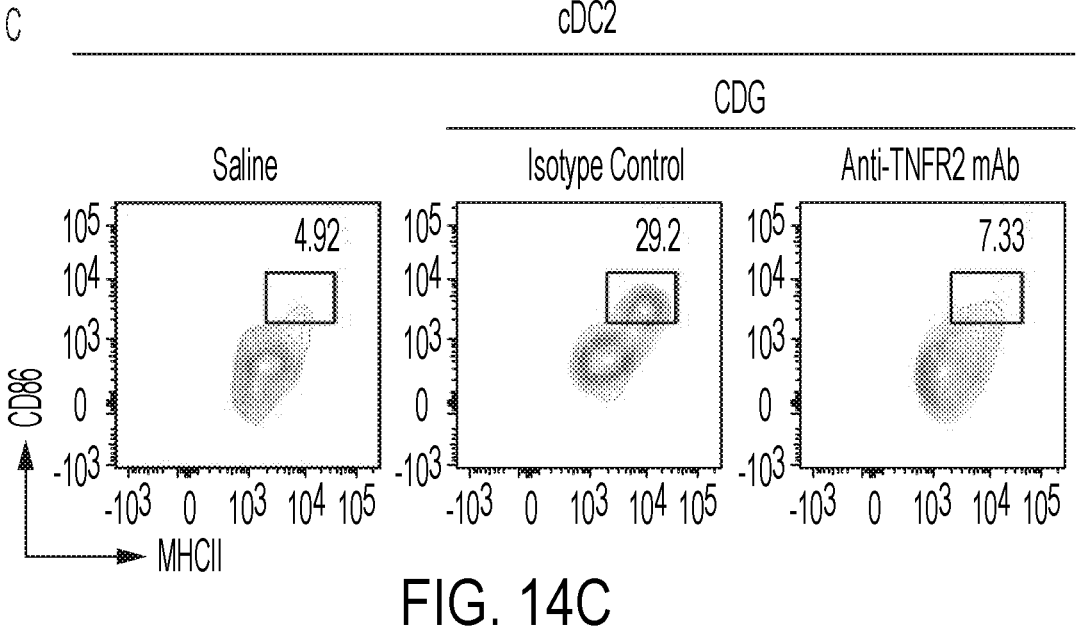

TNFR2 Expression on Lung cDC2 is Required for its Maturation cDC2 are critical for CDG adjuvant activity (FIG. 1). We next examined lung cDC2 maturation in the TNFR2$^{−/−}$ mice. We found that CDG did not enhance CD86 or CCR7 expression in lung cDC2 of TNFR2$^{−/−}$ mice in vivo (FIGS. 2B & 14A). In comparison, CDG induced CD86 and CCR7 expression on cDC1 of TNFR2$^{−/−}$ mice in vivo (FIG. 14A-B). Furthermore, blocking TNFR2 by mAb inhibited CDG-induced CD86 expression on cDC2 in vivo (FIG.

Figure 2C:
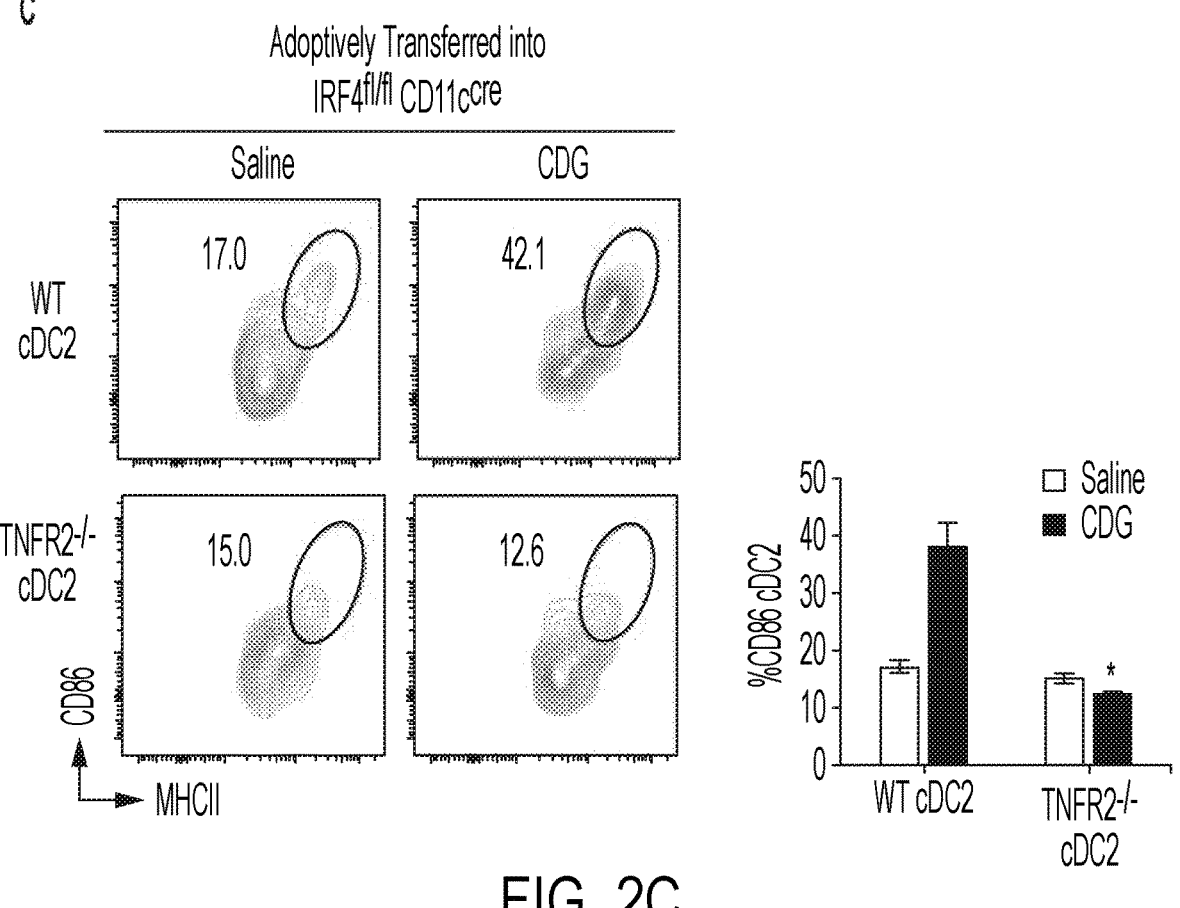

14C). Last, adoptively transferred TNFR2-deficient cDC2 into IRF4$^{fl/fl}$CD11c$^{cre}$ recipient mice failed to upregulate CD86 expression in response to intranasal CDG administration (FIG. 2C). Collectively, we concluded that TNFR2 expression on lung cDC2 are required for their maturation in response to CDG in vivo.

TNFR2$^+$ Lung cDC2 have Constitutively Activated RelB

Figure 2D:
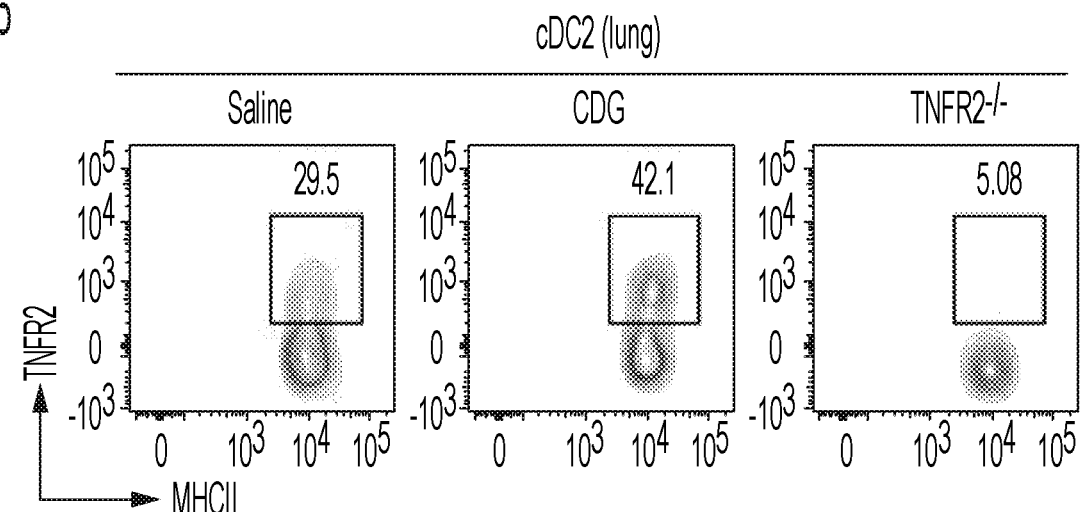
Figure 2E:
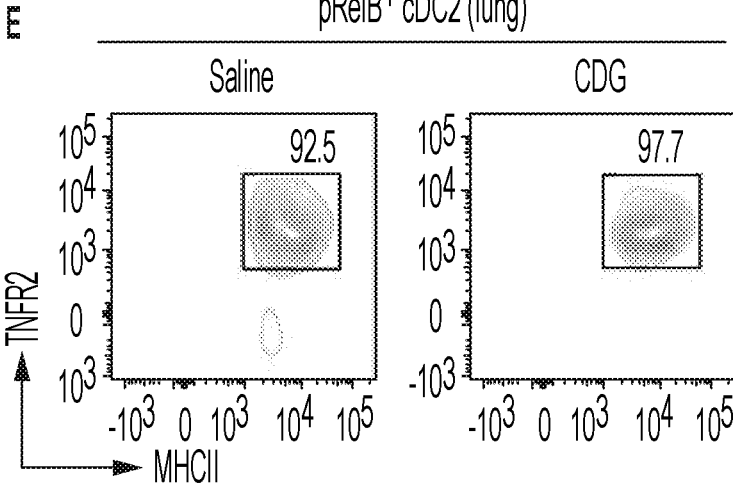
Figure 2F:
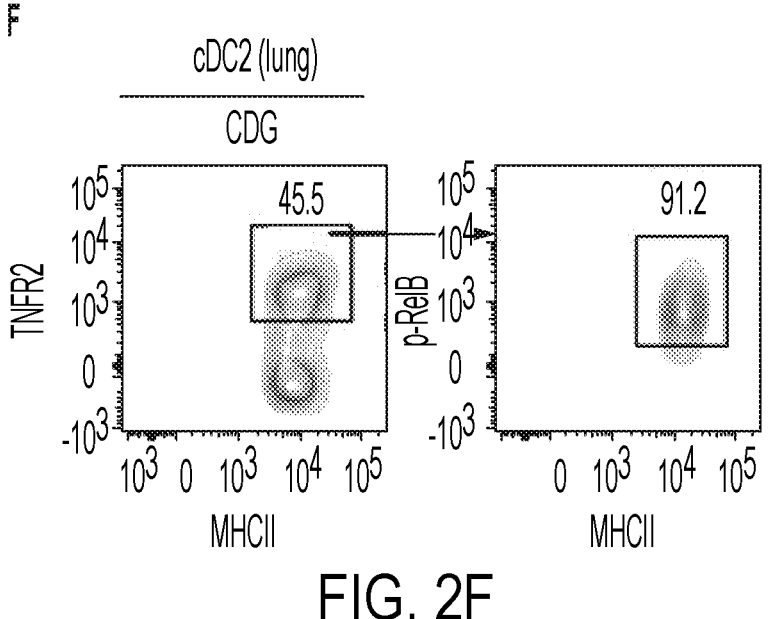
Figure 2G:
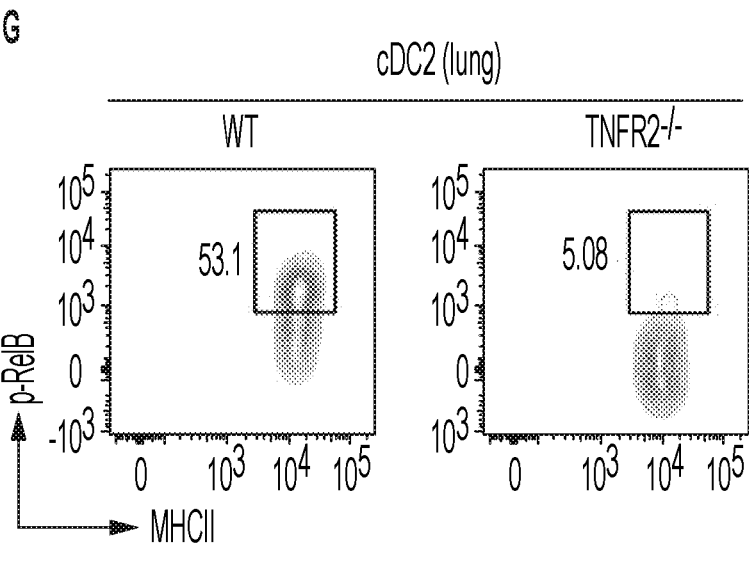
Figure 14D:
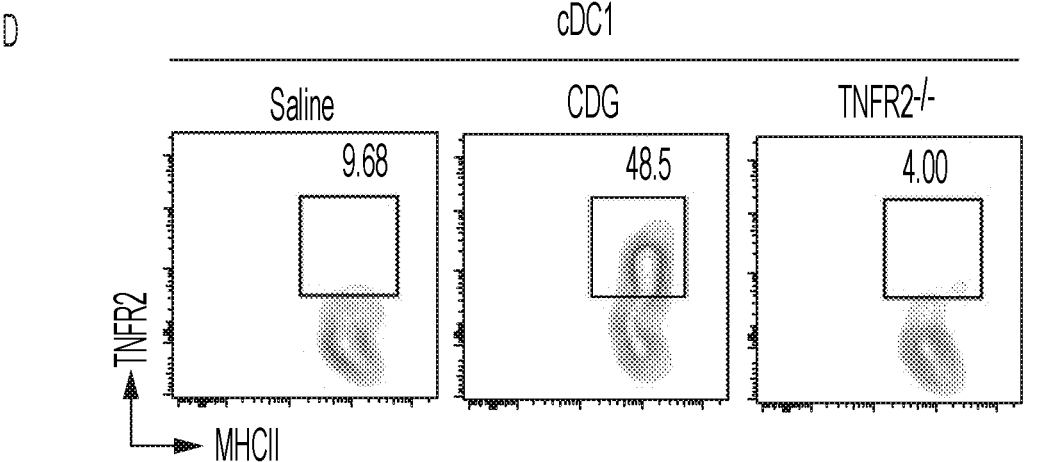

We next examine TNFR2 expression on lung cDC2. We found that a population of lung cDC2 constitutively express TNFR2 (FIG. 2D). In contrast, TNFR2 expression was not detected on steady-state lung cDC1 though CDG dramatically increased TNFR2 expression (FIG. 14D). Steady-state lung cDC2 have a pRelB$^+$ population (FIG. 1F). Interestingly, all the pRelB$^+$ cDC2 are TNFR2$^+$ (FIG. 2E, left panel). CDG further activate RelB in lung cDC2 upon CDG treatment (FIG. 1F). We found that all pRelB$^+$ cells in activated cDC2 expressed TNFR2 (FIG. 2E, right panel) and all the TNFR2$^+$ cDC2 are pRelB$^+$ (FIG. 2F). Last, cDC2 in TNFR2$^{-/-}$ mice lack pRelB indicating that RelB activation requires TNFR2 signaling (FIG. 2G). We concluded that the TNFR2$^+$ and pRelB$^+$ lung cDC2 are the same population.

RelB in DCs is Required for CDG-Induced cDC2 Maturation In Vivo.

Figure 2H:
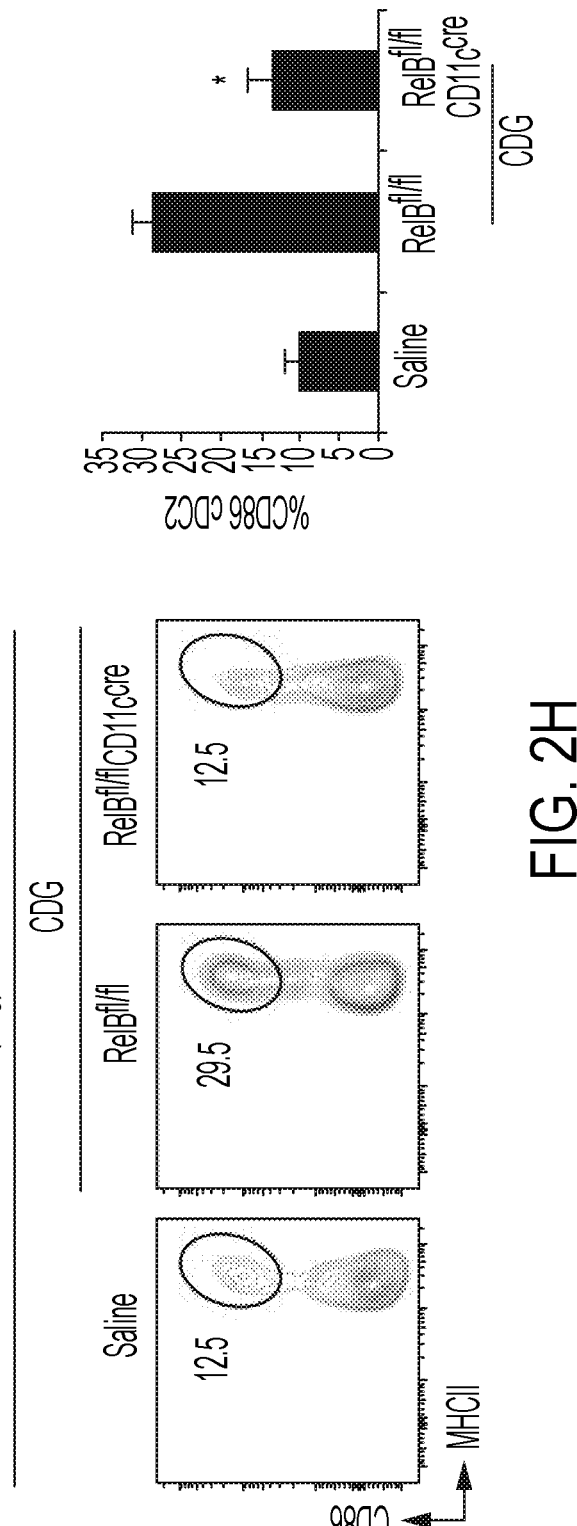
Figure 14E:
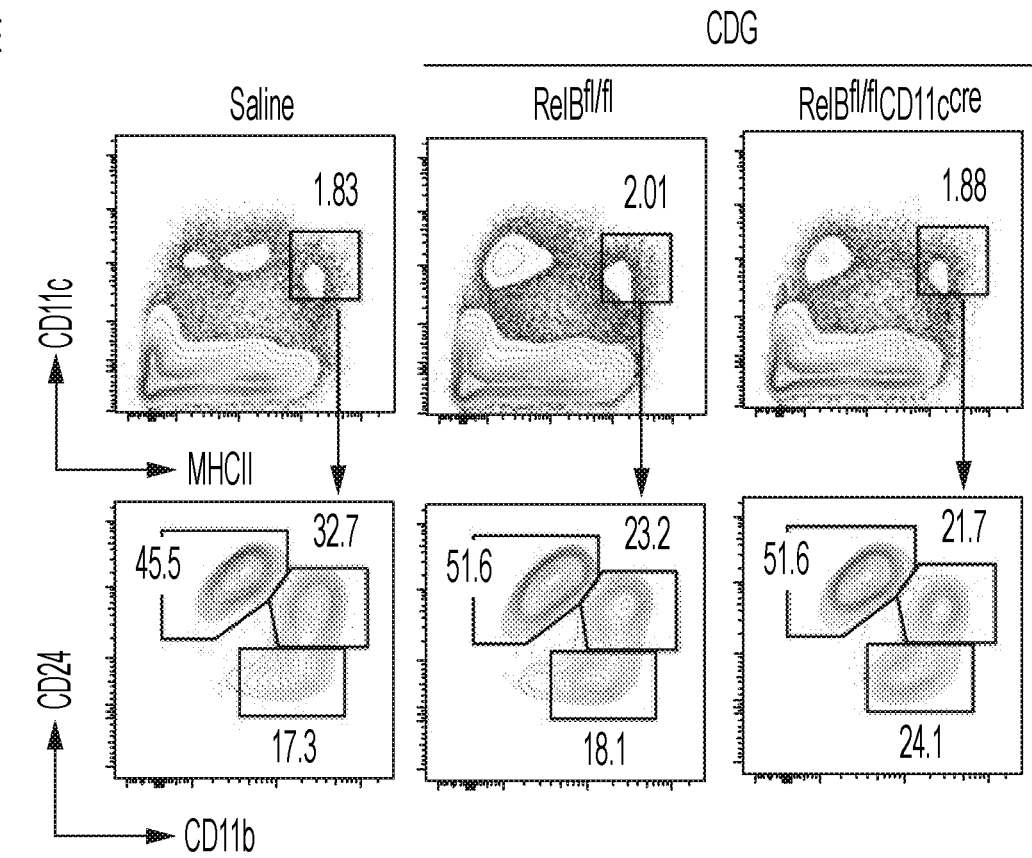
Figure 14F:
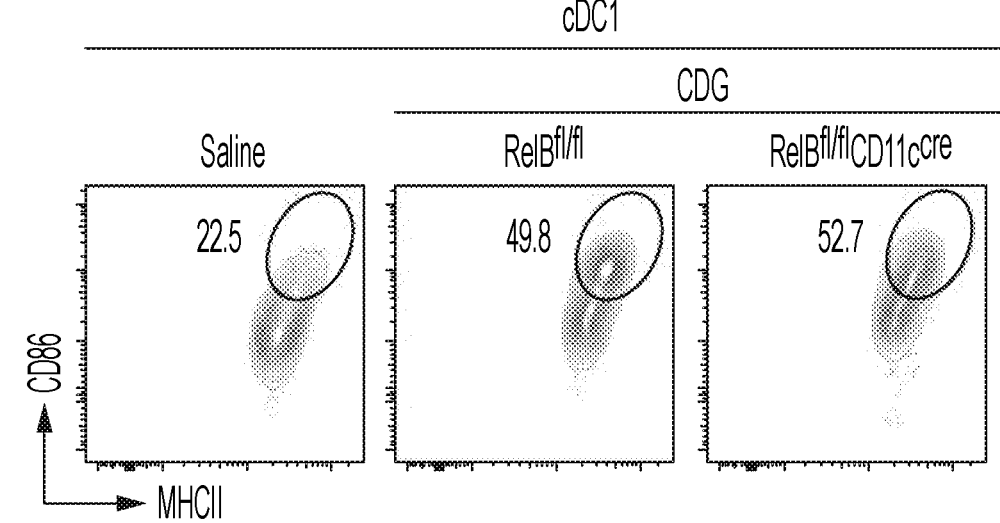

TNFR2 on lung cDC2 is required CDG-induced cDC2 maturation in vivo (FIG. 2C). We reasoned that RelB was required for CDG-induced cDC2 maturation too. We used RelB$^{fl/fl}$CD11c$^{cre}$ mice to ablate RelB in DCs. RelB$^{fl/fl}$CD11c$^{cre}$ mice have normal DC populations, with all subsets intact (FIG. 14E). In the absence of RelB in DCs, cDC2 failed to upregulate CD86 in response to CDG (FIG. 2H). cDC1, which do not activate RelB, upregulated CD86 (FIG. 14F). We concluded that CDG-induced lung cDC2 maturation depends on the cell-intrinsic signal of TNFR2-RelB.

Figure 3A:
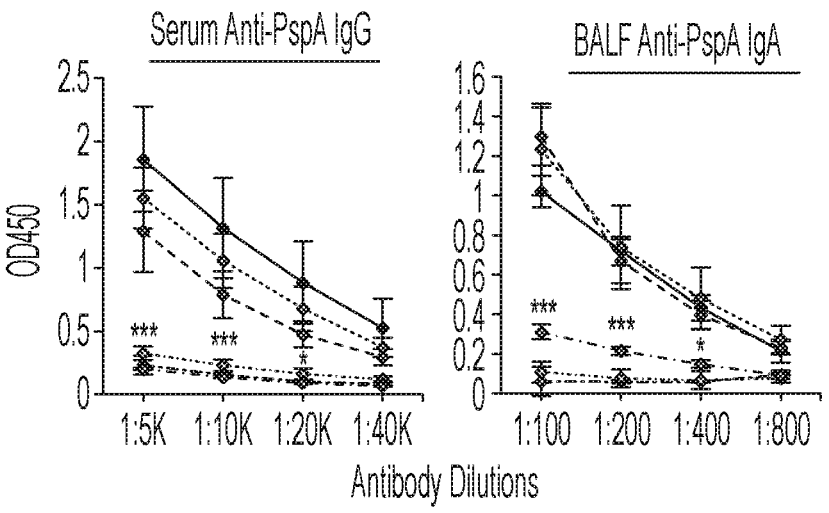
FIG. 3. cDC2 expression of TNFR2 and RelB is required for Th1 and Th17 responses, but dispensable for CDG-induced antibody response. A. IRF4$^{fl/fl}$CD11c$^{cre}$ mice were adoptively transferred (i.n.) with lung cDC2 sorted from WT or TNFR2$^{-/-}$ mice lung and immunized (i.n.) with PspA or CDG/PspA. Serum anti-PspA IgG and BALF anti-PspA IgA were determined by ELISA. n=3. B. RelB$^{fl/fl}$ and RelB$^{fl/}$$_f$CD11C$^{Cre}$ mice were immunized (i.n) with CDG/PspA or PspA alone as before. Serum anti-PspA IgG and BALF anti-PspA IgA were determined by ELISA. n=3. C. Lung cells from immunized RelB$^{fl/fl}$ and RelB$^{fl/fl}$CD11C$^{Cre}$ mice were stimulated with 5 µg/ml PspA for 4 days in culture. Cytokines were measured in the supernatant by ELISA. n>3. Graphs represent means±standard error from three independent experiments. The significance is represented by and asterisk (*) where p<0.05 (unpaired Student's t test).

TNFR2$^+$ cDC2 is Required for CDG-Induced Th1 and TH17 Responses but Dispensable for the Humoral Responses We next sought to determine if TNFR2 expression on cDC2 was needed for the adjuvant activity of CDG. Unexpectedly, even though adoptively transferred TNFR2-deficient cDC2 failed to upregulate CD86 in response to CDG (FIG. 2C), they induced serum anti-PspA IgG and IgA when transferred into IRF4$^{fl/fl}$CD11c$^{cre}$ mice (FIG. 3A). In fact, the anti-PspA IgG and IgA in IRF4$^{fl/fl}$CD11c$^{cre}$ mice receiving TNFR2-deficient cDC2 and WT cDC2 were comparable (FIG. 3A).

Figure 3B:
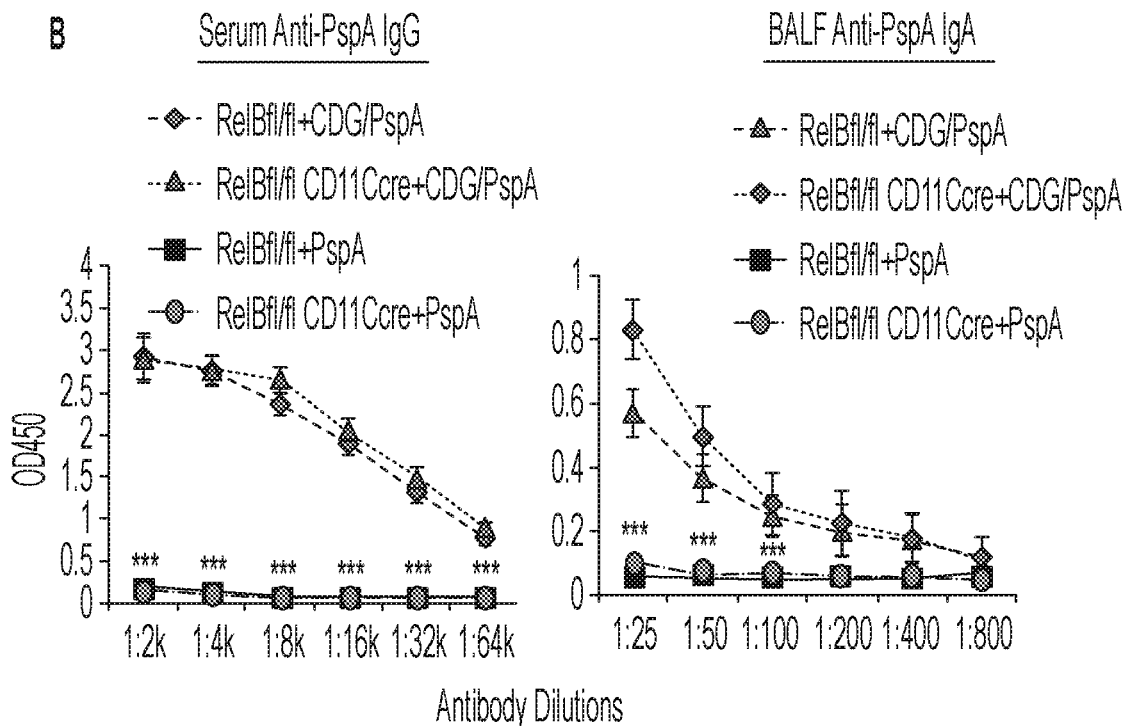
Figure 3C:
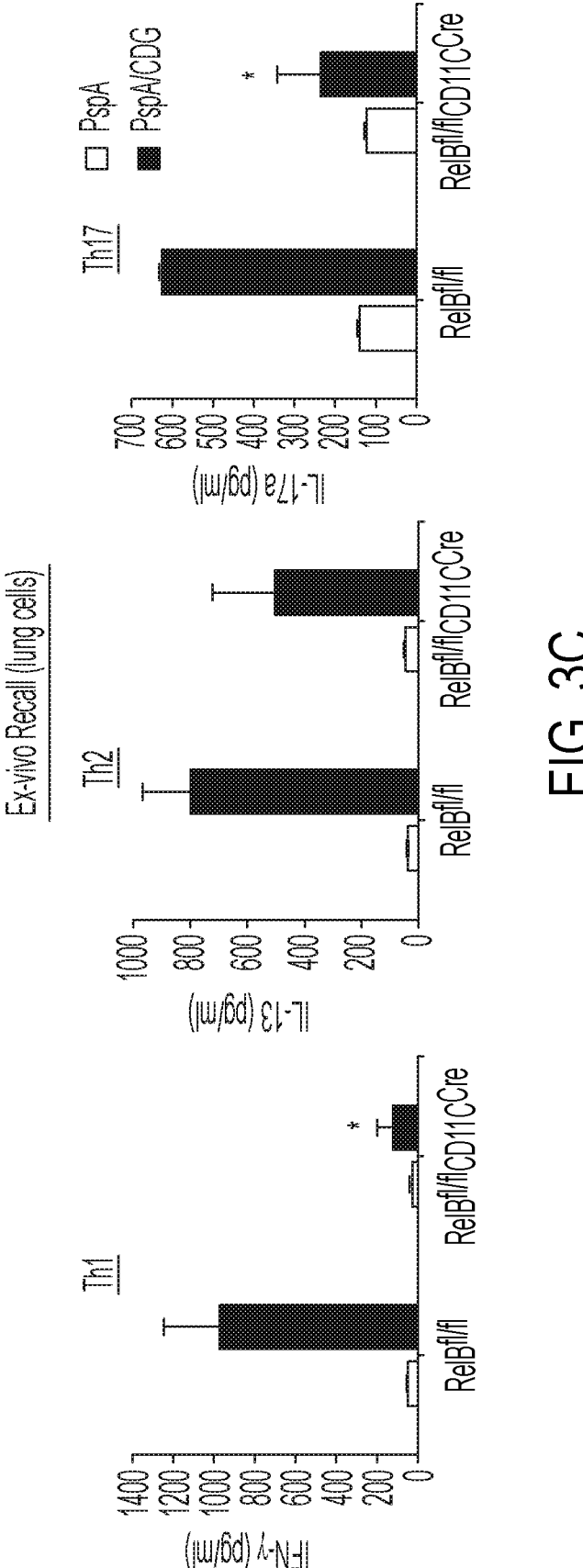

We then examined CDG adjuvant activity in the RelB$^{fl/fl}$CD11c$^{cre}$ mice, which also lack mature cDC2. Upon immunization with PspA and CDG, RelB$^{fl/fl}$CD11c$^{cre}$ mice produced normal levels of IgG and IgA (FIG. 3B). RelB$^{fl/fl}$CD11c$^{cre}$ mice failed to induce Th1 and Th17 responses in the lung (FIG. 3C). Collectively, the data suggested that TNFR2$^+$ cDC2 is important for CDG-induced maturation and generation of Th1/Th17 responses, but is dispensable for humoral responses.

TNFR2 Defines Two Functionally Distinct Subsets of Lung cDC2 cDC2 is a heterogeneous population[21, 32, 38, 39]. We showed that lung TNFR2$^+$pRelB$^+$ cDC2 were mature and required for the Th1/Th17 responses but not humoral responses while the TNFR2$^-$ cDC2 was not mature but mediates CDG-induced antibody response. We assessed whether TNFR2 expression could define functionally distinct lung cDC2 subsets.

Figures 4A, 4B, 4C:
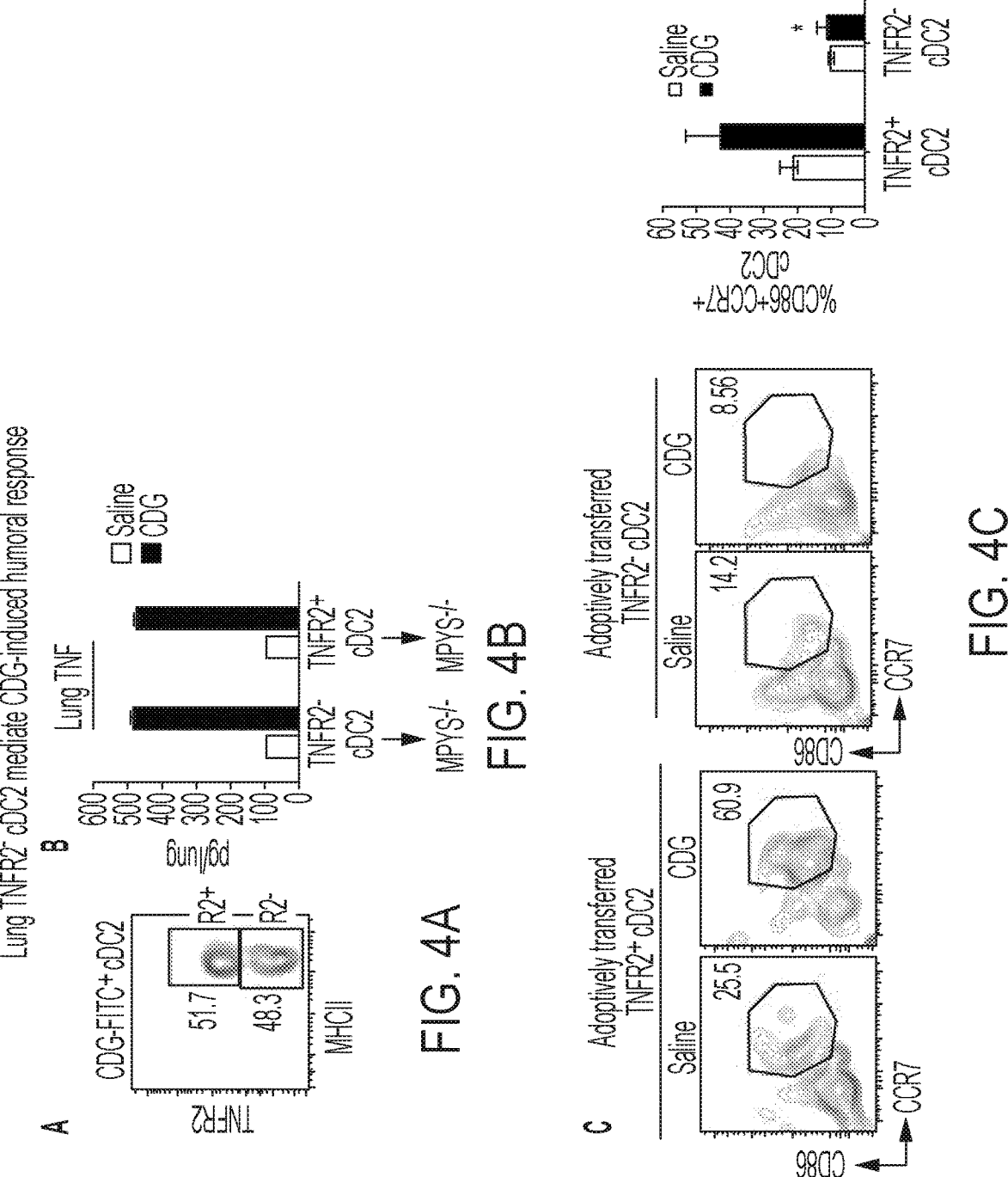
FIG. 4: Lung TNFR2$^-$ cDC2 mediate CDG-induced humoral response. A. Flow cytometry analysis of TNFR2 expression on lung CDG-FITC+ cDC2 from WT mice. n=3. B. Lung TNF production in CDG treated (i.n.) MPYS$^{-/-}$ mice adoptively transferred with WT TNFR2$^+$ or TNFR2$^-$ lung cDC2. n=3 C. Sorted TNFR2+ and TNFR2$^-$ lung cDC2 from WT mice were labelled with CFSE and adoptively transferred into the MPYS$^{-/-}$ mice. Recipient mice were treated with CDG (i.n.) for 16 hrs. CD86 and CCR7 expression on CFSE positive lung cells were examined by Flow cytometry. n=3. D. Sorted TNFR2+ and TNFR2$^-$ lung cDC2 from WT mice were adoptively transferred into the MPYS$^{-/-}$ mice. Recipient mice were immunized (i.n.) with PspA or CDG/PspA twice. Serum anti-PspA IgG were determined by ELISA. n=3. E. Sorted TNFR2+ and TNFR2$^-$ lung cDC2 from WT mice were adoptively transferred into IRF4$^{fl/fl}$CD11c$^{cre}$ mice. Recipient mice were immunized (i.n.) with PspA or CDG/PspA. Serum anti-PspA IgG were determined by ELISA. n=3. F. Lung cells from recipient IRF4$^{fl/fl}$CD11c$^{cre}$ mice were stimulated with 5 µg/ml PspA for 4 days in culture. Cytokines were measured in the supernatant by ELISA. G. A cartoon illustrating following CDG administration, TNFR2$^+$ cDC2 activate RelB to induce Th1, Th2 and Th17 responses while TNFR2$^-$ cDC2 mediate the antibody response. Graphs represent means±standard error from three independent experiments. The significance is represented by and asterisk (*) where p<0.05 (unpaired Student's t test).
Figures 15A, 15B:
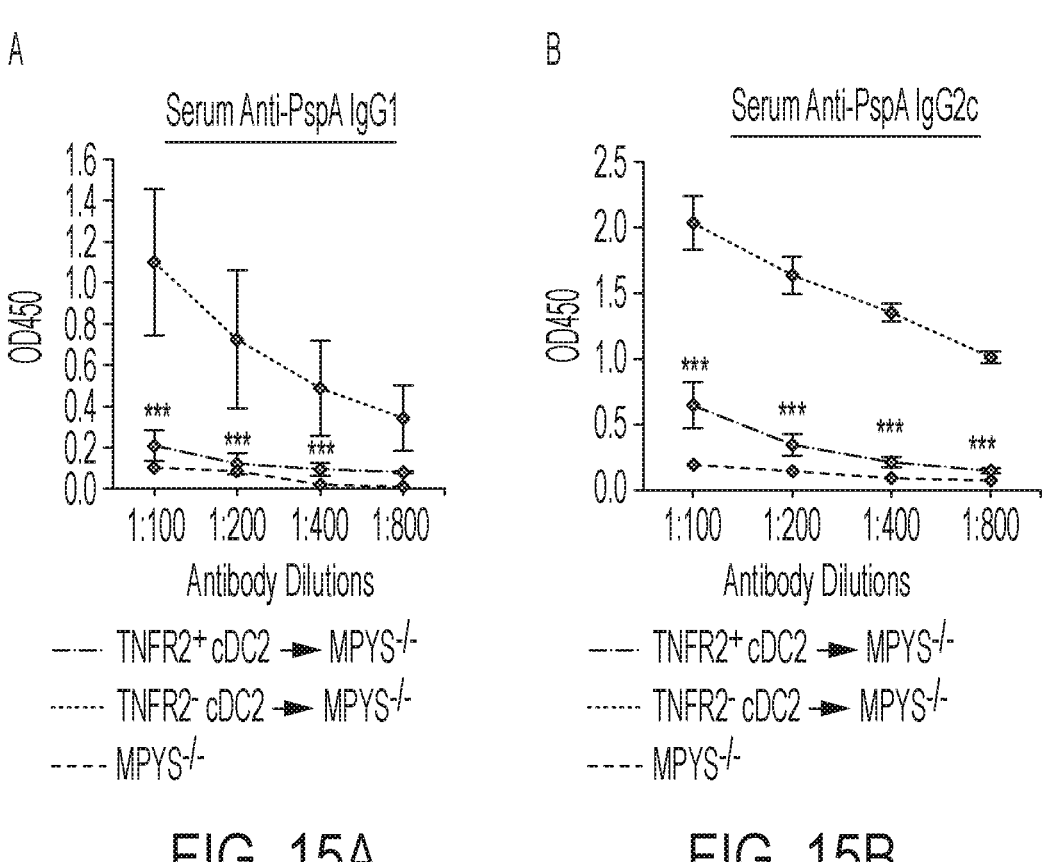
FIG. 15. A-B. Sorted TNFR2+ and TNFR2− lung cDC2 from WT mice were adoptively transferred into the MPYS−/− mice. Recipient mice were immunized (i.n.) with CDG/PspA. Serum anti-PspA IgG1 (A) and IgG2c (B) were determined by ELISA. n=3. Graphs represent means±standard error from three independent experiments. The significance is represented by and asterisk (*) where p<0.05 (unpaired Student's t test).

Both cDC2 populations took up CDG in vivo (FIG. 4A). When adoptively transferred into MPYS$^{-/-}$ mice, both produced lung TNF (FIG. 4B). MPYS$^{-/-}$ mice themselves do not respond to CDG[15]. Consistently, adoptively transferred TNFR2$^+$ cDC2 upregulated CD86 and CCR7 in response to CDG whereas TNFR2$^-$ cDC2 failed to do so (FIG. 4C). Importantly, adoptive transfer of TNFR2$^+$ cDC2 into MPYS$^{-/-}$ (FIGS. 4D, 15A-B) and IRF4$^{fl/fl}$CD11c$^{cre}$ mice (FIG. 4E) failed to rescue antibody production. Consistent with the RelB$^{fl/fl}$CD11c$^{cre}$ results, TNFR2$^+$ cDC2 were able to rescue Th1/Th17 responses in the IRF4$^{fl/fl}$CD11c$^{cre}$ mice (FIG. 4F). TNFR2$^+$ cDC2 also rescued Th2 response, which is different from the RelB$^{fl/fl}$CD11c$^{cre}$ mice (FIGS. 4F & 3C). We speculate that the ability of TNFR2$^+$ cDC2 to mediate CDG-induced Th2 responses maybe redundant in vivo.

Figures 4D, 4E:
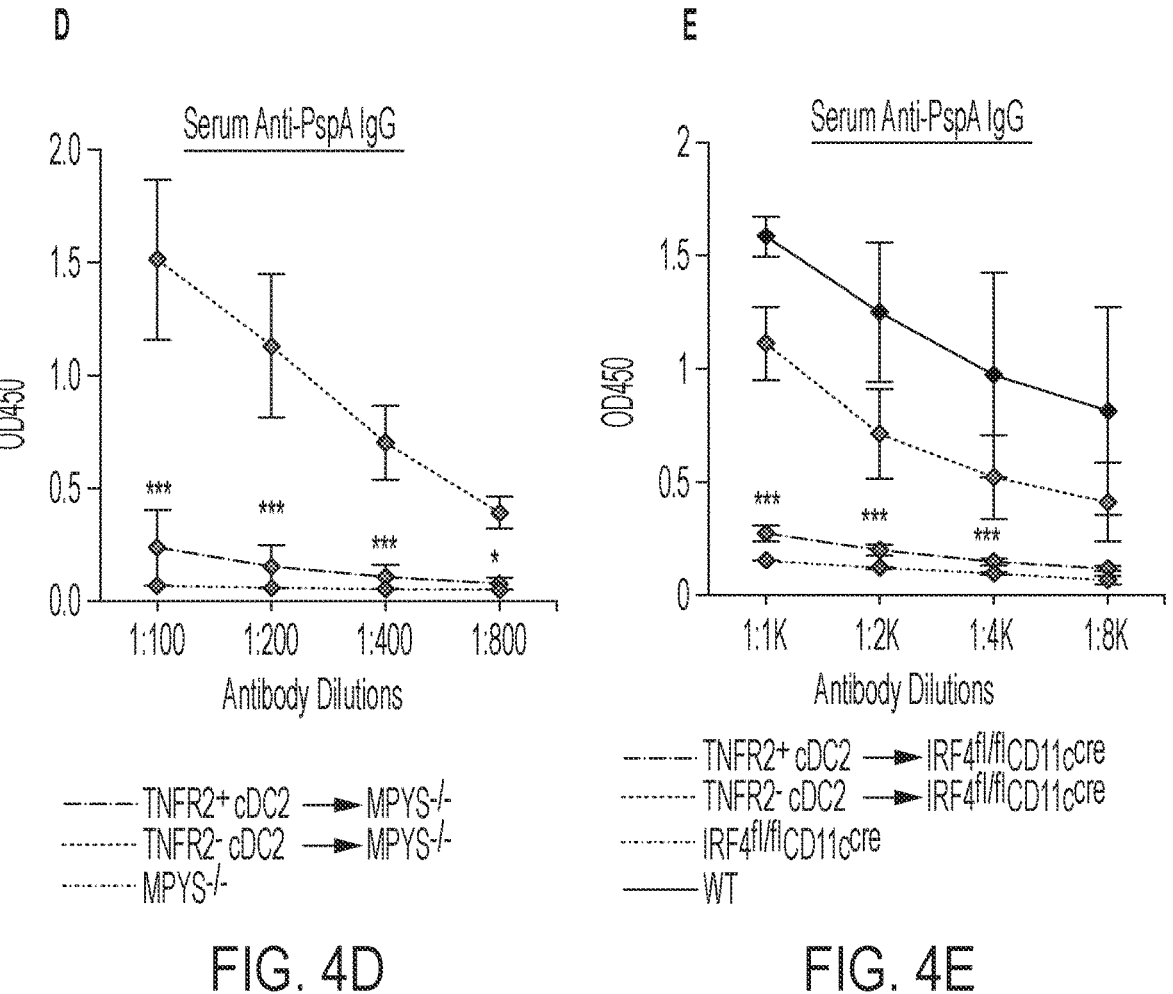
Figure 4F:
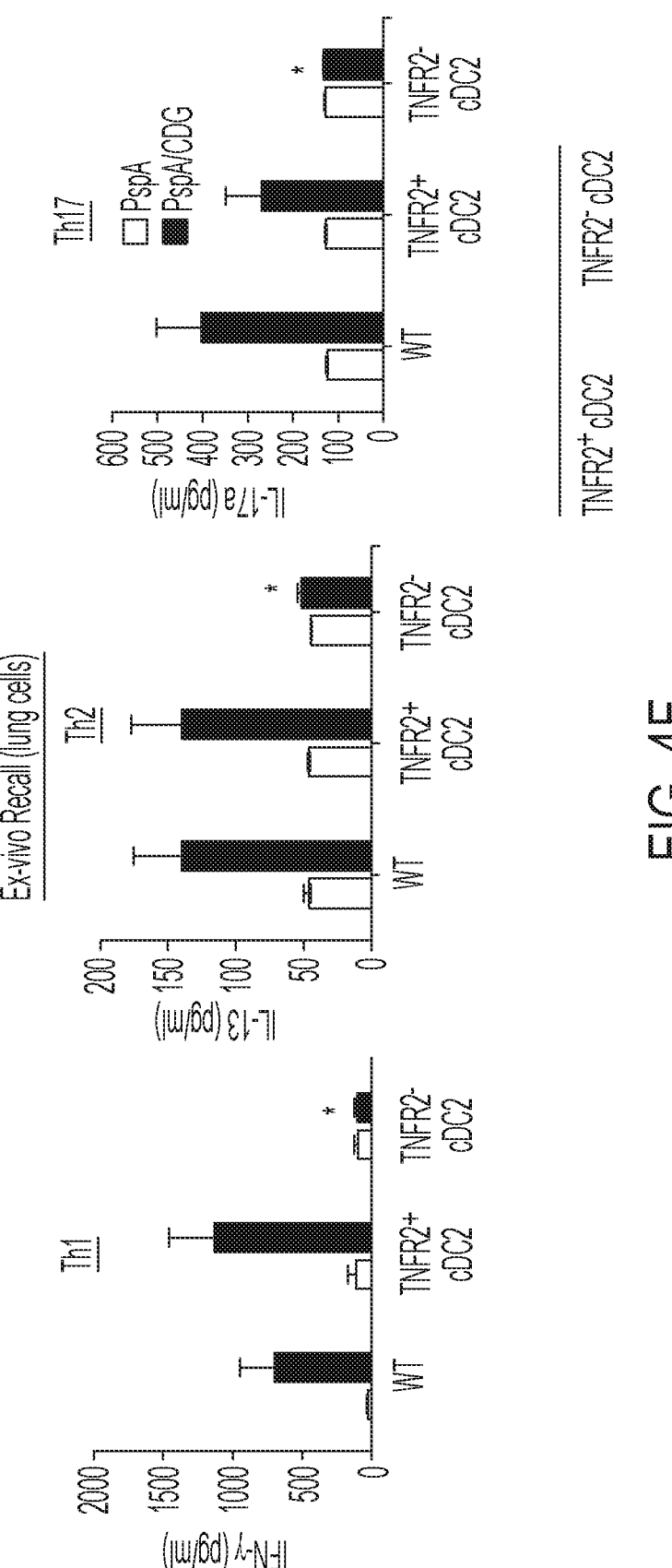

In contrast, adoptive transfer of TNFR2$^-$ cDC2 completely restored antibody, but not Th, responses in MPYS$^{-/-}$ (FIGS. 4D, 15A-B) and IRF4$^{fl/fl}$CD11c$^{cre}$ mice (FIG. 4E-F). In fact, levels of anti-PspA IgG and IgA in IRF4$^{fl/fl}$CD11c$^{cre}$ mice receiving TNFR2$^-$ cDC2 were similar to the WT (FIG. 4E). We concluded that lung cDC2 can be divided into two functionally distinct subsets: TNFR2$^+$ cDC2 and TNFR2$^-$ cDC2. The TNFR2$^+$ cDC2 are important for CDG-induced cellular immunity, while TNFR2$^-$ cDC2 are responsible for CDG-induced humoral responses (FIG. 4G).

Figures 5A, 5B, 5C:
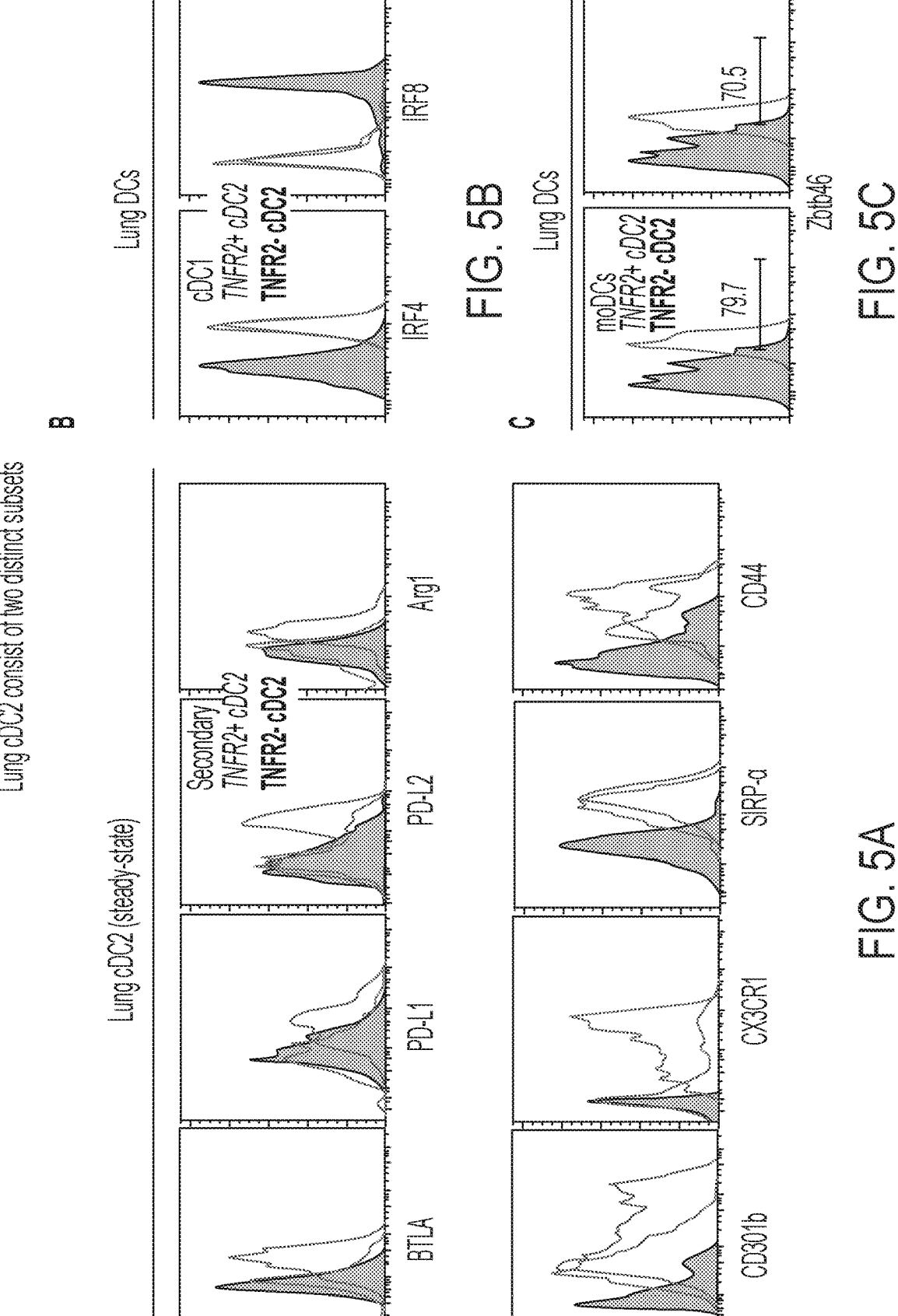
FIG. 5: Lung cDC2 consist of two distinct subsets. A. Flow cytometry analysis of lung TNFR2$^+$ vs TNFR2$^-$ cDC2 at steady-state. n=3. B-C. Flow cytometry analysis of IRF4 and IRF8 (B) and Zbtb46 (C) in TNFR2$^+$ and TNFR2$^-$ cDC2. n=3. D. Flow cytometry analysis in lungs of IRF4$^{fl/fl}$CD11c$^{cre}$ mice reconstituted with CD45.1+ pre-cDC2. n=3. pre-cDC2 were sorted from the bone marrow of B6.CD45.1 mice and transferred (i.n.) into IRF4$^{fl/fl}$CD11c$^{cre}$ mice. n=3. E. Phenotypic analysis of CD45.1 TNFR2$^+$ and TNFR2$^-$ cDC2 transferred into IRF4$^{fl/fl}$CD11c$^{cre}$ mice. n=3. F. Flow cytometry analysis of TNFR2 expression on cDC2 subsets transferred into MPYS$^{-/-}$ mice treated with CDG (i.n.) for 16 hrs. n=3.
Figures 16A, 16B, 16C, 16D:
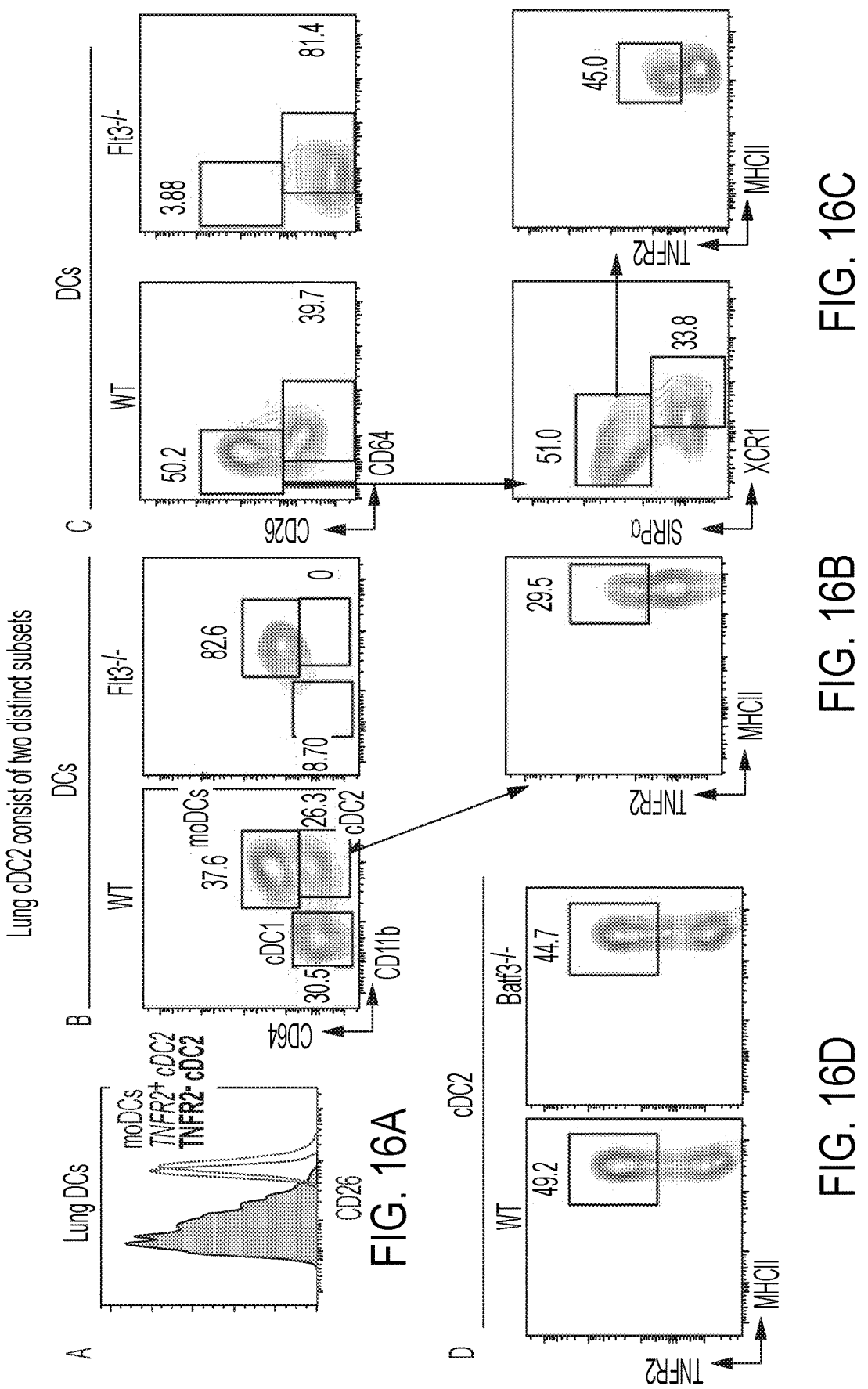
FIG. 16. A. Flow cytometry analysis of CD26 expression on lung TNFR2+ and TNFR2− cDC2. B-D. Flow cytometry analysis of lung DCs subsets in WT, Flt3−/− and Batf3−/− mice. n=3. Graphs represent means±standard error from three independent experiments. The significance is represented by and asterisk (*) where p<0.05 (unpaired Student's t test).

TNFR2$^+$ and TNFR2$^-$ Lung cDC2 are Derived from Pre-cDC2 but not from Each Other We further characterized these steady-state lung cDC2 populations. We found that the TNFR2$^+$ cDC2 are positive for BTLA, PDL-1, arginase 1 (Arg1). The TNFR2$^+$ cDC2 also have mixed expression of PD-L2 and CD301b (FIG. 5A). The lung TNFR2$^-$ cDC2 expressed CX3CR1 (FIG. 5A). Both populations express common cDC2 markers as SIRPα, CD26, IRF4 and Zbtb46 (FIGS. 5A, 5B & 16A)[40,41] Furthermore, both subsets of cDC2 were absent in Flt3$^{-/-}$ mice (FIGS. 16B-D). Last, TNFR2$^+$ and TNFR2$^-$ cDC2 are negative for cDC1 markers IRF8, XCR1 and not affected in Batf3$^{-/-}$ mice confirming their identity as cDC2 (FIG. 5B, 16C-D).

Figure 5D:
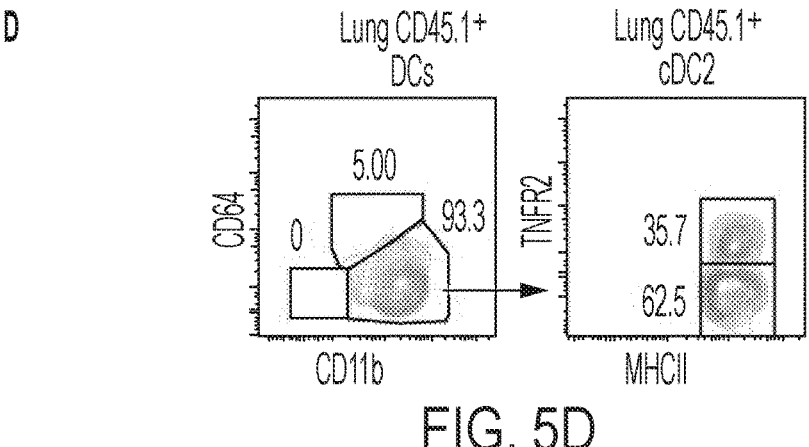
Figure 5E:
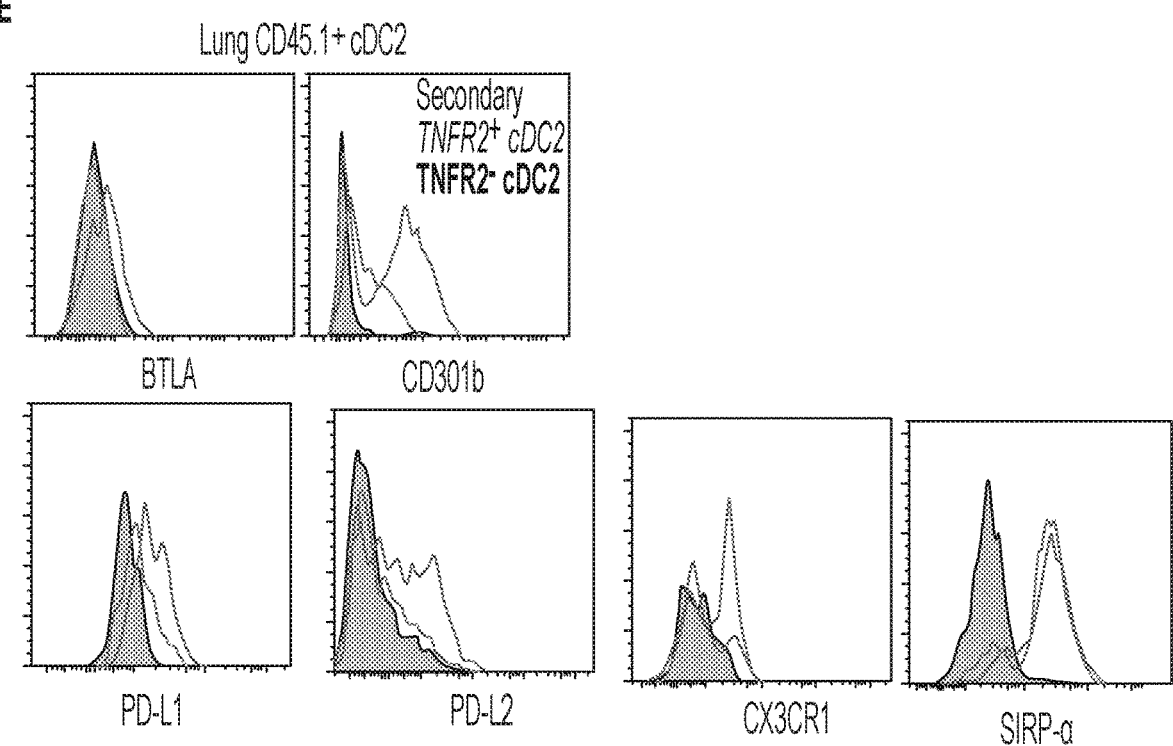
Figure 17A:
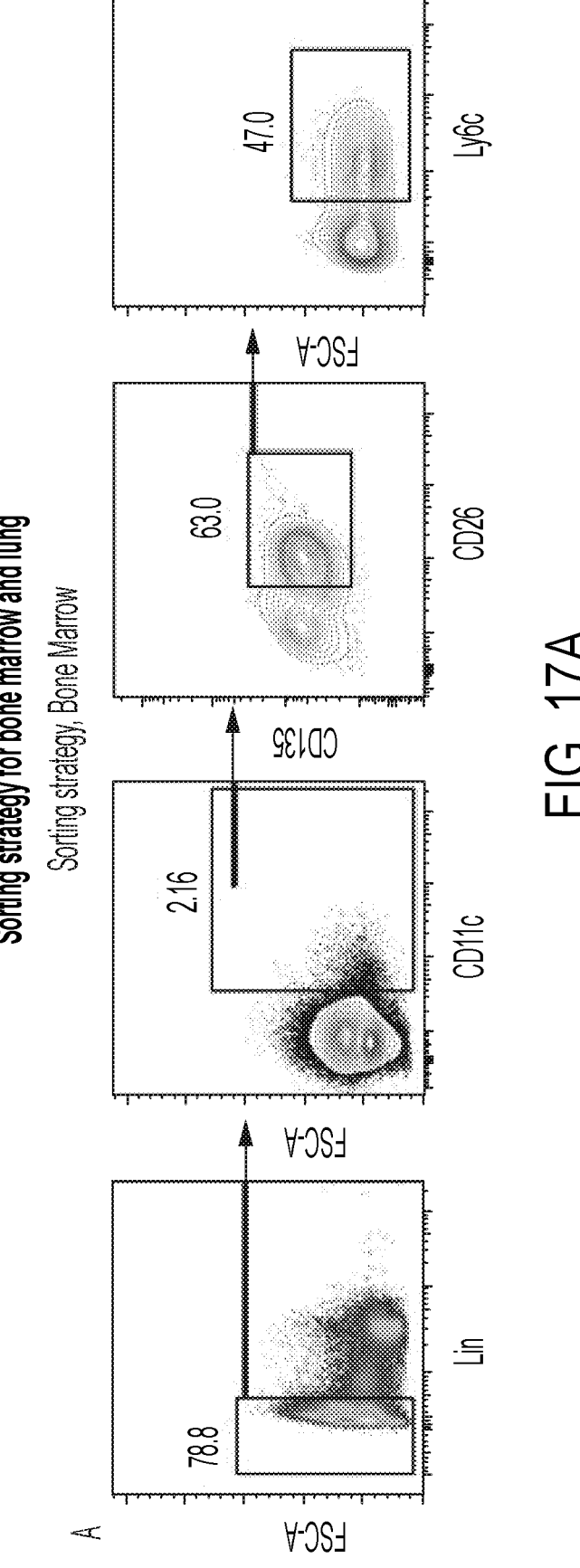
FIG. 17. A. pre-cDC2 gating strategy in the bone marrow. Naïve B6.CD45.1 mice were used. B. Experimental scheme for the transfer of pre-cDC2 into IRF4fl/flCD11ccre mice (CD45.2). C. Phenotypic analysis of CD45.1 DCs transferred into IRF4fl/flCD11ccre mice. D. Experimental scheme for the adoptive transfer of TNFR2+ and TNFR2− lung cDC2 into the MPYS−/− mice.
Figures 17B, 17C:
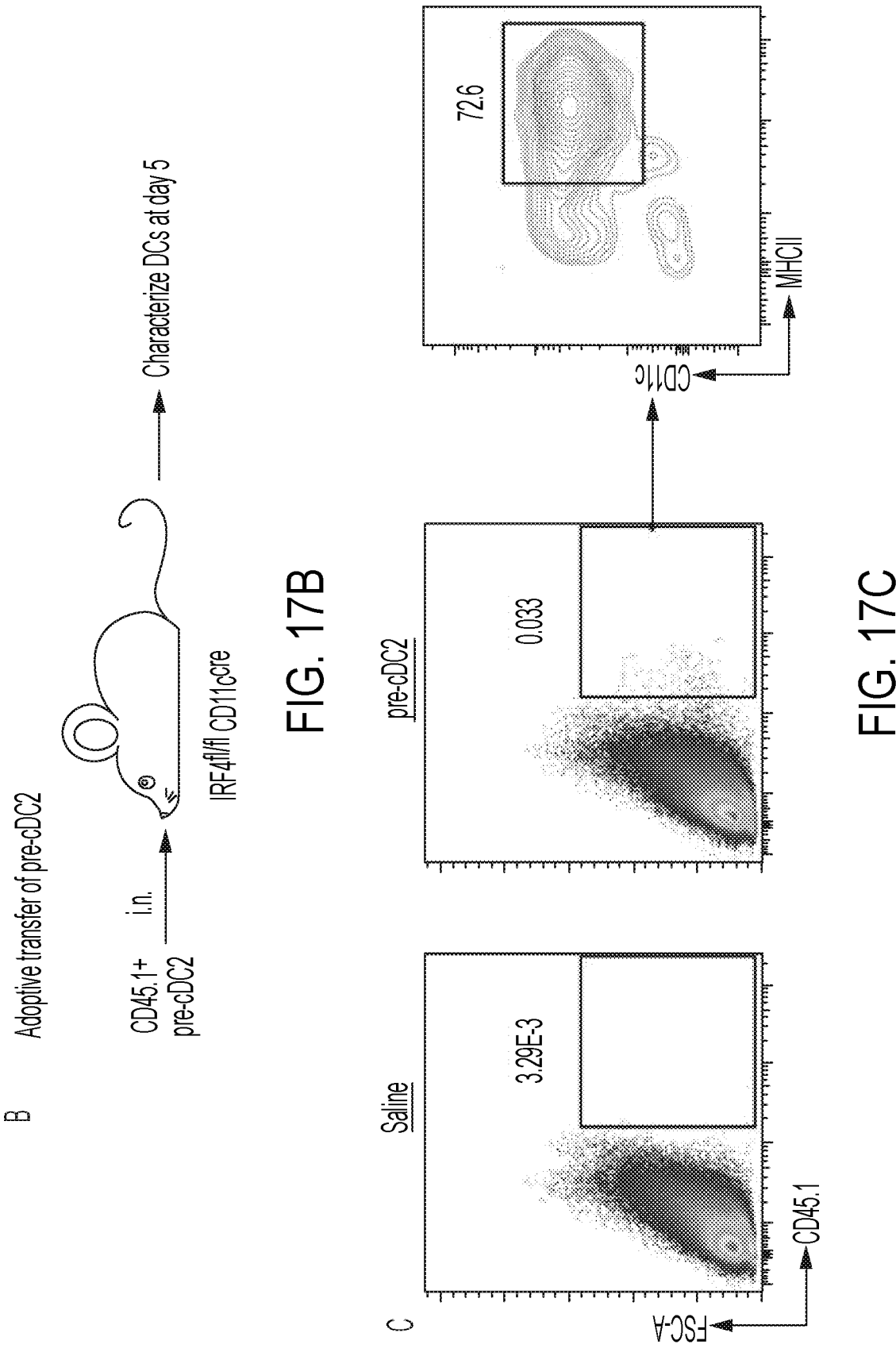

To further establish that the lung TNFR2$^+$ and TNFR2$^-$ cDC2 subset are cDC2, we adoptively transfer CD45.1 pre-cDC2[40,42] into IRF4$^{fl/fl}$CD11c$^{cre}$ mice (FIG. 17A-C). CD45.1$^+$ cells were identified in lung five days after transfer and displayed a cDC2 phenotype (FIGS. 5D and 17C). Importantly, the CD45.1$^+$ pre-cDC2 generated both TNFR2$^+$ and TNFR2$^-$ lung cDC2 in the recipient mice (FIG. 5D). The CD45.1$^+$TNFR2$^+$ cDC2 expressed BTLA, PD-L1 and had mixed expression of PD-L2 and CD301b (FIG. 5E), similar to the resident TNFR2$^+$ cDC2. The CD45.1$^+$TNFR2$^-$ cDC2 only expressed CX3CR1 (FIG. 5E). We concluded that the lung TNFR2$^+$ and TNFR2$^-$ cDC2 arise from the cDC2 lineage and express distinct surface markers.

Figure 5F:
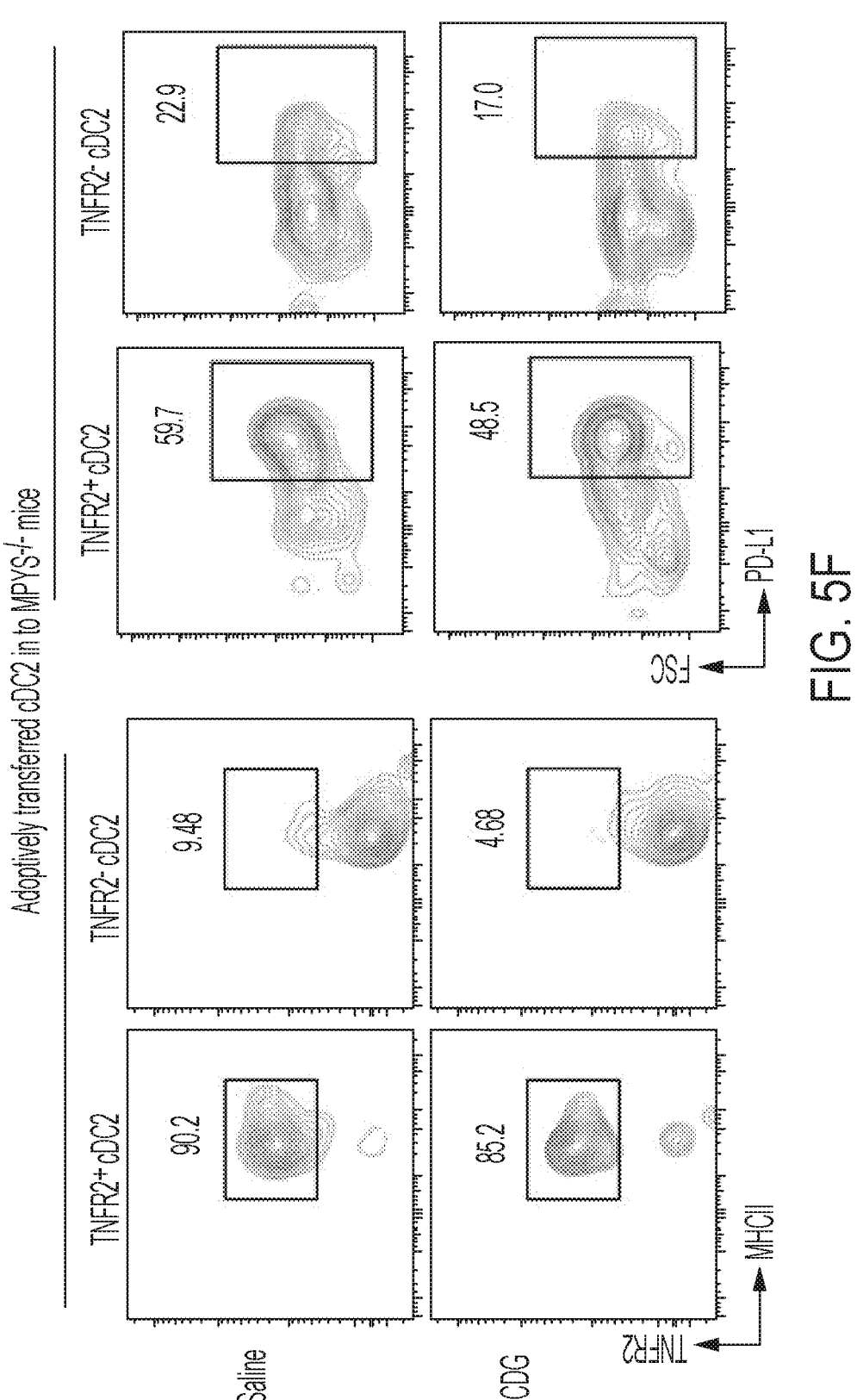
Figure 17D:
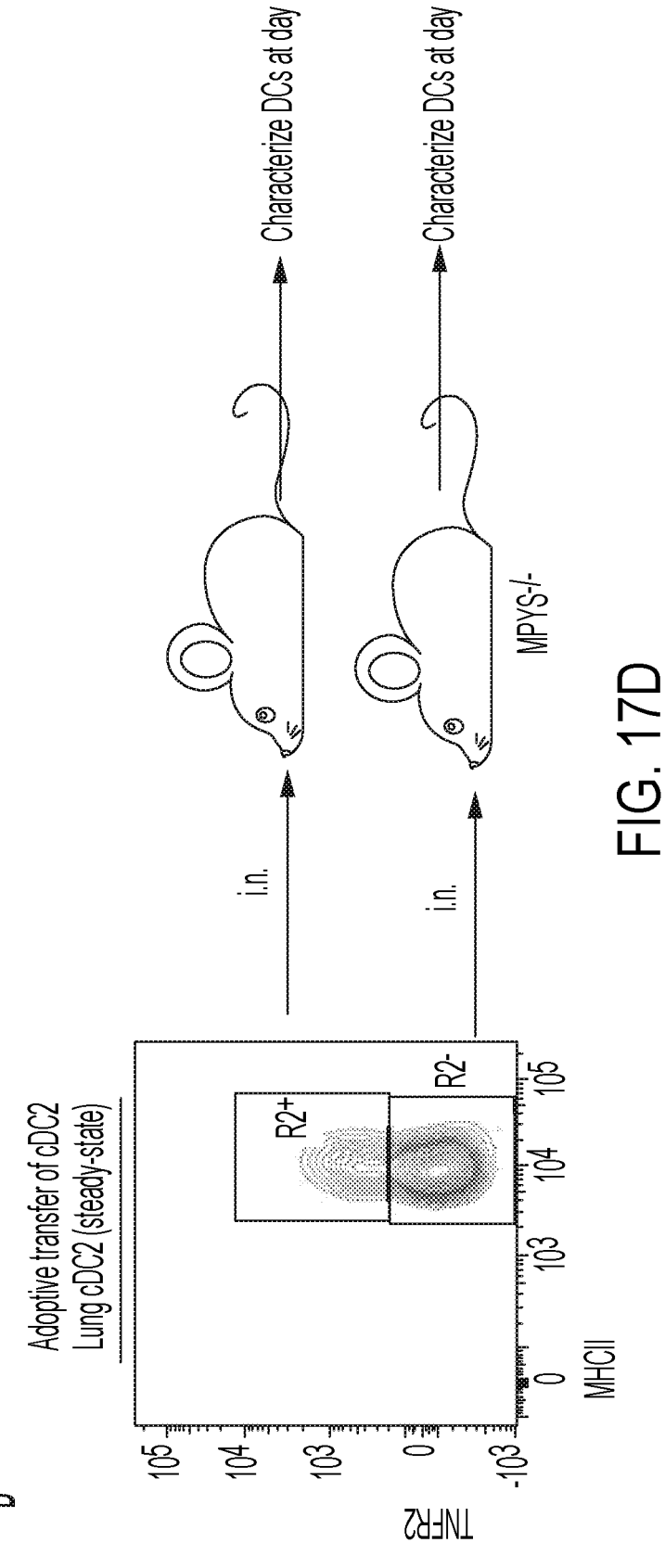
Figure 18A:
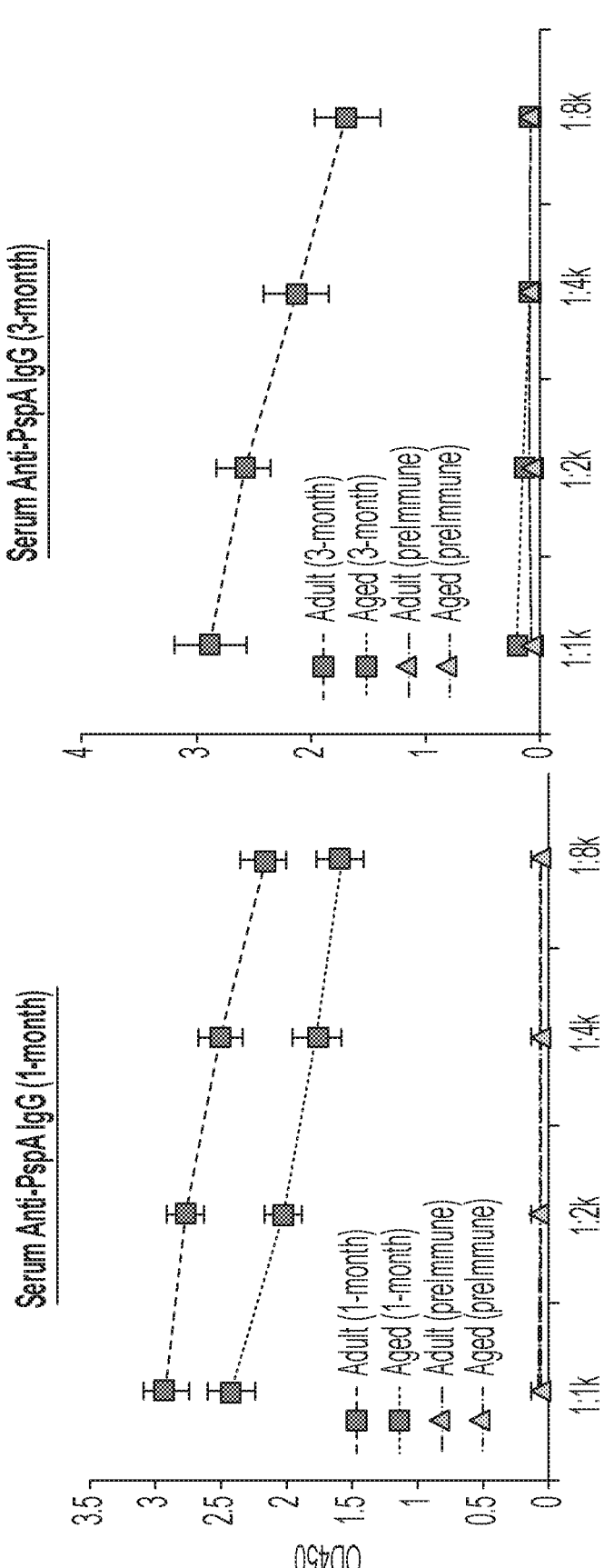
FIG. 18.A-B. 3-month old C57BL/6(Adult), 18 month old C57BL/6 (Aged) mice were immunized (i.n.) with CDG (5 µg) and PspA (2 µg) twice at 2-weeks intervals. Serum anti-PspA total IgG (FIG. 18A) and BALF anti-PspA IgA (FIG. 18B) were determined by ELISA at indicated time points after the last immunization. n=3.
FIG. 18C. Adult and aged mice were immunized or not as (FIG. 18A). One month later, mice were infected (i.n) with *S. pneumoniae* strain D39 (50×LD50,~2.5×108c.f.u). Animal health was monitored for 2-weeks. n=3.Graphs represent means+/− standard error from three independent experiments. The significance is calculated (unpaired Student's t test).
Figure 18B:
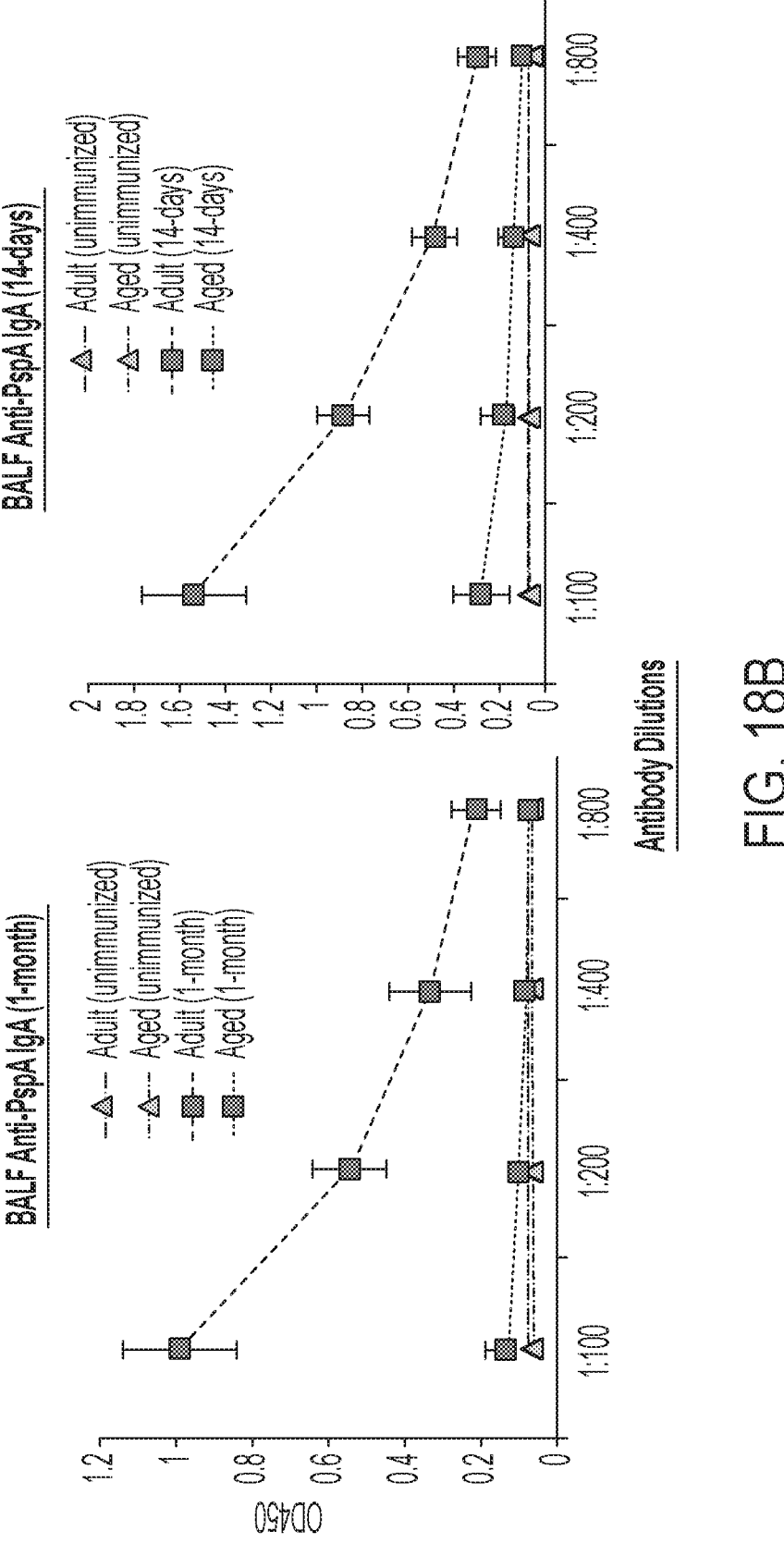
Figure 18C:
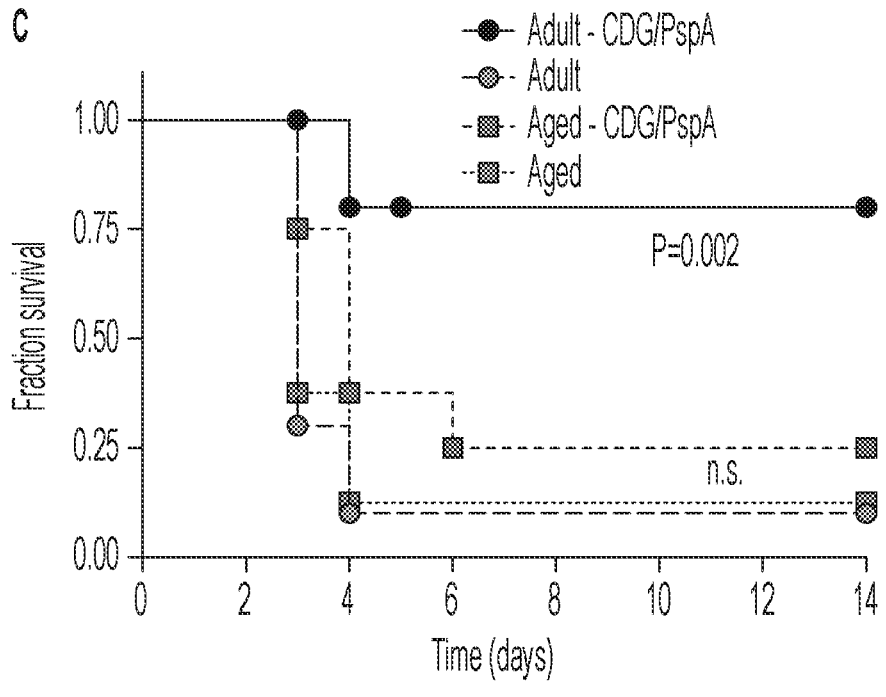
Figures 19A, 19B, 19C, 19D:
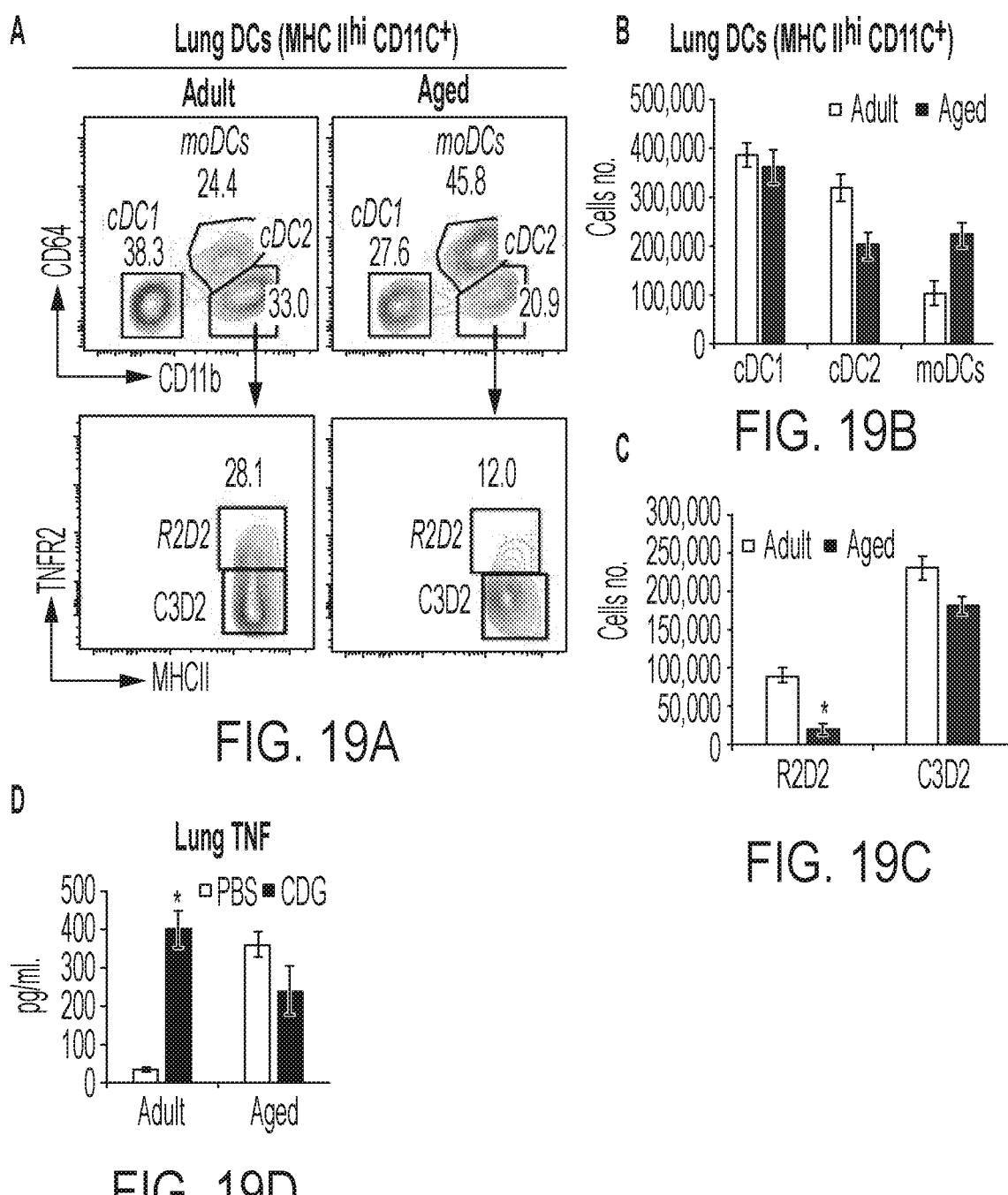
FIG. 19A. Flow analysis of lung DCs subsets from adult and aged mice. n=3.
FIG. 19B-C. Total numbers of lung DC subsets from adult and aged mice. n=3.
FIG. 19D. Adult and aged mice were treated (i.n.) with CDG (5 µg) for 20 hrs. TNF was determined in lung homogenates by ELISA. n=3. Graphs represent means±standard error from three independent experiments. The significance is represented by an asterisk (*) where p<0.05 (unpaired Student's t test).
Figure 21D:
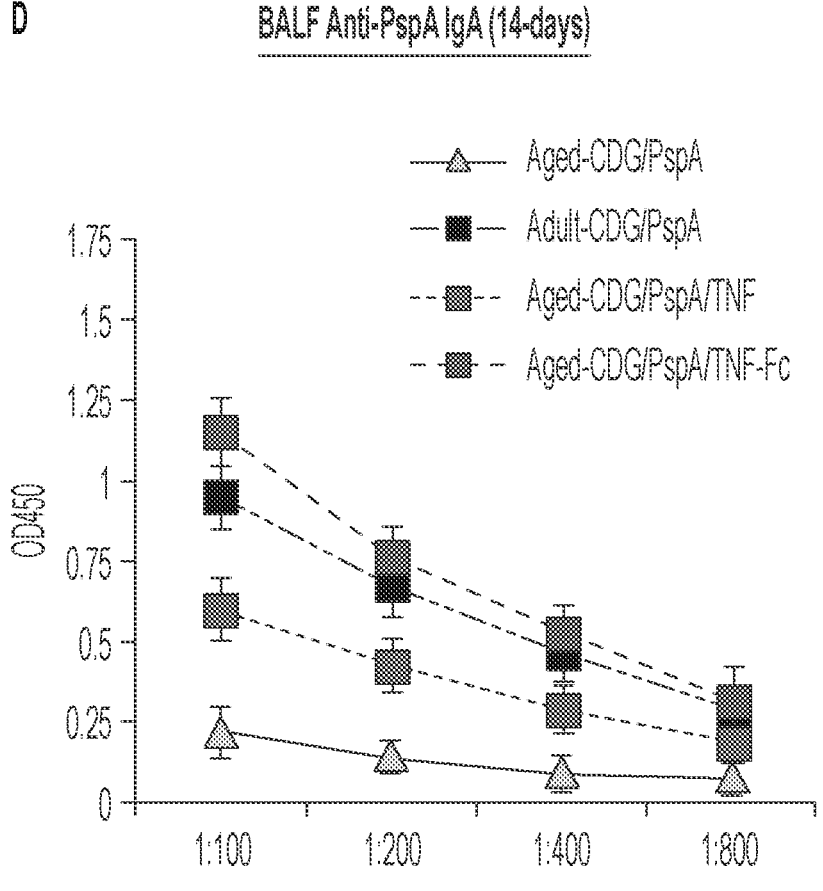
FIG. 21D. Mucosal anti-PspAIgA was examined in mice 14 days post immunization. n=3. Graphs represent means±standard error from three independent experiments.
Figure 22:
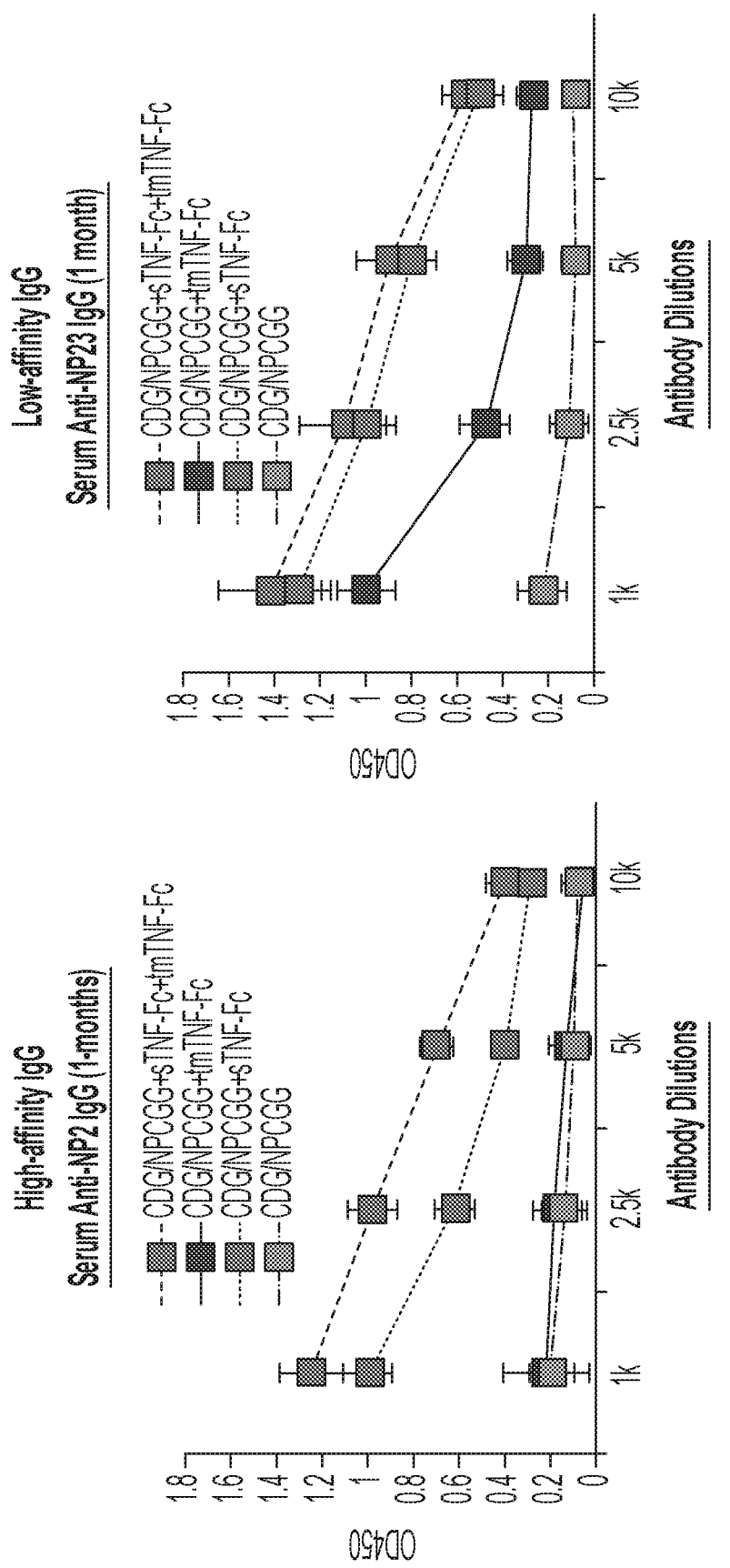
FIG. 22. Aged mice (~18 months old) were immunized (i.n.) with CDG/NP6CGG. Serum anti-NP2 (high-affinity)

We next asked if the TNFR2$^+$ and TNFR2$^-$ cDC2 populations represent different developmental/active stage of cDC2. We adoptively transferred CD45.1 lung TNFR2$^+$ and TNFR2$^-$ cDC2 into MPYS$^{-/-}$ mice (FIG. 17D). The recipient mice were then activated by CDG (i.n.). Consistent with our previous observation, TNFR2$^-$ cDC2 did not upregulate TNFR2 while TNFR2$^+$ cDC2 maintained their expression of TNFR2 (FIG. 5F). CDG treatment did not affect PD-L1 expression either (FIG. 5F). Collectively, we concluded that lung cDC2 consist of two functionally and developmentally distinct subsets, TNFR2$^+$ and TNFR2$^-$ cDC2.

CDG Activates TNFR2-Deficient cDC2 In Vivo

Figures 6A, 6B:
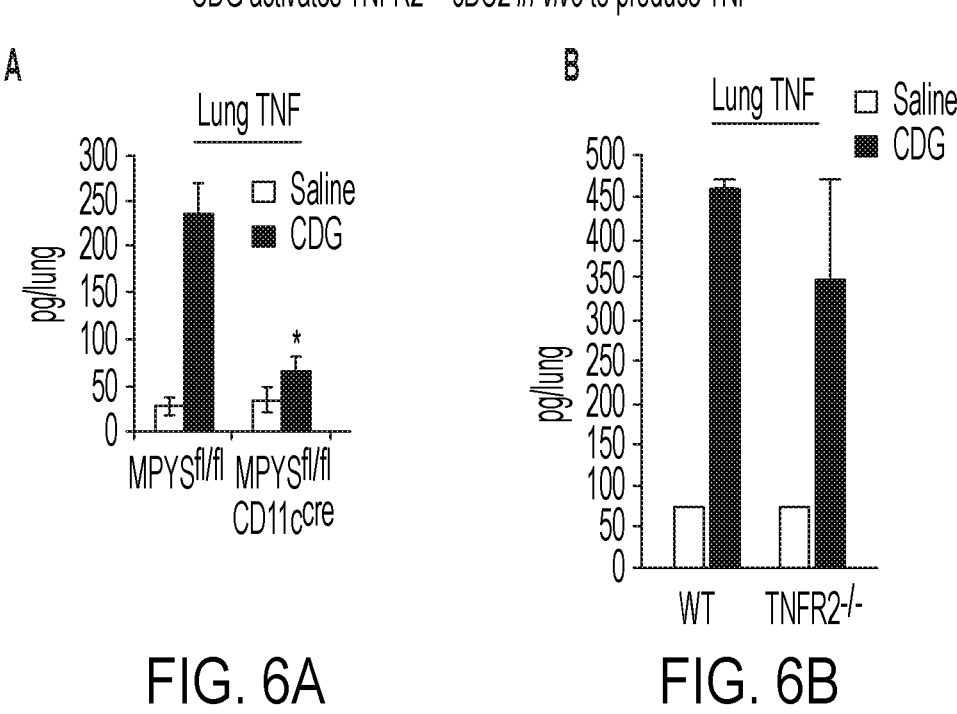
FIG. 6. CDG activates TNFR2$^{-/-}$ cDC2 in vivo to produce TNF. A-B. Indicated mice were administered (i.n.) with saline or CDG for 5 hrs. TNF production was measured in lung homogenates by ELISA. n>3. C. WT and TNFR2$^{-/-}$ mice were treated with saline or CDG for 16 hours. TNF in lung cDC2 was determined by an intracellular cytokine stain. n=3. D. TBK1$^{fl/fl}$ and TBK1$^{fl/fl}$Vav$^{cre}$ mice were administered (i.n.) with saline or CDG for 5 hrs. TNF production was measured in lung homogenates by ELISA. n=3. E. Flow cytometry analysis of p-TBK1 expression in lung cDC2 from WT and TNFR2$^{-/-}$ mice treated with saline or CDG for 16 hours. n=3. Graphs represent means±standard error from three independent experiments. The significance is represented by and asterisk (*) where p<0.05 (unpaired Student's t test).
Figure 6D:
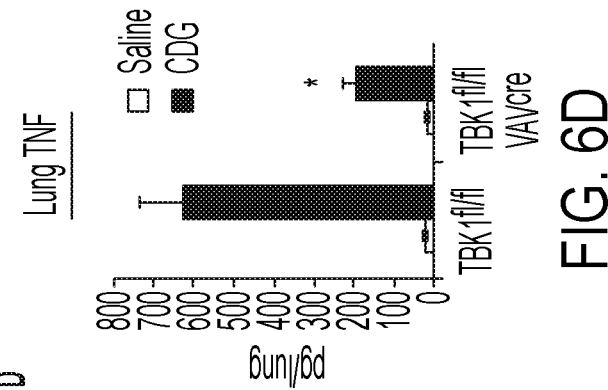
Figure 6C:
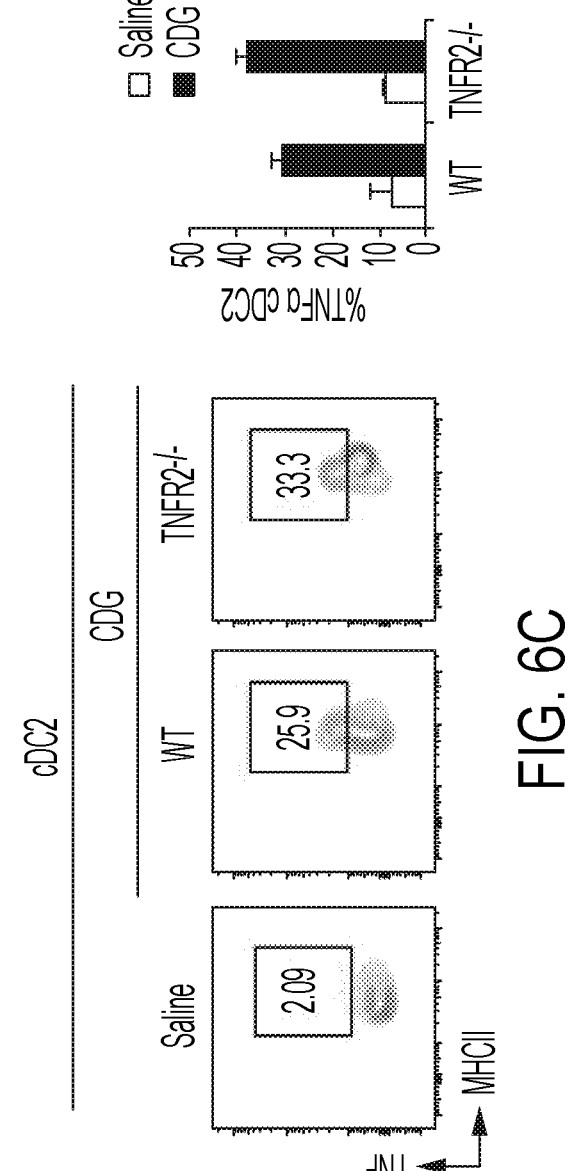
Figure 6E:
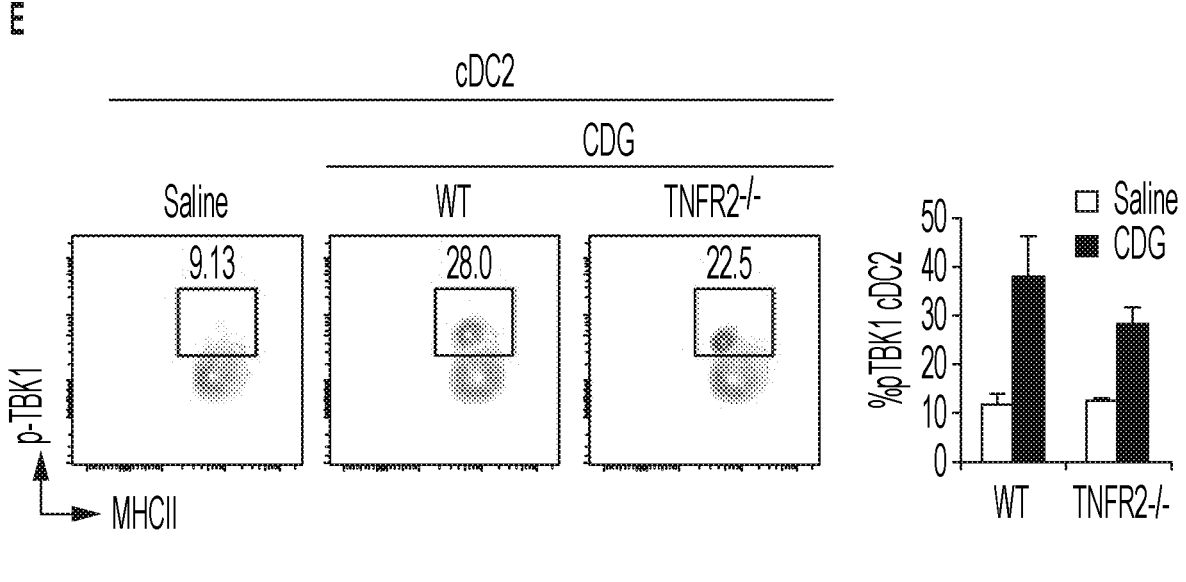

Question remains how the immature TNFR2$^-$ cDC2 mediates CDG-induced antibody responses in vivo. We suspected that the TNFR2$^-$ cDC2, though not mature, may still be activated by CDG in vivo. CDG induces TNF production in vivo that is essential for its adjuvant activity[15-17]. CDG-induced TNF production in vivo mainly depending on MPYS-expression in CD11c$^+$ cells (FIG. 6A)[17], specifically cDC2 as IRF4$^{fl/fl}$CD11c$^{cre}$ mice had dramatically decreased lung TNF (FIG. 12C). We found that CDG induced lung TNF in TNFR2$^{-/-}$ mice (FIG. 6B). Furthermore, cDC2 produced TNF in TNFR2$^{-/-}$ mice (FIG. 6C). Deleting TBK1 in hematopoietic and endothelial lineages (TBK1$^{fl/fl}$Vav$^{Cre}$) dramatically reduced CDG-induced lung TNF production (FIG. 6D) suggesting TBK1 is needed for TNF production by CDG. Indeed, TBK1 was activated in the TNFR2$^{-/-}$ cDC2 (FIG. 6E). Last, adoptive transferred TNFR2$^-$ cDC2 produced lung TNF in MPYS$^{-/-}$ lung (FIG. 4B). We concluded that although TNFR2$^-$ cDC2 fail to mature, they were activated by CDG in vivo.

Figures 7A, 7B, 7C:
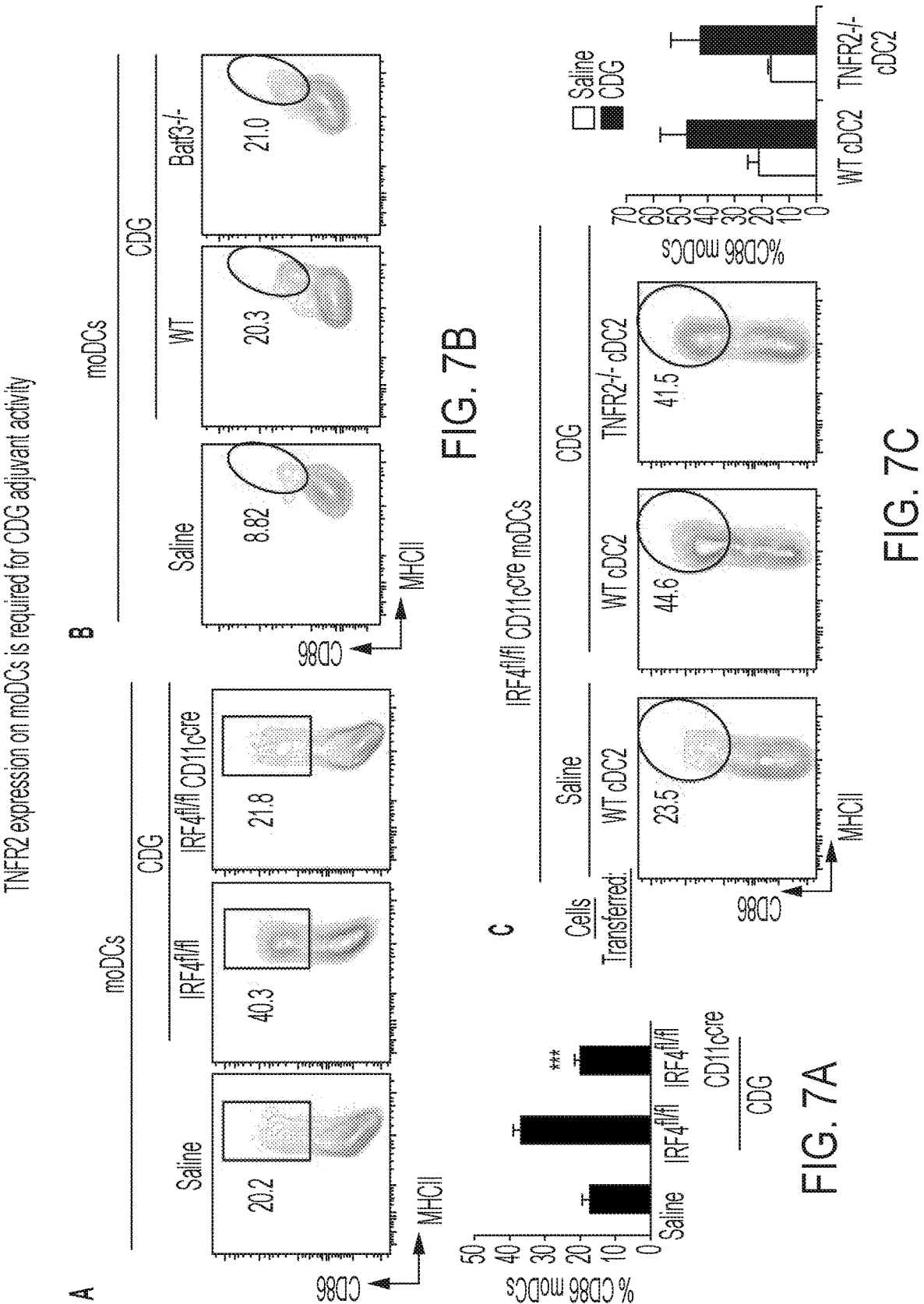
FIG. 7. TNFR2 expression on moDCs is required for CDG adjuvant activity. A-B. WT, IRF4$^{fl/fl}$CD11$^{cre}$ (A) and Batf3$^{-/-}$ (B) mice were treated (i.n.) with saline or CDG (5 μg) for 16 hours. CD86 expression in lung moDC were determined by Flow cytometry. n=3. C. WT and TNFR2$^{-/-}$ cDC2 were adoptively transferred into the IRF4$^{fl/fl}$CD11c$^{cre}$ mice. The mice were treated with CDG (i.n.) for 16 hrs. CD86 expression on endogenous moDC were examined by Flow cytometry. n=3. D. Flow cytometry analysis of CD86 expression on lung moDCs in RelB$^{fl/fl}$ and RelB$^{fl/fl}$CD11c$^{Cre}$ mice treated with CDG for 16 hrs. n=3. E. Flow cytometry analysis of TNFR2 expression on lung moDC of WT mice treated (i.n.) with saline or CDG for 16 hrs. n=3. F. Flow cytometry analysis of CD86 expression on lung moDCs from WT or TNFR2$^{-/-}$ mice treated (i.n.) with saline or CDG for 16 hrs. n=3. G. WT, TNFR2$^{-/-}$ mice or TNFR2$^{-/-}$ mice receiving (i.n.) WT monocytes or TNFR2$^{-/-}$ monoctyes were immunized with CDG/PspA. Serum anti-PspA IgG and BALF anti-PspA IgA were determined by ELISA. n=3. H. WT cDC2 adoptively transferred into TNFR2$^{-/-}$ mice were immunized with CDG/PspA. Serum anti-PspA IgG were determined by ELISA. n=3. Graphs represent means±standard error from three independent experiments. The significance is represented by and asterisk (*) where p<0.05 (unpaired Student's t test).
Figures 7D, 7E:
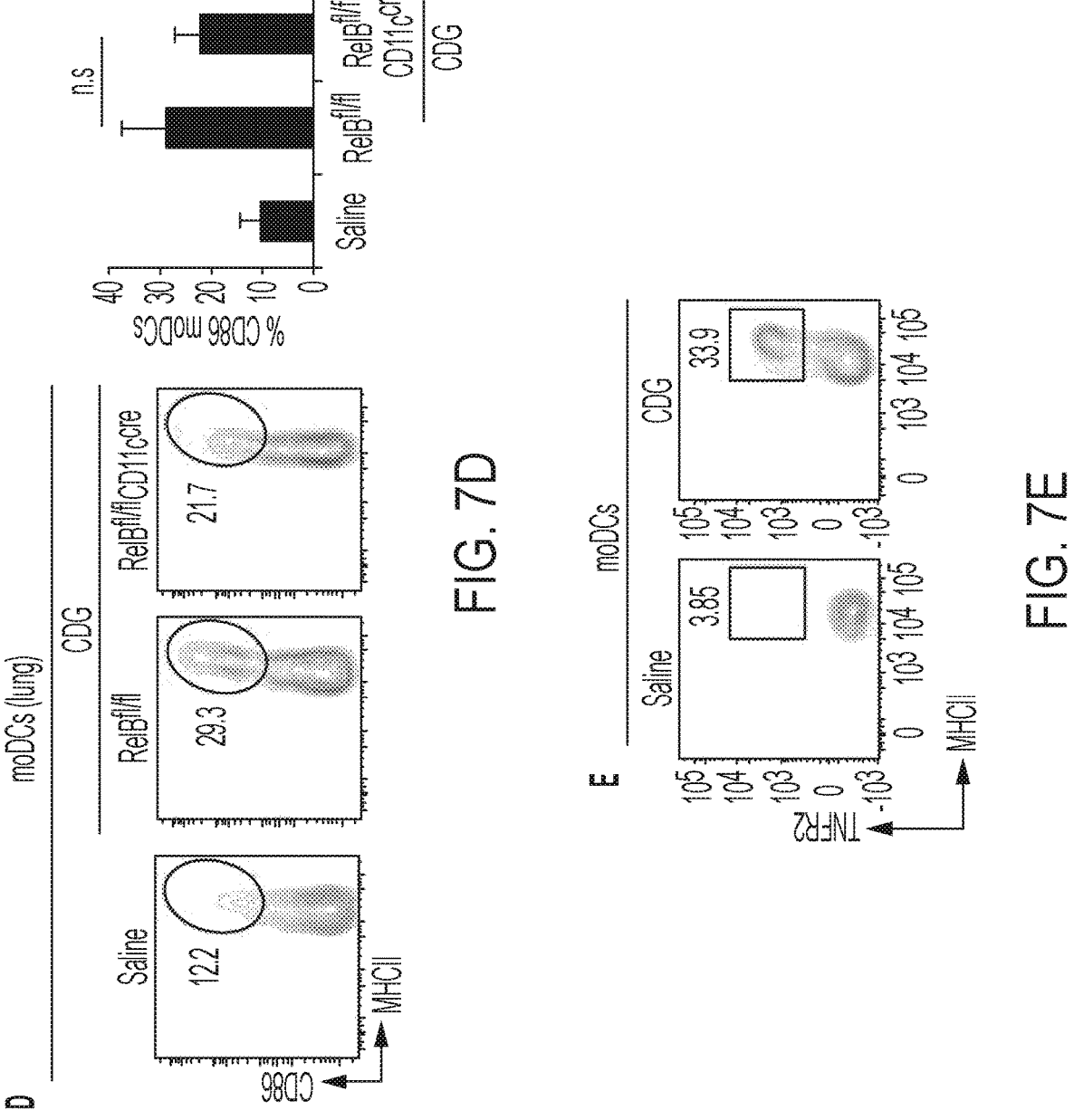

Adoptive Transfer of WT Monocyte Restored CDG Adjuvant Activity in TNFR2$^{-/-}$ Mice We next investigated how the activated, but immature, TNFR2$^-$ cDC2 mediate CDG-induced antibody responses. First, we found that moDCs failed to upregulate CD86 in IRF4$^{fl/fl}$CD11c$^{cre}$ mice following CDG treatment (FIG. 7A). The CD86 expression in Batf3$^{-/-}$ mice was unaltered (FIG. 7B). Second, adoptively transferred TNFR2$^{-/-}$ cDC2 induced CD86 expression on moDCs in IRF4$^{fl/fl}$CD11c$^{cre}$ mice (FIG. 7C). Third, CDG induced CD86 expression on moDCs in RelB$^{fl/fl}$CD11c$^{cre}$ mice (FIG. 7D). We concluded that cDC2, especially TNFR2$^-$ cDC2 promote CDG-induced moDCs maturation in vivo.

Figure 7F:
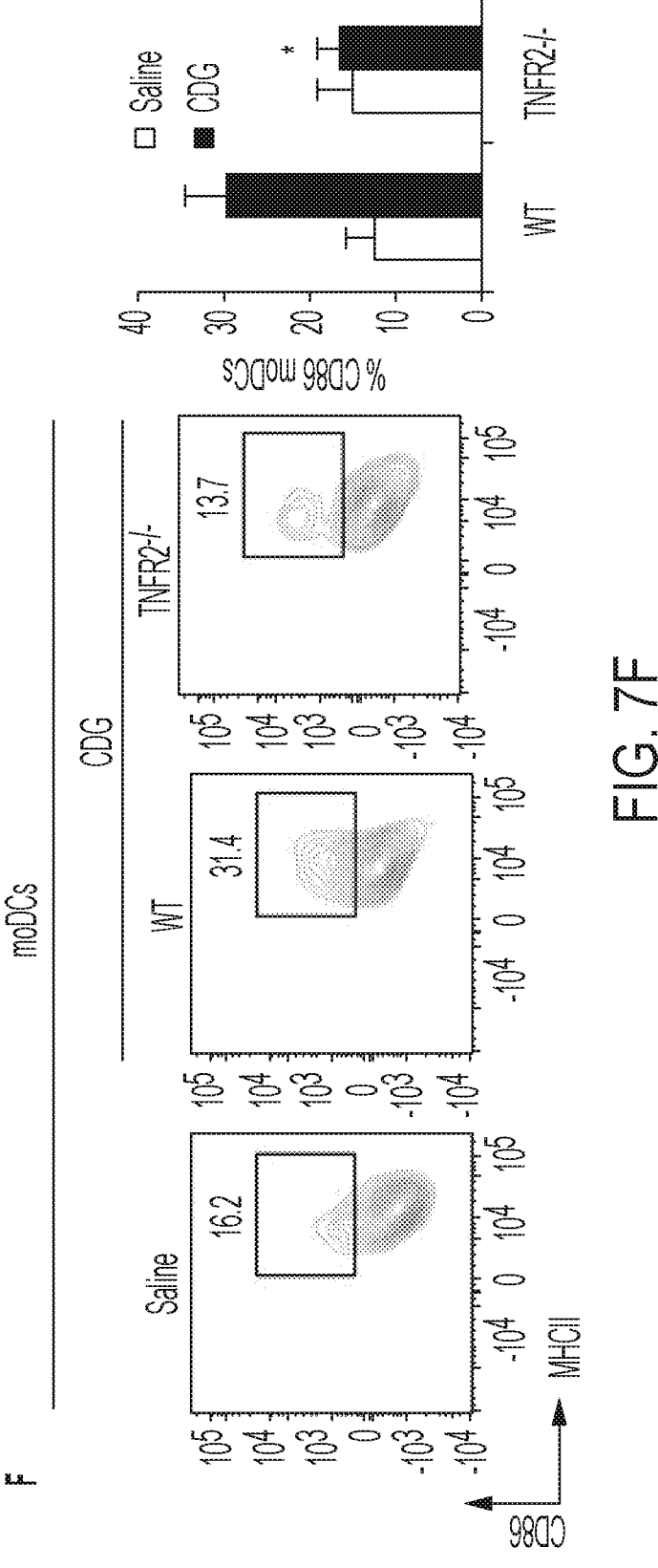
Figures 7G, 7H:
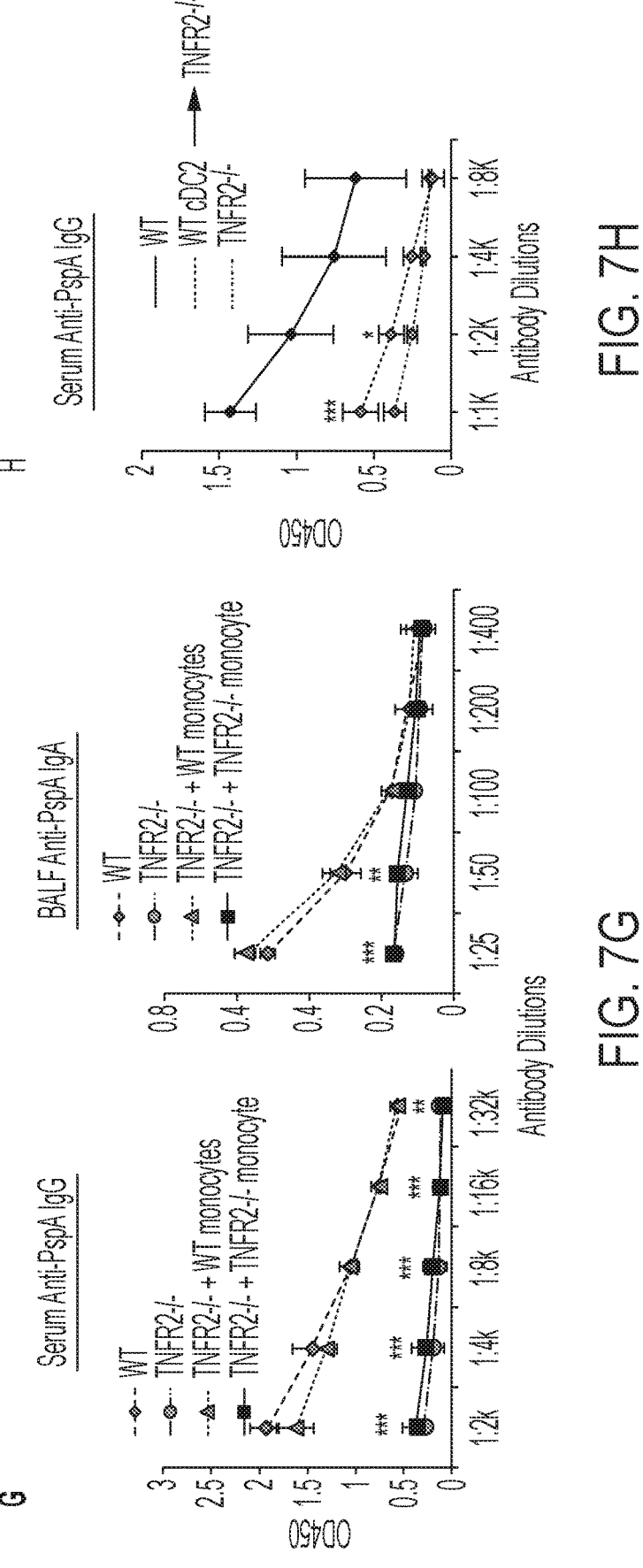

Adoptively transferred TNFR2$^{-/-}$ cDC2 restored CDG responses in IRF4$^{fl/fl}$CD11c$^{cre}$ mice (FIG. 3A). Yet, TNFR2$^{-/-}$ mice had no CDG responses (FIG. 2A). We reasoned that TNFR2 expression on moDCs may be important for CDG responses in vivo. Indeed, we found that CDG induced TNFR2 on moDCs in WT mice (FIG. 7E) and moDCs from TNFR2$^{-/-}$ mice did not upregulate CD86 in response to CDG in vivo (FIG. 7F). Last, adoptive transfer of WT monocytes into TNFR2$^{-/-}$ mice restored CDG-induced IgG and IgA responses (FIG. 7G). Notably, adoptive transfer WT cDC2 into TNFR2$^{-/-}$ mice did not restore CDG-induced antibody responses (FIG. 7H). We concluded that moDCs expression of TNFR2 is critical for its maturation and subsequent induction of CDG adjuvant response.

CDG Induces mTNF Expression on TNFR2$^-$ cDC2 In Vivo

Our data so far indicates that moDCs are matured by activated TNFR2$^-$ cDC2. Furthermore, moDC maturation requires cell intrinsic TNFR2 expression. Only mTNF can efficiently engage TNFR2[36]. Both TNFR2$^+$ and TNFR2$^-$ cDC2 produced TNF upon intranasal CDG treatment (FIG. 4B). We asked if the lung TNFR2$^-$ cDC2 specifically expressed mTNF.

Figure 8A:
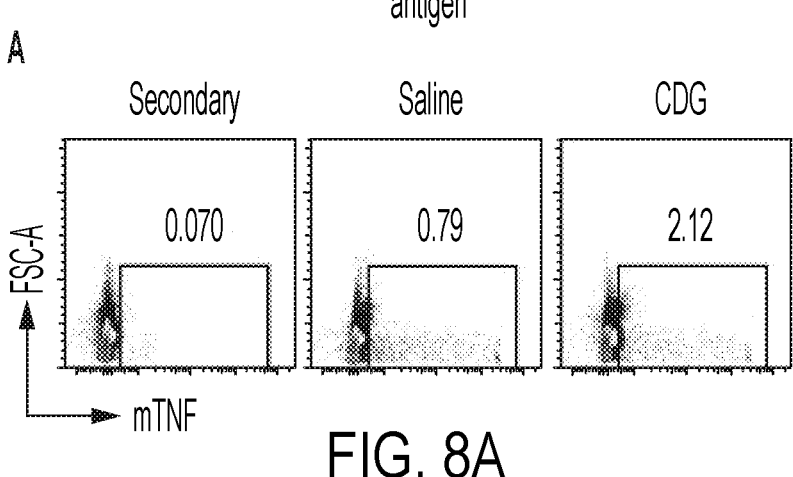
FIG. 8. TNFR2$^-$ cDC2 express mTNF but have few processed antigen. A. WT mice were administered with saline or CDG (5 μg) for 16 hrs. mTNF expression was determined by Flow cytometry using mouse TNFR2$^-$ Fc recombinant protein. n=3. B-C. Flow cytometry analysis of mTNF expression in lung DCs (B) and cDC2 (C) n=3. D. Flow cytometry analysis of antigen uptake and processing in lung CD11b$^+$ DC from WT mice treated (i.n.) with DQ-OVA (20 ug) and CDG (5 ug) for 16 hours. n=3. Graphs represent means±standard error from three independent experiments. The significance is represented by and asterisk (*) where p<0.05 (unpaired Student's t test).
Figures 8B, 8C:
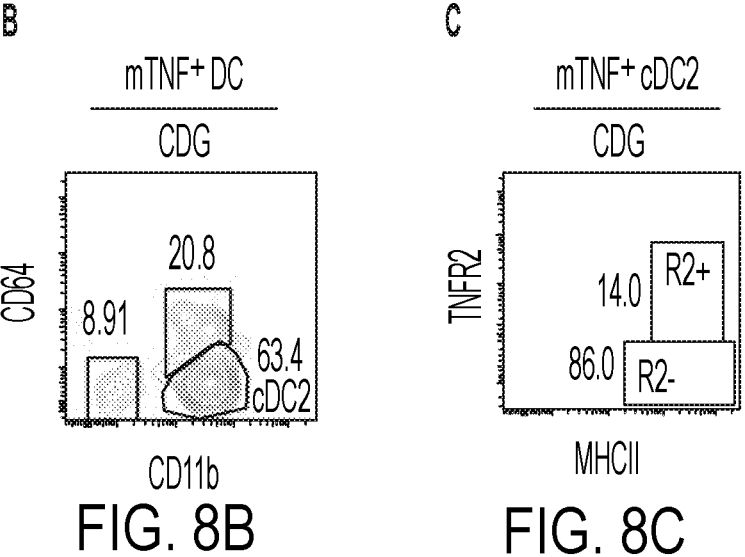

We intranasally administered CDG to WT mice for 16 hours and detected cell surface mTNF expression using TNFR2$^-$ Fc recombinant protein (FIG. 8A). We found that the majority of lung mTNF$^+$ DCs were cDC2 (FIG. 8B). Remarkably, TNFR2$^-$ cDC2 were the main mTNF$^+$ cDC2 cells in vivo while TNFR2$^+$ cDC2 expressed little mTNF (FIG. 8C).

moDCs, not TNFR2$^-$ cDC2, are Very Efficient in Antigen Processing In Vivo

We next examined antigen processing in TNFR2$^-$ cDC2 in vivo. WT mice were intranasally administered with CDG/DQ™-OVA[17]. DQ$^+$ cells were examined in lung cDC2 and moDCs (FIG. 8D). DQ™-OVA is a self-quenched conjugate of OVA exhibiting bright green fluorescence upon proteolytic degradation (DQ-Green). Furthermore, high concentration of digested fragments of DQ™-OVA accumulating in organelles form excimers that exhibits bright red fluorescence (DQ-Red). We found that DQ$^+$ moDCs are mostly DQ-Red indicating a high concentration of processed antigens in moDCs. Conversely, DQ$^+$ cDC2 were DQ-Green (FIG. 8D). Strikingly, comparing to the TNFR2$^+$ cDC2 subset, very few TNFR2$^-$ cDC2 subset were DQ$^+$ (FIG. 8D) suggesting that the TNFR2$^-$ cDC2 either did not take up antigen or were not efficient at antigen processing. In comparison, all DQ$^+$ moDCs were TNFR2$^+$ cells (FIG. 8D) indicating TNFR2$^+$ moDCs were indeed mature DCs.

moDCs Promote CDG-Induced Tfh and GC B Cells Generation in the Lung

Figures 9A, 9B, 9C:
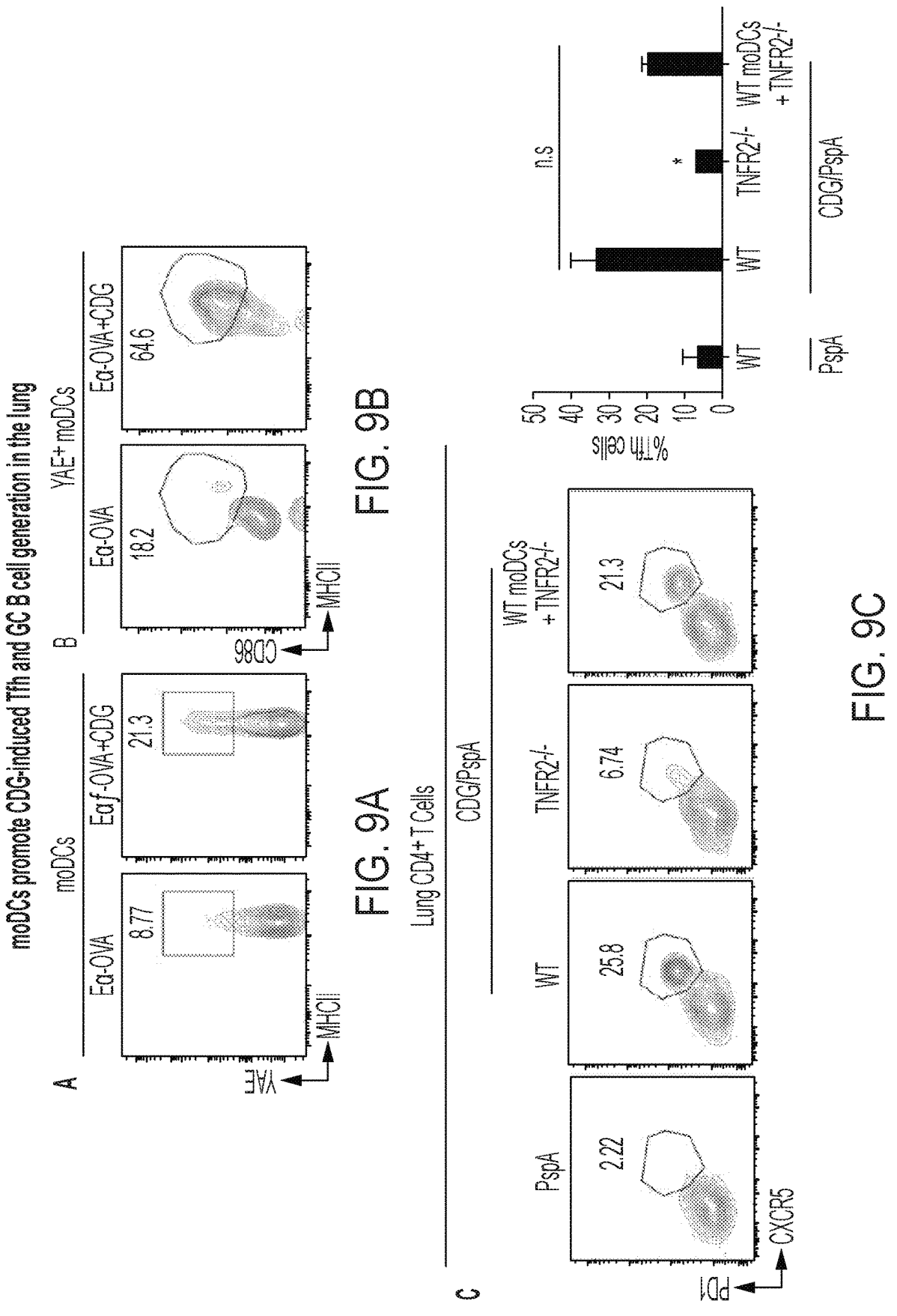
FIG. 9: moDCs promote CDG-induced Tfh and GC B cell generation in the lung. A-B. WT mice were administered with Ea-OVA (10 μg) or Ea-OVA/CDG (5 μg) for 16 hrs. YAE$^+$ moDCs (A) and CD86$^+$YAE$^+$ moDCs were determined by Flow cytometry. n=3. C-D. WT, TNFR2$^{-/-}$ mice or TNFR2$^{-/-}$ mice receiving (i.n.) WT monocytes were immunized with CDG/PspA. At Day 14, CD4$^+$PD1$^+$ CXCR5$^+$ Tfh (C) and CD19$^+$ Bcl6$^+$ B cells (D) were determine in lung by flow cytometry. n=3. E. TNFR2$^+$ and TNFR2$^-$ cDC2 were adoptively transferred into IRF4$^{fl/fl}$CD11c$^{cre}$ mice and immunized with CDG/PspA. At Day 14, CD4$^+$ Bcl6$^+$ Tfh were determine by flow cytometry. n=3. F. Model: following CDG administration, TNFR2$^-$ cDC2 produce mTNF to activate moDCs, which will generate Tfh to mediate the antibody response. Graphs represent means±standard error from three independent experiments. The significance is represented by and asterisk (*) where p<0.05 (unpaired Student's t test).

How does non-migratory moDCs (FIGS. 1D & 12B)[25,33] promote CDG-induced antibody responses? moDCs were efficient at antigen processing (FIG. 8D). We first asked if they presented antigen on cell surface. We intranasally administered C57BL/6 mice with CDG and Eα-OVA, and detected I-A$^b$/Eα$^+$ cells with the YAE mAb. Indeed, CDG increased YAE$^+$ moDCs in vivo (FIG. 9A). Furthermore, the majority of YAE$^+$ moDCs upregulated CD86 (FIG. 9B), indicating their potential to activate CD4$^+$ T cells.

Figures 9D, 9E:
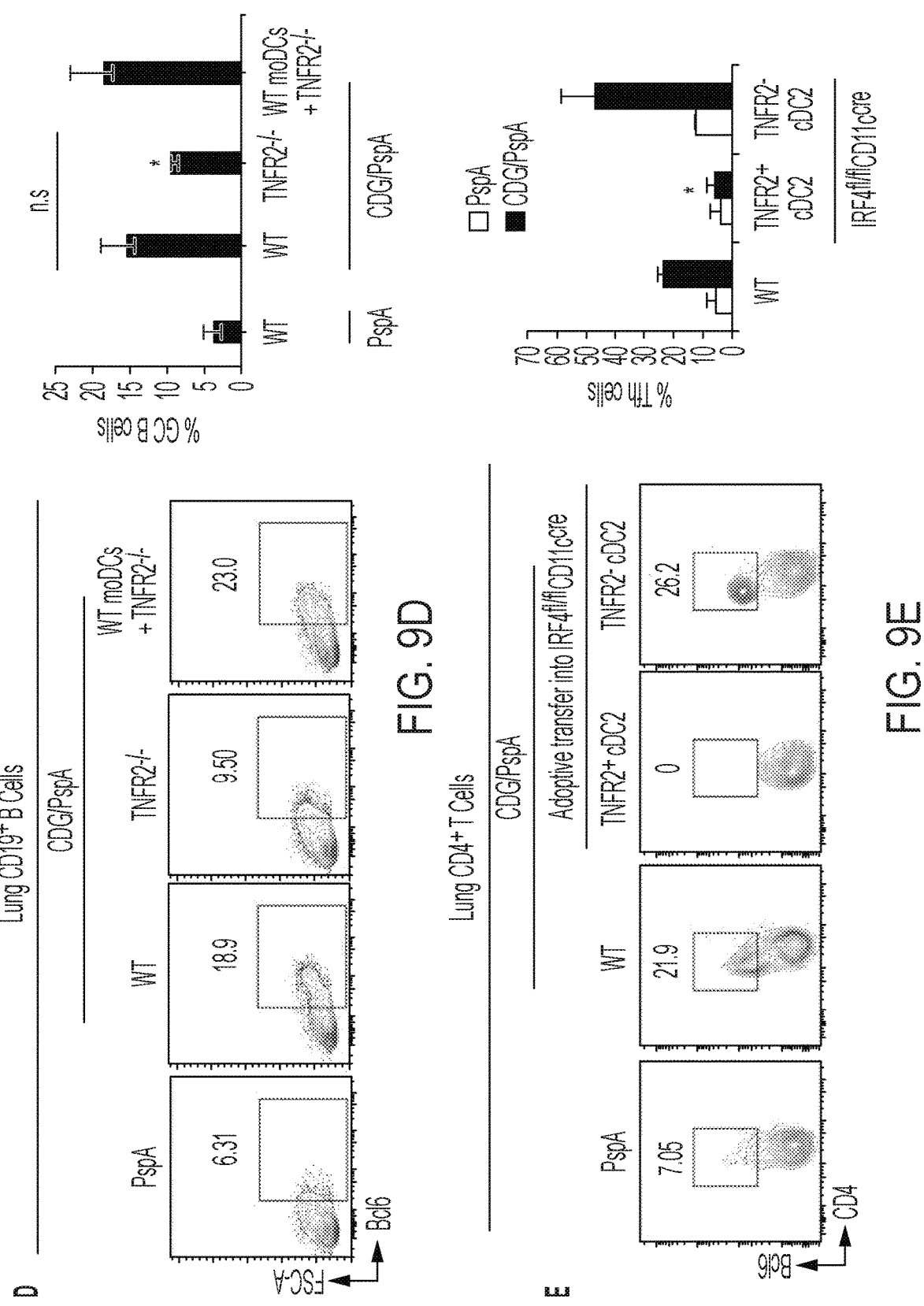
Figure 9F:
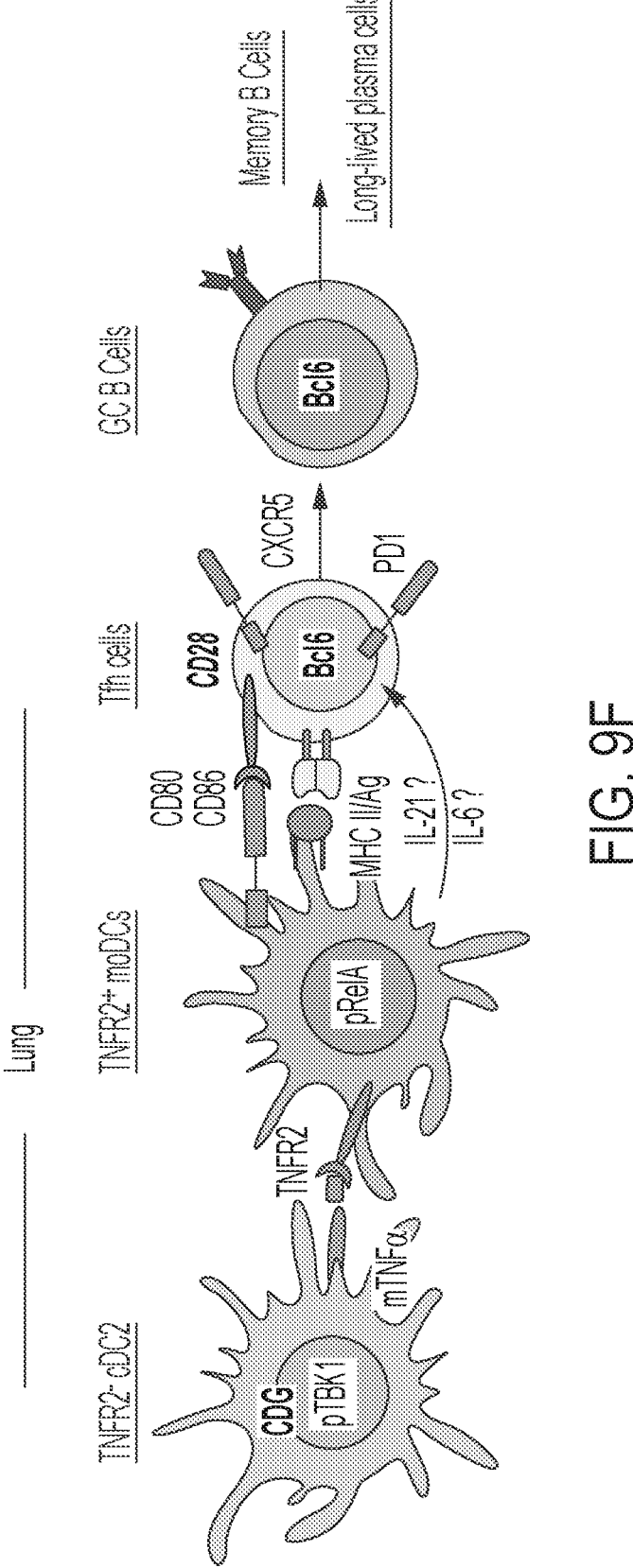

Tfh cells and GC B cells play central roles in promoting humoral responses. We found that 14 days after CDG/PspA immunization (i.n.), lung from the WT mice had PD1$^+$ CXCR5$^+$ Bcl6$^+$ Tfh cells and Bcl6$^+$ GC B cells (FIG. 9C-9E). In contrast, TNFR2$^{-/-}$ mice were unable to generate lung Tfh or GC B cells (FIG. 9C-9D). Importantly, adoptively transfer of WT monocytes into TNFR2$^{-/-}$ mice restored the generation of Tfh and GC B cells in the lung (FIG. 9C-9D). We concluded that moDCs promote CDG-induced Tfh and GC B cells generation in the lung.

moDCs are activated by TNFR2$^-$ cDC2. Thus restoring TNFR2$^-$ cDC2 in the IRF4$^{fl/fl}$CD11c$^{cre}$ mice should restore Tfh cells. Indeed, we found that adoptive transfer of TNFR2$^-$ cDC2, but not TNFR2$^+$ cDC2, into IRF4$^{fl/fl}$CD11c$^{cre}$ mice generated Tfh cells (FIG. 9E). Together, we propose that CDG activates TNFR2$^-$ cDC2 that matures moDCs to generate Tfh and GC B cells promoting CDG-induced antibody responses in vivo (FIG. 9F).

Materials and Methods

Mice

Eight to sixteen-week old mice, both males, and females, were used for all experiments. MPYS$^{-/-}$ mice (Tmem173$^{<tm1Camb>}$) have been described previously[38, 39]. The following strains were obtained from The Jackson Laboratory: Irf4$^{fl}$ (#009380)[40], Batf3$^{-/-}$ (#013755)[30], Tnfr1$^-$ (#002818)[41], Tnfr2$^-$ (#002620)[42], RelB$^{fl}$ (#028719)[43], CD11C$^{cre}$ (#008068)[44]. Vav$^{cre}$-TBK1$^{fl/fl}$ mice were from Dr. Fitzgerald's lab. All mice are on a C57BL/6 background. Mice were housed and bred in the Animal Research Facility at Albany Medical College and the University of Florida. All experiments with mice were performed by the regulations and approval of the Institutional Animal Care and Use Committee from Albany Medical College or the University of Florida.

Reagent

The following reagent was obtained through BEI Resources, NIAID, NIH: *Streptococcus pneumoniae* Family 1, Clade 2 Pneumococcal Surface Protein A (PspA UAB055) with C-Terminal Histidine Tag, Recombinant from *Escherichia coli*, NR-33178.

Intranasal CDG Immunization

Groups of mice (4 per group) were intranasally vaccinated with CDG (5 μg, Invivogen, cat #vac-cdg) adjuvanted PspA (2 μg, BEI Resources) or PspA alone[17]. Mice were immunized twice at 14 days interval. For intranasal vaccination, animals were anesthetized using isoflurane in an E-Z Anesthesia system (Euthanex Corp, Palmer, Pa.). PspA, with or without CDG was administered in 20 μl saline. Sera were collected 14 days after the last immunization. The PspA-specific Abs were determined by ELISA. Secondary Abs used were anti-mouse IgG1-HRP (Southern Biotech, cat #1070-05), anti-mouse IgG2C-HRP (Southern Biotech, cat #1079-05), and anti-mouse IgA-HRP (Southern Biotech, cat #1040-05). To determine Ag-specific Th response, spleno-cytes from PspA or CDG+PspA immunized mice were stimulated with 5 μg/ml PspA for four days in culture. Th1, Th2, and Th17 cytokines were measured in the supernatant by ELISA.

Detection of Lung TNF Production

Mice were intranasally administered 5 μg CDG, then sacrificed after 5 hrs by C02 asphyxiation[17]. Lungs were perfused with cold PBS. The harvested lungs were washed with PBS once, then stored in 0.7 ml Tissue protein extrac-tion reagent (T-PER) (Thermo Scientific, cat #78510) con-taining protease inhibitors (Roche, cat #11836153001) at −80° C. Later, the lung was thawed on ice and homogenized with Minilys® (Precellys, 5,000 RPM for 30 sec) using Precellys lysing kit (Precellys, cat #KT03961). Lung homo-genates were transferred to a 1.5 ml tube and spun at 14,000 g for 30 min at 4° C. The supernatant was collected and analyzed for TNF production by ELISA (eBioscience, cat #88-7324).

In Vivo TNFR2 Neutralization

Mice were first given CDG (i.n.). Half an hour later, treated mice were administered (i.n.) with 50 μg/50 μl anti-TNFR2 Ab (BioLegend, TR75-32.4), or isotype control (BioLegend, HTK888). Lung was harvested 16 hr later and analyzed by Flow cytometer.

Isolation of Lung Cells

Mice were intranasally administered with or without CDG (5 μg, vaccine-grade). After 20 hrs, the lungs were lavaged and perfused with ice-cold PBS. Excised lungs were digested in DMEM containing 200 μg/ml DNase I (Roche, 10104159001), 25 μg/ml Liberase TM (Roche, 05401119001) at 37° C. for 3 hrs. Red blood cells were then lysed and a single cell suspension was prepared and ana-lyzed by BD™ LSR II and FACScan flow cytometry.

In vivo Ag Uptake and Processing

Mice were intranasally administered 20 μg DQ™-Oval-bumin (DQ-OVA) (Life technologies, D12053) with, or without CDG (5 μg, vaccine-grade). After 20 hrs, the lungs were lavaged, perfused and harvested. Lung cells were analyzed by BD™ LSR II and FACScan flow cytometry.

Flow Cytometry and Cell Sorting

The following Abs from Biolegend were used in the flow cytometry: CD80 (16-10A1), CD86 (GL1), CD11B (M1/70), CD11C (N418), FcεRIa (MAR-1), MHC II (M5/114.15.2), CD103(2E7), CD24 (m1/69), CD64 (x54-5/7.1), CCR7 (4B12), TNF (MP6-XT22), TNFR2 (TR75-89), PD-L1 (10F.9G2), BTLA (8F4), PD-L2 (TY25), CD301b (URA-1), CX3CR1 (SA011F11), CD172a (P84), CD44 (IM7). The following Abs were from Cell Signaling: p-TBK1 (ser172, d52c2), p-RelB (ser552, d41b9), p-RelA (ser536, cat #4887S). The following reagents were from Sino Biological: TNFR2 Ab (cat #50128-R112-A), TNFR2-Fc (mouse TNFR2 extracellular domain, Met 1-Gly 258, was fused with the Fc region of human IgG1 at the C-ter-minus, cat #50128-M02H), human IgG1 Fc (cat #10702-HNAH). Alexa Fluor®488 mouse anti-human IgG1 Fc was from Invitrogen (cat #A-10631). FITC-CDG (2′-Fluo-AHC-CDG) was from Biolog (cat #F009). Cell sorting was performed on the BD FACSAriaIII Flow Cytometer and Cell Sorter. After sorting, dendritic cells were CFSE labeled, according to the protocol from the manufacturer (Invitro-gen).

Intracellular Staining

The intracellular cytokine staining was performed using the Cytofix/Cytoperm™ kit from BD Biosciences (cat #555028). Briefly, mice were intranasally administered saline or cyclic di-GMP (5 μg, vaccine-grade). The lungs were lavaged, perfused, and harvested at 5 hr post-treatment. Excised lungs were washed in PBS and digested in DMEM containing 200 μg/ml DNase I (Roche, 10104159001), 25 μg/ml Liberase™ (Roche, 05401119001), and Golgi-plug at 37° C. for 6 hrs. The single lung cell suspension was fixed in Cytofix/perm buffer (BD Biosciences) in the dark for 20 min at RT. Fixed cells were then washed and kept in Perm/wash buffer at 4° C. Golgi-plug was present during every step before fixation.

Mouse cDC2 and Monocyte Purification

Primary mouse cDC2 (cat #18970A, Stemcell Technolo-gies; cat #480097, Biolegend) were purified from lungs of naïve mice following the protocol according to the manu-facturer. Mouse monocytes (cat #19861, Stemcell Technolo-gies) were purified from the bone marrow of naïve mice following the protocol according to the manufacturer.

Adoptive Transfer

Pulmonary TNFR2[+] and TNFR2[−] cDC2 were sorted from the lungs of naïve donor mice with a FACSAriaIII flow cytometer. After sorting, dendritic cells were CFSE labeled, according to the protocol from the manufacturer (Invitro-gen). Between 500,000-1,000,000 cells were administered intranasally into recipient mice. 24 hours later of transfer, recipient mice were intranasally vaccinated with CDG (5 μg, Invivogen, cat #vac-cdg) adjuvanted PspA (2 μg, BEI Resources) or PspA alone[17]. Recipient mice received two doses of transferred cells and were immunized at 14 days interval.

Statistical Analysis

All data are expressed as means±SEM. Statistical signifi-cance was evaluated using Prism 5.0 software to perform a Student's t-test (unpaired, two-tailed) for comparison between mean values.

Tm-TNF-Fc Promotes moDCs Expression of Chemokine CXCL13 and $T_F$H Cells Induction in the Lung C57BL/6J mice were immunized with Influenza nucleo-protein (NP)/TNF-Fc(IgG2A) or NP/TNF$_{D221N/A223R}$-Fc (IgG2A) as shown in FIG. 24. Lung moDCs (FIG. 24A) and $T_{FH}$ cells (FIG. 24B) were analyzed on day 14 by Flow cytometry. n=3. CXCL13 is a chemokine essential for the formation of germinal center. The data shows that trans-membrane TNF-Fc induced CXCL13 expression in moDCs. This effect was greater than that observed by sTNF-Fc treatment. tmTNF-FC also induced $T_{FH}$ Cell production from CD4+ T cells.

sTNF-Fc Promotes moDCs Expression of Chemokine CCL20 and Transcriptional Factor Bcl6

C57BL/6J mice were immunized with Influenza nucleo-protein (NP)/TNF-Fc(IgG2A) or NP/TNF$_{D221N/A223R}$-Fc (IgG2A) as shown in FIG. 25. Lung cells were analyzed on day 14 by Flow cytometry. n=3. CCL20 is a T cells recruiting chemokine and Bcl6 is a transcriptional factor important for memory cells development. The data in FIG. 25A shows that soluble TNF-Fc induced CCL20 expression in moDCs, and that this effect was stronger than tmTNF-Fc treatment. In addition, FIG. 25B shows that sTNF-Fc induced Bcl6 expression in moDCs and that this effect was stronger than tmTNF-Fc treatment.

Those skilled in the art will appreciate that conjugations with TNF can be produced using conventional techniques and methods. Examples of IgG2a include, but are not limited to, accession nos AAN76044, AAN76043.1, AAN76042.1, AXN93670.2, and AXN93670.2 and P01859-1 (UniParc). Examples of IgG3 include CAA67886.1, CAC10266.1, CAC10265.1, and CAC10264.1 Also see Human IgG1, IgG3, and IgG3 Hinge-Truncated Mutants Show Different Protection Capabilities against Meningococci Depending on the Target Antigen and Epitope Specificity S. Giuntini, D. M. Granoff, P. T. Beernink, O. Ihle, D. Bratlie, T. E. Michaelsen Clinical and Vaccine Immunology August 2016, 23 (8) 698-706 and Dillon et al. *J Biol Chem.* 2008 Jun. 6; 283(23):16206-15 for information on IgG1 and IgG2 subclass. Also, see UniProt, P01857 for IgG1. Vidarsson et al. *Front Immunol,* 2014 5:520. Web materials for the different Fc regions can be found at invivogen.com/review-antibody-generation. All of the above are incorporated by reference.

REFERENCES

All publications mentioned herein are incorporated by reference in their entirety.

1. Libanova R, Becker P D, Guzman C A. Cyclic dinucleotides: new era for small molecules as adjuvants. Microb *Biotechnol* 2012; 5(2): 168-176.
2. Ebensen T, Schulze K, Riese P, Morr M, Guzman C A. The bacterial second messenger cdiGMP exhibits promising activity as a mucosal adjuvant. *Clin Vaccine Immunol* 2007; 14(8): 952-958.
3. Gray P M, Forrest G, Wisniewski T, Porter G, Freed D C, DeMartino J A et al. Evidence for cyclic diguanylate as a vaccine adjuvant with novel immunostimulatory activities. *Cell Immunol* 2012; 278(1-2): 113-119.
4. Madhun A S, Haaheim L R, Nostbakken J K, Ebensen T, Chichester J, Yusibov V et al. Intranasal c-di-GMP-adjuvanted plant-derived H5 influenza vaccine induces multifunctional Th1 CD4+ cells and strong mucosal and systemic antibody responses in mice. *Vaccine* 2011; 29(31): 4973-4982.
5. Zhao L, KuoLee R, Harris G, Tram K, Yan H, Chen W. c-di-GMP protects against intranasal *Acinetobacter baumannii* infection in mice by chemokine induction and enhanced neutrophil recruitment. *Int Immunopharmacol* 2010; 11(9): 1378-1383.
6. Hu D L, Narita K, Hyodo M, Hayakawa Y, Nakane A, Karaolis D K. c-di-GMP as a vaccine adjuvant enhances protection against systemic methicillin-resistant *Staphylococcus aureus* (MRSA) infection. *Vaccine* 2009; 27(35): 4867-4873.
7. Karaolis D K, Newstead M W, Zeng X, Hyodo M, Hayakawa Y, Bhan U et al. Cyclic di-GMP stimulates protective innate immunity in bacterial pneumonia. *Infect Immun* 2007; 75(10): 4942-4950.
8. Ogunniyi A D, Paton J C, Kirby A C, McCullers J A, Cook J, Hyodo M et al. c-di-GMP is an effective immunomodulator and vaccine adjuvant against pneumococcal infection. *Vaccine* 2008; 26(36): 4676-4685.
9. Yan H, KuoLee R, Tram K, Qiu H, Zhang J, Patel G B et al. 3',5'-Cyclic diguanylic acid elicits mucosal immunity against bacterial infection. *Biochem Biophys Res Commun* 2009; 387(3): 581-584.
10. Smith T T, Moffett H F, Stephan S B, Opel C F, Dumigan A G, Jiang X et al. Biopolymers codelivering engineered T cells and STING agonists can eliminate heterogeneous tumors. *J Clin Invest* 2017; 127(6): 2176-2191.
11. Wang Z, Celis E. STING activator c-di-GMP enhances the anti-tumor effects of peptide vaccines in melanoma-bearing mice. Cancer *Immunol Immunother* 2015; 64(8): 1057-1066.
12. Burdette D L, Monroe K M, Sotelo-Troha K, Iwig J S, Eckert B, Hyodo M et al. STING is a direct innate immune sensor of cyclic di-GMP. *Nature* 2011; 478 (7370): 515-518.
13. Dempsey A, Bowie A G. Innate immune recognition of DNA: A recent history. *Virology* 2015; 479-480: 146-152.
14. Wu J, Chen Z J. Innate immune sensing and signaling of cytosolic nucleic acids. *Annu Rev Immunol* 2014; 32: 461-488.
15. Blaauboer S M, Gabrielle V D, Jin L. MPYS/STING-mediated TNF-alpha, not type I IFN, is essential for the mucosal adjuvant activity of (3'-5')-cyclic-di-guanosine-monophosphate in vivo. *J Immunol* 2014; 192(1): 492-502.
16. Hanson M C, Crespo M P, Abraham W, Moynihan K D, Szeto G L, Chen S H et al. Nanoparticulate STING agonists are potent lymph node-targeted vaccine adjuvants. *J Clin Invest* 2015; 125(6): 2532-2546.
17. Blaauboer S M, Mansouri S, Tucker H R, Wang H L, Gabrielle V D, Jin L. The mucosal adjuvant cyclic di-GMP enhances antigen uptake and selectively activates pinocytosis-efficient cells in vivo. *Elife* 2015; 4.
18. Steinman R M. Decisions about dendritic cells: past, present, and future. *Annu Rev Immunol* 2012; 30: 1-22.
19. Baratin M, Foray C, Demaria O, Habbeddine M, Pollet E, Maurizio J et al. Homeostatic NF-kappaB Signaling in Steady-State Migratory Dendritic Cells Regulates Immune Homeostasis and Tolerance. *Immunity* 2015; 42(4): 627-639.
20. Crowley M, Inaba K, Witmer-Pack M, Steinman R M. The cell surface of mouse dendritic cells: FACS analyses of dendritic cells from different tissues including thymus. *Cell Immunol* 1989; 118(1): 108-125.
21. Mildner A, Jung S. Development and function of dendritic cell subsets. *Immunity* 2014; 40(5): 642-656.
22. Vremec D, Zorbas M, Scollay R, Saunders D J, Ardavin C F, Wu L et al. The surface phenotype of dendritic cells purified from mouse thymus and spleen: investigation of the CD8 expression by a subpopulation of dendritic cells. *J Exp Med* 1992; 176(1): 47-58.
23. Langlet C, Tamoutounour S, Henri S, Luche H, Ardouin L, Gregoire C et al. CD64 expression distinguishes monocyte-derived and conventional dendritic cells and reveals their distinct role during intramuscular immunization. *J Immunol* 2012; 188(4): 1751-1760.
24. Tamoutounour S, Henri S, Lelouard H, de Bovis B, de Haar C, van der Woude C J et al. CD64 distinguishes macrophages from dendritic cells in the gut and reveals the Th1-inducing role of mesenteric lymph node macrophages during colitis. *Eur J Immunol* 2012; 42(12): 3150-3166.
25. Plantinga M, Guilliams M, Vanheerswynghels M, Deswarte K, Branco-Madeira F, Toussaint W et al. Conventional and monocyte-derived CD11b(+) dendritic cells initiate and maintain T helper 2 cell-mediated immunity to house dust mite allergen. *Immunity* 2013; 38(2): 322-335.
26. Holt P G, Schon-Hegrad M A, McMenamin P G. Dendritic cells in the respiratory tract. *Int Rev Immunol* 1990; 6(2-3): 139-149.
27. Schlitzer A, McGovern N, Teo P, Zelante T, Atarashi K, Low D et al. IRF4 transcription factor-dependent CD11b+ dendritic cells in human and mouse control mucosal IL-17 cytokine responses. *Immunity* 2013; 38(5): 970-983.

28. Suzuki S, Honma K, Matsuyama T, Suzuki K, Toriyama K, Akitoyo I et al. Critical roles of interferon regulatory factor 4 in CD11bhighCD8alpha– dendritic cell development. *Proc Natl Acad Sci USA* 2004; 101(24): 8981-8986.

29. Vander Lugt B, Khan A A, Hackney J A, Agrawal S, Lesch J, Zhou M et al. Transcriptional programming of dendritic cells for enhanced MHC class II antigen presentation. *Nat Immunol* 2014; 15(2): 161-167.

30. Hildner K, Edelson B T, Purtha W E, Diamond M, Matsushita H, Kohyama M et al. Batf3 deficiency reveals a critical role for CD8alpha+ dendritic cells in cytotoxic T cell immunity. *Science* 2008; 322(5904): 1097-1100.

31. Murphy K M. Transcriptional control of dendritic cell development. *Adv Immunol* 2013; 120: 239-267.

32. Wallach D, Varfolomeev E E, Malinin N L, Goltsev Y V, Kovalenko A V, Boldin M P. Tumor necrosis factor receptor and Fas signaling mechanisms. *Annu Rev Immunol* 1999; 17: 331-367.

33. Wajant H, Pfizenmaier K, Scheurich P. Tumor necrosis factor signaling. *Cell Death Differ* 2003; 10(1): 45-65.

34. Grell M, Douni E, Wajant H, Lohden M, Clauss M, Maxeiner B et al. The transmembrane form of tumor necrosis factor is the prime activating ligand of the 80 kDa tumor necrosis factor receptor. *Cell* 1995; 83(5): 793-802.

35. Grell M, Wajant H, Zimmermann G, Scheurich P. The type 1 receptor (CD120a) is the high-affinity receptor for soluble tumor necrosis factor. *Proc Natl Acad Sci USA* 1998; 95(2): 570-575.

36. Guilliams M, Dutertre C A, Scott C L, McGovern N, Sichien D, Chakarov S et al. Unsupervised High-Dimensional Analysis Aligns Dendritic Cells across Tissues and Species. *Immunity* 2016; 45(3): 669-684.

37. Sichien D, Scott C L, Martens L, Vanderkerken M, Van Gassen S, Plantinga M et al. IRF8 Transcription Factor Controls Survival and Function of Terminally Differentiated Conventional and Plasmacytoid Dendritic Cells, Respectively. *Immunity* 2016; 45(3): 626-640.

38. Jin L, Getahun A, Knowles H M, Mogan J, Akerlund L J, Packard T A et al. STING/MPYS Mediates Host Defense against *Listeria monocytogenes* Infection by Regulating Ly6Chi Monocyte Migration. *J Immunol* 2013; 190(6): 2835-2843.

39. Jin L, Hill K K, Filak H, Mogan J, Knowles H, Zhang B et al. MPYS is required for IFN response factor 3 activation and type I IFN production in the response of cultured phagocytes to bacterial second messengers cyclic-di-AMP and cyclic-di-GMP. *J Immunol* 2011; 187(5): 2595-2601.

40. Klein U, Casola S, Cattoretti G, Shen Q, Lia M, Mo T et al. Transcription factor IRF4 controls plasma cell differentiation and class-switch recombination. *Nat Immunol* 2006; 7(7): 773-782.

41. Pfeffer K, Matsuyama T, Kundig T M, Wakeham A, Kishihara K, Shahinian A et al. Mice deficient for the 55 kd tumor necrosis factor receptor are resistant to endotoxic shock, yet succumb to *L. monocytogenes* infection. *Cell* 1993; 73(3): 457-467.

42. Erickson S L, de Sauvage F J, Kikly K, Carver-Moore K, Pitts-Meek S, Gillett N et al. Decreased sensitivity to tumour-necrosis factor but normal T-cell development in TNF receptor-2-deficient mice. *Nature* 1994; 372(6506): 560-563.

43. De Silva N S, Silva K, Anderson M M, Bhagat G, Klein U. Impairment of Mature B Cell Maintenance upon Combined Deletion of the Alternative N F-kappaB Transcription Factors RELB and N F-kappaB2 in B Cells. *J Immunol* 2016; 196(6): 2591-2601.

44. Caton M L, Smith-Raska M R, Reizis B. Notch-RBP-J signaling controls the homeostasis of CD8– dendritic cells in the spleen. *J Exp Med* 2007; 204(7): 1653-1664.

Although the present invention has been described in considerable detail with reference to certain preferred versions thereof, other versions are possible. Therefore, the spirit and scope of the appended claims should not be limited to the description of the preferred versions contained herein.

The reader's attention is directed to all papers and documents which are filed concurrently with this specification and which are open to public inspection with this specification, and the contents of all such papers and documents are incorporated herein by reference.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means for" performing a specified function, or "step for" performing a specific function, is not to be interpreted as a "means" or "step" clause as specified in 35 U.S.C § 112, sixth paragraph. In particular, the use of "step of" in the claims herein is not intended to invoke the provisions of 35 U.S.C § 112, sixth paragraph.

What is claimed is:

1. A vaccine composition comprising a therapeutically effective amount of
an antigen;
a cyclic dinucleotide; and
tumor necrosis factor (TNF) conjugated with a moDC targeting moiety; and, optionally, a CD64 antibody or antibody fragment;
wherein the antigen comprises H7HA, H7N7, PspA, influenza nucleoprotein (NP), HIVenvV1V2 or HIV-1pr55Gag.

2. The vaccine composition of claim 1, wherein the cyclic dinucleotide comprises cyclic-di-GMP (CDG), cyclic-di-AMP (CDA), cyclic-di-IMP (CDI), cyclic-AMP-GMP (CDA/G), cyclic-AMP-IMP (CDA/I, and cyclic-GMP-IMP (CDG/I).

3. The vaccine composition of claim 1, wherein the CD64 antibody or antibody fragment is a monoclonal antibody.

4. The vaccine composition of claim 1, wherein the vaccine composition further comprises a pharmaceutically acceptable carrier.

5. The vaccine composition of claim 1, wherein the TNF conjugated with a moDC targeting moiety comprises an anti-CD64 antibody conjugated-TNF and/or Fc conjugated TNF.

6. A method of eliciting an immune response in a subject comprising administering to the subject a vaccine composition of claim 1.

7. The method of claim 6, wherein the immune response comprises activation of monocyte derived dendritic cells (moDCs).

8. A kit comprising an inhalative administration device and the vaccine composition of claim 1.

9. The kit of claim 8, wherein the vaccine composition is provided in container separate to the inhalative administration device.

10. The kit of claim 8, wherein the vaccine composition is disposed within the inhalative administration device.

11. A method for treating, or preventing, a disease or condition in a subject, the method comprising administering to the subject the composition of claim 1.

12. The method of claim 11, wherein the disease or condition comprises cancer or an infection.

13. The adjuvant composition of claim 1 wherein the composition comprise a CD64 antibody or antibody fragment.

14. The adjuvant composition of claim 13, further comprising a pharmaceutically acceptable carrier.

15. An adjuvant composition comprising TNF conjugated with an moDC targeting moiety.

16. The adjuvant composition of claim 15, wherein the moDC targeting moiety comprises Fc of an IgG2a antibody isotype.

17. The adjuvant composition of claim 15 wherein TNF is sTNF or tmTNF.

18. The adjuvant composition of claim 17, wherein tmTNF binds only TNFR2.

* * * * *